United States Patent
Murphy et al.

(10) Patent No.: US 12,233,080 B2
(45) Date of Patent: *Feb. 25, 2025

(54) LIPOTECHOIC ACID FOR IMMUNE MODULATION

(71) Applicant: Northwestern University, Evanston, IL (US)

(72) Inventors: Stephen F. Murphy, Chicago, IL (US); Praveen Thumbikat, Chicago, IL (US); Anthony Schaeffer, Hinsdale, IL (US)

(73) Assignee: Northwestern University, Evanston, IL (US)

( * ) Notice: Subject to any disclaimer, the term of this patent is extended or adjusted under 35 U.S.C. 154(b) by 1091 days.

This patent is subject to a terminal disclaimer.

(21) Appl. No.: 17/037,079

(22) Filed: Sep. 29, 2020

(65) Prior Publication Data
US 2021/0023109 A1 Jan. 28, 2021

Related U.S. Application Data

(63) Continuation of application No. 15/923,679, filed on Mar. 16, 2018, now Pat. No. 10,799,520.

(60) Provisional application No. 62/473,022, filed on Mar. 17, 2017.

(51) Int. Cl.
| | |
|---|---|
| *A61K 39/085* | (2006.01) |
| *A61K 9/00* | (2006.01) |
| *A61K 31/7032* | (2006.01) |
| *A61K 35/00* | (2006.01) |
| *A61K 35/741* | (2015.01) |
| *A61P 19/02* | (2006.01) |
| *A61P 29/00* | (2006.01) |
| *A61P 37/06* | (2006.01) |

(52) U.S. Cl.
CPC ........ *A61K 31/7032* (2013.01); *A61K 9/0031* (2013.01); *A61K 9/0053* (2013.01); *A61K 35/741* (2013.01); *A61K 39/085* (2013.01); *A61P 19/02* (2018.01); *A61P 29/00* (2018.01); *A61P 37/06* (2018.01); *A61K 2035/115* (2013.01)

(58) Field of Classification Search
None
See application file for complete search history.

(56) References Cited

U.S. PATENT DOCUMENTS

| | | | |
|---|---|---|---|
| 8,449,878 B2 | 5/2013 | Yonak | |
| 10,799,520 B2 * | 10/2020 | Murphy | A61K 35/741 |
| 2010/0166708 A1 | 7/2010 | Gallo et al. | |
| 2018/0280419 A1 | 10/2018 | Murphy et al. | |

OTHER PUBLICATIONS

MacLea et al. Genome Announc. 5(36): e00954-17, 1-2, 2017.*
Wei et al. BMC Genomics 7: Article No. 112, pp. 1-12, 2006.*
Lai et al. Nat. Med. 15: 1377-1382, 1-19, 2009.*
Supplementary Information pp. 1-10 of Lai et al. Nat. Med. 15: 1377-1382, 1-19, 2009.*
Aulock et al., Lipoteichoic acid from *Staphylococcus aureus* is a potent stimulus for neutrophil recruitment, Immunobiology. 2003;208(4):413-22.
Belkaid et al., Compartmentalized and systemic control of tissue immunity by commensals, Nat Immunol. Jul. 2013;14(7):646-53.
Belkaid et al., Dialogue between skin microbiota and immunity, Science. Nov. 21, 2014;346(6212):954-9.
Benwell et al., Essential and synergistic roles of IL1 and IL6 in human Th17 differentiation directed by TLR ligand-activated dendritic cells. Clin Immunol. Feb. 2010;134(2):178-87.
Bowie et al., Bacteriology of the urethra in normal men and men with nongonococcal urethritis, J Clin Microbiol. Nov. 1977;6(5):482-8.
Buttner et al., Structural basis of *Staphylococcus epidermidis* biofilm formation: mechanisms and molecular interactions, Front Cell Infect Microbiol. Feb. 17, 2015;5:14.
Chiu et al., Bacteria activate sensory neurons that modulate pain and inflammation, Nature. Sep. 5, 2013;501(7465):52-7.
Christensen et al., Bacterial skin commensals and their role as host guardians, Benef Microbes. Jun. 1, 2014;5(2):201-15.
Desireddi et al., Monocyte Chemoattractant Protein-1 and Macrophage Inflammatory Protein-1α as Possible Biomarkers for the Chronic Pelvic Pain Syndrome, J Urol. May 2008;179(5):1857-61; discussion 1861-2.
Gaddis et al., Role of TLR2-dependent IL-10 production in the inhibition of the initial IFN-γ T cell response to Porphyromonas gingivalis, J Leukoc Biol. Jan. 2013;93(1):21-31.
Gallegos et al., Driven to Autoimmunity: The Nod Mouse, Cell. Apr. 16, 2004;117(2):149-51.
Gallo et al., Microbial Symbiosis with the Innate Immune Defense System of the Skin, J Invest Dermatol. Oct. 2011;131(10):1974-80.
Gao et al., TLR2 Directing PD-L2 Expression Inhibit T Cells Response in Schistosoma japonicum Infection, PLoS One. Dec. 20, 2013;8(12):e82480.

(Continued)

*Primary Examiner* — S. Devi

(74) *Attorney, Agent, or Firm* — David W. Staple; Casimir Jones, S.C.

(57) ABSTRACT

Provided herein are compositions comprising lipotechoic acid (LTA) and methods of use thereof for immune modulation. In particular, compositions comprising *S. epidermidis* lipotechoic Acid (SELTA) are provided, as well as method of use thereof for the treatment of immune—(e.g., autoimmune) and inflammation-related conditions and diseases (e.g., chronic pelvic pain syndrome (CPPS), arthritis, etc.).

6 Claims, 41 Drawing Sheets

Specification includes a Sequence Listing.

(56) References Cited

OTHER PUBLICATIONS

Grangette et al., Enhanced antiinflammatory capacity of a Lactobacillus plantarum mutant synthesizing modified teichoic acids. Proc Natl Acad Sci U S A. Jul. 19, 2005;102(29):10321-6.
Guo et al., Taxonomic Precision of Different Hypervariable Regions of 16S rRNA Gene and Annotation Methods for Functional Bacterial Groups in Biological Wastewater Treatment, PLoS One. Oct. 16, 2013;8(10):e76185.
Hamady et al., Microbial community profiling for human microbiome projects: Tools, techniques, and challenges, Genome Res. Jul. 2009; 19(7):1141-52.
Hou et al., Characterisation of the bacterial community in expressed prostatic secretions from patients with chronic prostatitis/chronic pelvic pain syndrome and infertile men: a preliminary investigation, Asian J Androl. Jul. 2012;14(4):566-73.
Huang et al., Interaction of inflammatory and anti-inflammatory responses in microglia by *Staphylococcus aureus*-derived lipoteichoic acid, Toxicol Appl Pharmacol. May 15, 2013;269(1):43-50.
Kim et al., Interleukin-17 Contributes to Neuroinflammation and Neuropathic Pain Following Peripheral Nerve Injury in Mice, J Pain. Mar. 2011;12(3):370-83.
Kirschning et al., Toll-like receptors: cellular signal transducers for exogenous molecular patterns causing immune responses, Int J Med Microbiol. Sep. 2001;291(4):251-60.
Kunz et al., Cytokines and Cytokine Profiles in Human Autoimmune Diseases and Animal Models of Autoimmunity, Mediators Inflamm. 2009;2009:979258.
Kuriya et al., Double deficiency in IL-17 and IFN-γ signalling significantly suppresses the development of diabetes in the NOD mouse, Diabetologia. Aug. 2013;56(8):1773-80.
Lai et al., Commensal bacteria regulate Toll-like receptor 3-dependent inflammation after skin injury, Nat Med. Dec. 2009;15(12):1377-82.
Lambert et al., Lipid S, a novel *Staphylococcus epidermidis* exocellular antigen with potential for the serodiagnosis of infections, FEMS Immunol Med Microbiol. Nov. 2000;29(3):195-202.
Lewis et al., The human urinary microbiome; bacterial DNA in voided urine of asymptomatic adults, Front Cell Infect Microbiol. Aug. 15, 2013;3:41.
Liu et al., TLR2 and TLR4 in Autoimmune Diseases: a Comprehensive Review, Clin Rev Allergy Immunol. Oct. 2014;47(2):136-47.
Magetsari et al., Cinnamon Oil and Chitosan Coating on Orthopaedic Implant Surface for Prevention of Staphylococcus Epidermidis Biofilm Formation, Malays Orthop J. Nov. 2014;8(3):11-4.
McMahon et al., Crosstalk between the nociceptive and immune systems in host defense and disease, Nat Rev Neurosci. Jul. 2015;16(7):389-402.
Morrison et al., Th17-cell plasticity in Helicobacter hepaticus-induced intestinal inflammation, Mucosal Immunol. Nov. 2013;6(6):1143-56.
Murphy et al., Commensal bacterial modulation of the host immune response to ameliorate pain in a murine model of chronic prostatitis, Pain. Aug. 2017;158(8):1517-1527.
Murphy et al., IL17 Mediates Pelvic Pain in Experimental Autoimmune Prostatitis (EAP), PLoS One. May 1, 2015;10(5):e0125623.
Murphy et al., Infiltration of Th1 and Th17 cells and activation of microglia in the CNS during the course of experimental autoimmune encephalomyelitis, Brain Behav Immun. May 2010;24(4):641-51.
Naik et al., Commensal-dendritic-cell interaction specifies a unique protective skin immune signature, Nature. Apr. 2, 2015;520(7545):104-8.
Naik et al., Compartmentalized Control of Skin Immunity by Resident Commensals, Science. Aug. 31, 2012;337(6098):1115-9.
Nickel et al., Search for Microorganisms in Men with Urologic Chronic Pelvic Pain Syndrome: A Culture-Independent Analysis in the MAPP Research Network, J Urol. Jul. 2015;194(1):127-35.

Pietrocola et al., Toll-Like Receptors (TLRs) in Innate Immune Defense Against *Staphylococcus aureus*, Int J Artif Organs. Sep. 2011;34(9):799-810.
Polanczyk et al., Estrogen-mediated immunomodulation involves reduced activation of effector T cells, potentiation of Treg cells, and enhanced expression of the PD-1 costimulatory pathway, J Neurosci Res. Aug. 1, 2006;84(2):370-8.
Quick et al., Measurement of Tactile Allodynia in a Murine Model of Bacterial Prostatitis, J Vis Exp. Jan. 16, 2013;(71):e50158.
Quick et al., Th1-Th17 Cells Contribute to the Development of Uropathogenic *Escherichia coli*-Induced Chronic Pelvic Pain, PLoS One. 2013;8(4):e60987.
Rashidi et al., Lipopolysaccharide—and Lipoteichoic Acid-mediated Pro-inflammatory Cytokine Production and Modulation of TLR2, TLR4 and MyD88 Expression in Human Endometrial Cells,J Reprod Infertil. Apr.-Jun. 2015;16(2):72-81.
Rivero et al., Non-obese Diabetic (NOD) Mice are Genetically Susceptible to Experimental Autoimmune Prostatitis (EAP), J Autoimmun. Dec. 1998;11(6):603-10.
Roman et al., Tryptase—PAR2 axis in Experimental Autoimmune Prostatitis, a model for Chronic Pelvic Pain Syndrome, Pain. Jul. 2014;155(7):1328-38.
Round et al., The Toll-like receptor pathway establishes commensal gut colonization, Science. May 20, 2011;332(6032):974-7.
Rudick et al., Experimental autoimmune prostatitis induces chronic pelvic pain, Am J Physiol Regul Integr Comp Physiol. Apr. 2008;294(4):R1268-75.
Rudick et al., Host-Pathogen Interactions Mediating Pain of Urinary Tract Infection, J Infect Dis. Apr. 15, 2010;201(8):1240-9.
Rudick et al., Uropathogenic *Escherichia coli* Induces Chronic Pelvic Pain, Infect Immun. Feb. 2011;79(2):628-35.
Singh et al., Th17 cells in inflammation and autoimmunity, Autoimmun Rev. Dec. 2014;13(12):1174-81.
Soergel et al., Selection of primers for optimal taxonomic classification of environmental 16S rRNA gene sequences, ISME J. Jul. 2012;6(7):1440-4.
Stokes et al., Spinal Toll-like receptor signaling and nociceptive processing: Regulatory balance between TIRAP and TRIF cascades mediated by TNF and IFNß, Pain. May 2013;154(5):733-42.
Tang et al., The advantages of PD1 activating chimeric receptor (PD1-ACR) engineered lymphocytes for PDL1+ cancer therapy, Am J Transl Res. Mar. 15, 2015;7(3):460-73. eCollection 2015.
Tankeshwar, Teichoic Acid/Lipoteichoic Acid: Characteristics and Medical Importance. Microbe Online. Apr. 2013, downloaded from the internet, <https://microbeonline.com/teichoic-acid-of-gram-positive-bacteria-characteristics-and-medical-importance/> on May 2018, pp. 1-2.
Tripathi et al., Role of PD1/PDL1 pathway, and TH17 and treg cells in maternal tolerance to the fetus, Biomed J. Jan.-Feb. 2015;38(1):25-31.
Wang et al., Control of Adaptive Immune Responses by *Staphylococcus aureus* through IL-10, PD-L1, and TLR2, Sci Rep. 2012;2:606.
Woolley et al., Microbiological flora in men with non-gonococcal urethritis with particular reference to anaerobic bacteria, Int J STD AIDS. Mar. 1990;1(2):122-5.
Yao et al., Advances in targeting cell surface signalling molecules for immune modulation, Nat Rev Drug Discov. Feb. 2013;12(2):130-46.
Yu et al., Urinary microbiota in patients with prostate cancer and benign prostatic hyperplasia, Arch Med Sci. Apr. 25, 2015;11(2):385-94.
Zhang et al., Synergy of ambroxol with vancomycin in elimination of catheter-related *Staphylococcus epidermidis* biofilm in vitro and in vivo, J Infect Chemother. Nov. 2015;21(11):808-15.
Zielinski et al., Pathogen-induced human TH17 cells produce IFN-γ or IL-10 and are regulated by IL-1ß, Nature. Apr. 26, 2012;484(7395):514-8.
International Search Report of related PCT/US2018/22902, mailed May 16, 2018, 13 pages.

* cited by examiner

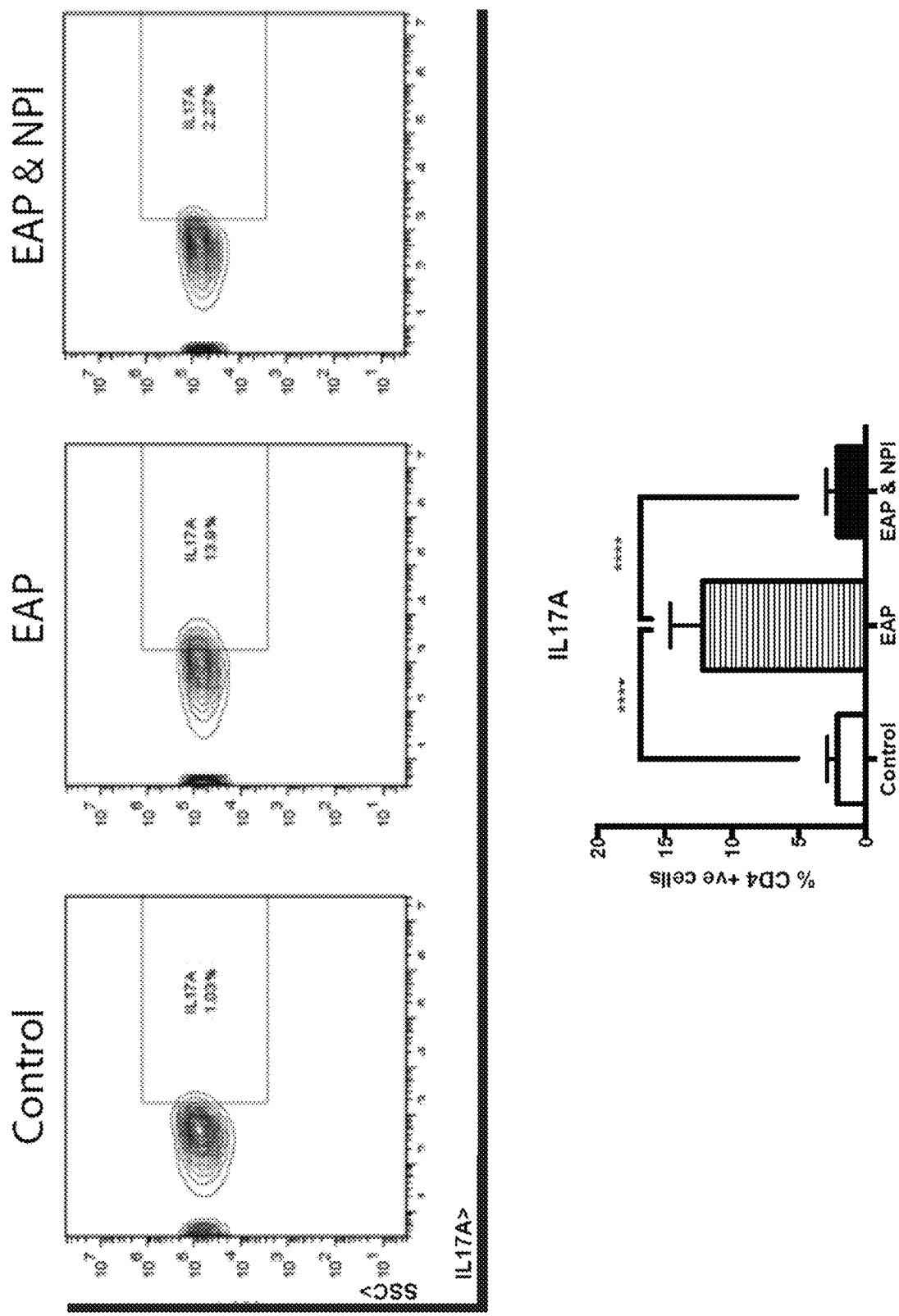

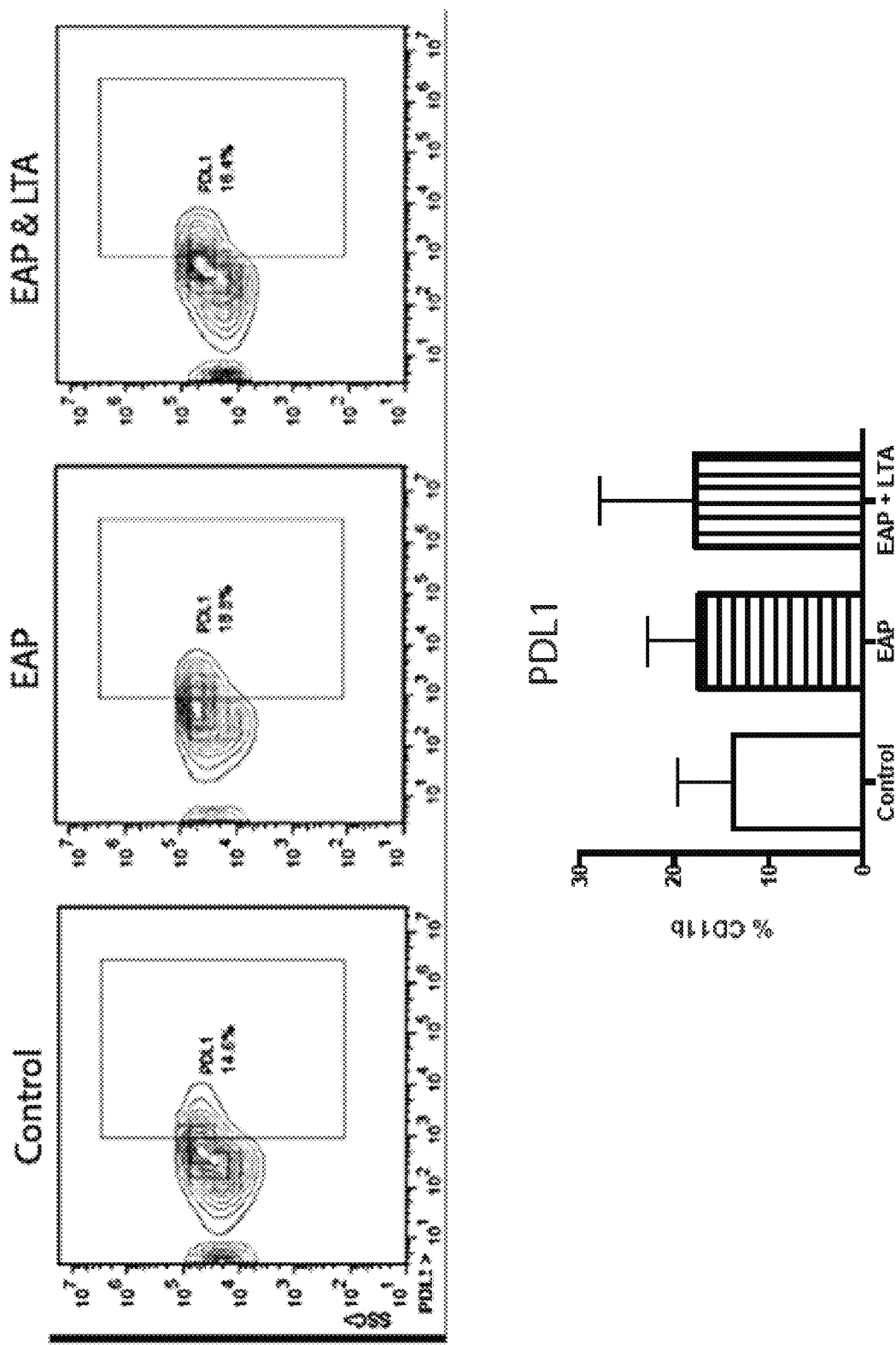

LIPOTECHOIC ACID FOR IMMUNE MODULATION

CROSS-REFERENCE TO RELATED APPLICATIONS

The present invention is a continuation of U.S. patent application Ser. No. 15/923,679, filed Mar. 16, 2018, now U.S. Pat. No. 10,799,520, which claims priority to U.S. Provisional Patent Application No. 62/473,022, filed Mar. 17, 2017, each of which is incorporated by reference in its entirety.

STATEMENT REGARDING FEDERAL FUNDING

This invention was made with government support under DK094898 awarded by the National Institutes of Health. The government has certain rights in the invention.

SEQUENCE LISTING PARAGRAPH

The text of the computer readable sequence listing filed herewith, titled "NWEST_35172.303_ST25.txt", created Nov. 15, 2024, having a file size of 3,227 bytes, is hereby incorporated by reference in its entirety.

FIELD

Provided herein are compositions comprising lipotechoic acid (LTA) and methods of use thereof for immune modulation. In particular, compositions comprising *S. epidermidis* lipotechoic Acid (SELTA) are provided, as well as method of use thereof for the treatment of immune—(e.g., autoimmune) and inflammation-related conditions and diseases (e.g., chronic pelvic pain syndrome (CPPS), arthritis, etc.).

BACKGROUND

*Staphylococcus epidermidis* (SE) is a commensal bacterium of the skin (ref. 7; incorporated by reference in its entirety) that has a role in mediating local immune homeostasis (ref. 11; incorporated by reference in its entirety). During local immune activation it can dampen inflammation signals (ref. 27; incorporated by reference in its entirety) and prevent pathogenic superinfection by species such as *S. aureus* (refs. 1-2; incorporated by reference in their entireties). SE also acts as a facultative pathogen forming biofilms on surgically implanted materials (refs. 5,21,49; incorporated by reference in their entireties). Recently, a more distinct method of immune interaction via specific subdermal dendritic cells has been described (ref. 26; incorporated by reference in its entirety) involving activation of the IL1 and IL17 signaling pathways. The cell wall LTA is an immunogenic pathogen associated molecular pattern (PAMP) and signals via TLR2 (refs. 16,29; incorporated by reference in their entireties). TLR2 mediates signaling responses by forming homo or hetero dimers with TLR1 and/or TLR6. Resulting downstream signaling is determined by which dimer is engaged and which signaling intermediaries are utilized.

Chronic pelvic pain syndrome (CPPS) is a disorder characterized by pelvic pain and frequently lower urinary tract symptoms (LUTS). CPPS is classically not associated with bacterial infection but prostate specific bacterial strains have been isolated from the expressed prostatic secretions (EPS) of both CPPS patients and controls. Patient-derived gram-negative uropathogenic *E. coli* (UPEC) bacteria has been shown to establish tactile allodynia in male NOD mouse by initiating a Th17 mediated prostate immune activation (ref. 32; incorporated by reference in its entirety). These effects were restricted to the genetically susceptible NOD mice compared to C57BL/6 mice. Pelvic tactile allodynia and immune activation persisted even after bacterial clearance (refs. 32,37; incorporated by reference in their entireties).

SUMMARY

Provided herein are compositions comprising lipotechoic acid (LTA) and methods of use thereof for immune modulation. In particular, compositions comprising *S. epidermidis* lipotechoic acid (SELTA) are provided, as well as method of use thereof for the treatment of immune—(e.g., autoimmune) and inflammation-related conditions and diseases (e.g., chronic pelvic pain syndrome (CPPS), arthritis, etc.).

In some embodiments, provided herein are compositions formulated for administration to a subject comprising *Staphylococcus epidermidis* lipotechoic acid (LTA). In some embodiments, compositions comprise a probiotic comprising live *S. epidermidis* bacteria. In some embodiments, the *S. epidermidis* bacteria comprise the NPI strain. In some embodiments, compositions comprise isolated LTA. In some embodiments, the isolated LTA is derived from the cell of *S. epidermidis* bacteria. In some embodiments, the isolated LTA is synthesized (e.g., chemical synthesis of LTA molecules) and/or formulated synthetically (e.g., combination of LTA molecules to generate an LTA composition of specific LTA make-up). In some embodiments, the LTA comprises one or more chemical species of Formula I:

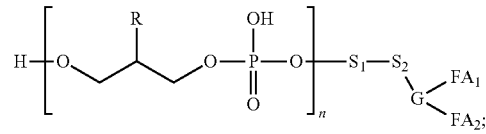

(Formula I)

wherein n is 2-100; wherein each R is any suitable amino acid, saccharide, or H; wherein $S_1$ and $S_2$ are monosaccharides connected by any suitable linker; wherein G is a glyceride moiety; and wherein $FA_1$ and $FA_2$ are fatty acids. In some embodiments, one or more R is D-alanine, a monosaccharide, or H. In some embodiments, $S_1$ and $S_2$ are independently D-glucose, fructose, mannose, galactose, glucosamine, xylopyranose, or rhamnose, connected by linker selected from α(1→2), α(1→3), α(1→6), β(1→2)β, β(1→2), β(1→3), and β(1→6). In some embodiments, $FA_1$ and $FA_2$ are independently saturated or unsaturated fatty acids of any suitable length.

In some embodiments, provided herein are methods of treating an inflammation- and/or immune-related disease or condition in a subject, the method comprising administering to the subject a composition comprising *Staphylococcus epidermidis* lipotechoic acid (LTA) described herein. In some embodiments, provided herein is the use of a composition comprising *Staphylococcus epidermidis* lipotechoic acid (LTA) described herein for the treatment of an inflammation- and/or immune-related disease or condition in a subject. In some embodiments, an immune response of the subject is modulated. In some embodiments, the disease is an autoimmune disease. In some embodiments, inflammation is reduced in the subject. In some embodiments, the disease is chronic pelvic pain syndrome (CPPS). In some embodiments, the disease is arthritis (e.g., rheumatoid arthritis). In some embodiments, the composition is administered orally. In some embodiments, the composition is administered rectally.

BRIEF DESCRIPTION OF THE DRAWINGS

(FIGS. 1A, 1B) Pain response frequencies, as assessed by Von Frey filament testing, in controls and NPI instilled NOD mice. Pain response is depicted as increased percentage response frequency above baseline every 7 days for 28 days and Individual percentage response frequencies for filaments of increasing force (x-axis). n=4/5 mice per group. (FIG. 1C) QRTPCR for T-cell markers from prostate tissues of control and NPI instilled NOD mice, normalized against L19 (housekeeping gene) & CD4 expression levels.

FIGS. 2A-E. NPI instillation reverses EAP induced tactile allodynia in C57BL/6 mice. (FIG. 2A) Tactile allodynia response frequencies, in controls, EAP and EAP with NPI instillation at day 21, in C57BL/6 mice, every 7 days for 28 days. Pain response is depicted as increased percentage response frequency above baseline. (FIG. 2B) Tactile allodynia response change following instillation with NPI, using day 21 as baseline. (FIG. 2C) Individual percentage response frequencies for filaments of increasing force (x-axis). Representative flow cytometry plots for IL17A expression (gated on CD4+ve lymphocytes) in single cell suspensions of (FIG. 2D) prostate tissue and (FIG. 2E) iliac lymph nodes, from control, EAP and EAP with NPI instillation, of C57BL/6 mice, at day 28, 7-days post-instillation.

(FIG. 3A) Tactile allodynia response frequencies, in controls, EAP, EAP with NPI instillation and EAP with 7244 at day 28, in C57BL/6 mice, at day 28, day 29 (1), day 31 (3) and day 35 (7). Pain response is depicted as increased percentage response frequency above baseline. Tactile allodynia response change following instillation with bacteria, using day 28 as baseline is also shown. (FIGS. 3B-3E) Individual percentage response frequencies for filaments of increasing force (x-axis). (FIG. 3F) Colony formation assay per tissue for prostate and bladder are shown for mice at day 1 (i & iv), day 3 (ii & v) and day 7 (iii & vi).

(FIG. 4A) Tactile allodynia response frequencies, in controls, EAP and EAP with LTA treatment at day 21, in C57BL/6 mice, every 7 days for 28 days. Pain response is depicted as increased percentage response frequency above baseline. (FIG. 4B) Tactile allodynia response change following treatment with LTA, using day 21 as baseline. (FIG. 4C) Individual percentage response frequencies for filaments of increasing force (x-axis). Representative flow cytometry plots for IL17A expression in single cell suspensions of (FIG. 4D) prostate tissue from control, EAP and EAP with LTA treatment, of C57BL/6 mice, at day 28, 7-days post-treatment. (FIG. 4E) Iliac lymph node tissue. (FIG. 4F) Tactile allodynia response frequencies, in controls, EAP, EAP with SELTA, EAP with SELTA II ($2^{nd}$ batch), EAP with SALTA (*S. aureus*), and EAP with BSLTA (*B. subtilis*) in C57BL/6 mice, every 7 days for 35 days. Pain response is depicted as increased percentage response frequency above baseline. (FIG. 4G) Tactile allodynia response change following treatment with various LTAs, using day 28 as baseline. (FIGS. 4H-I) Individual percentage response frequencies for filaments of increasing force (x-axis).

(FIGS. 5A-B) Representative flow cytometry plots for PDL1 and PDL2 expression (gated on CD11b+ve cells) in single cell suspensions of prostate tissue from control, EAP and EAP with LTA treatment, of C57BL/6 mice, at day 28, 7-days post-treatment. (FIGS. 5C-D) Representative images of immune-fluorescent staining for PDL1 and PDL2 with DAPI on paraffin section of murine prostate. (FIG. 5E) Expression of PD1 by flow cytometry from single cell suspensions of C57BL/6 control, EAP and EAP with LTA treatment, gated on CD4.

(FIG. 6A) Tactile allodynia response changes of control, EAP, EAP with NPI and NPI only IL10-KO mice every 7 days for 28 days. (FIG. 6B) Pain responses depicted using day 21 as baseline demonstrating effect of NPI instillation of tactile allodynia in absence of IL10. (FIG. 6C) Responses to individual Von Frey filaments. (FIG. 6D) Percentage tactile allodynia response changes of control, EAP, EAP with LTA, EAP with IgG control, EAP with anti-PD1, EAP with anti-PD1 & LTA, EAP with anti-CD25 and EAP with anti-CD25 & LTA, EAP with anti-CD25 & LTA every 7 days for 28 days. (FIG. 6E) Tactile allodynia responses depicted using day 21 as baseline demonstrating effect of NPI instillation of tactile allodynia in absence of IL10. (FIG. 6F-G) Responses to individual Von Frey filaments.

FIGS. 7A-E. Effect of LTA on PDL1/2 expression is prostate specific. (FIGS. 7A-D) Representative flow cytometry plots of single cell suspensions of (FIGS. 7A-B) iliac lymph node and (FIGS. 7C-D) bladder tissues for (FIGS. 7A, 7C) PDL1 and (FIGS. 7B, 7D) PDL2 expression (gated on CD11b+ve cells) in control, EAP and EAP with LTA treatment C57BL/6 mice, at day 28, 7-days post-treatment. (FIG. 7E) Expression of PD1 by flow cytometry (gated on CD4+ve lymphocytes) from single cell suspensions of control, EAP and EAP with LTA treatment mice.

(FIG. 10A) Mice with CIA were tested at the time points shown to test paw withdrawal (a measure of allodynia). Both left and right paws were tested for each mouse group (N=5). (FIG. 10B) Paw withdrawal measurements at time points following injection with LTA or a sham injection. Mice were treated every three days.

Definitions

Figure 1A:
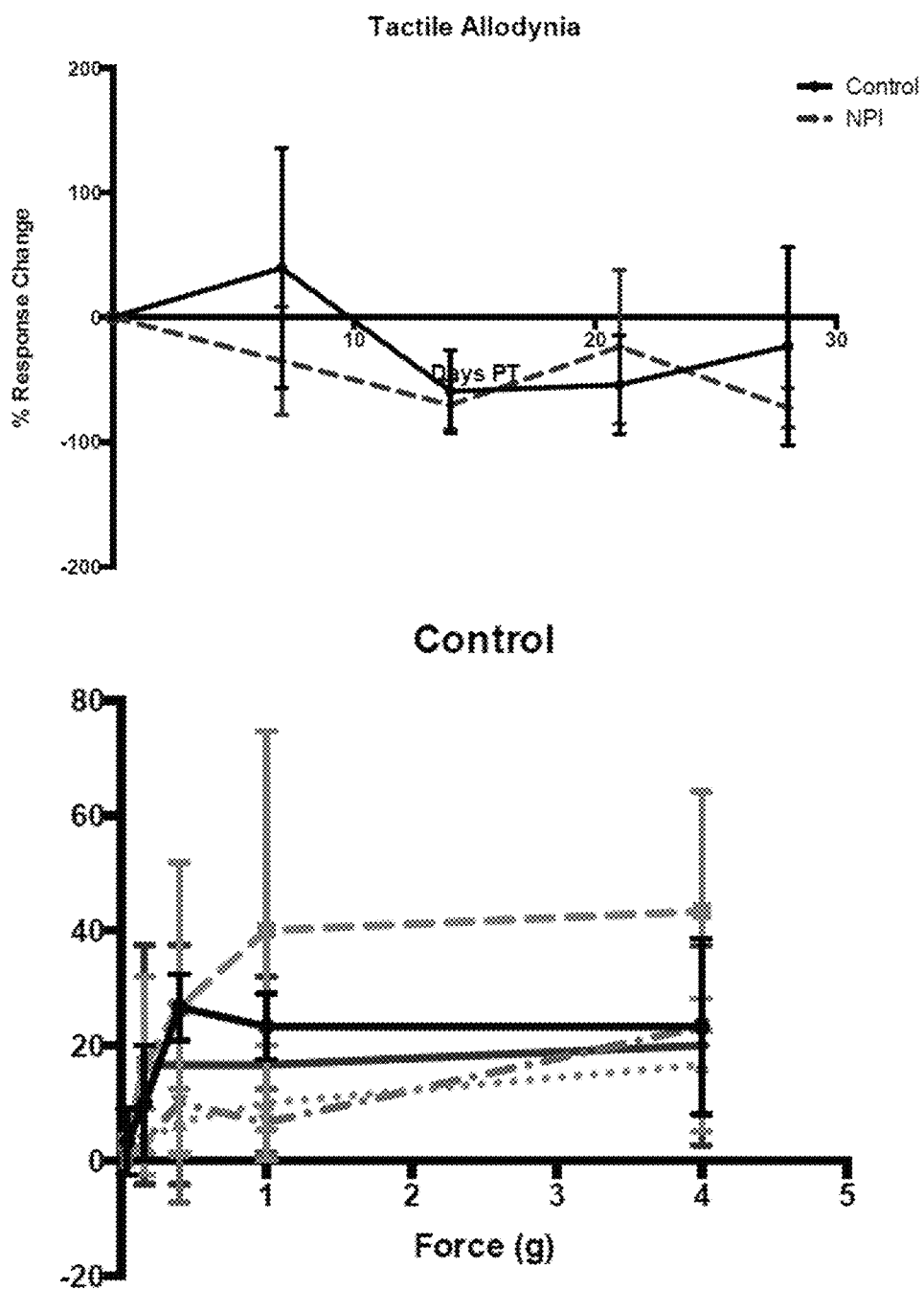
FIGS. 1A-C. Intra-urethral instillation of human derived NPI does not induce tactile allodynia.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a probiotic agent" is a reference to one or more probiotic agents and equivalents thereof known to those skilled in the art, and so forth.

As used herein, the term "and/or" includes any and all combinations of listed items, including any of the listed items individually. For example, "A, B, and/or C" encompasses A, B, C, AB, AC, BC, and ABC, each of which is to be considered separately described by the statement "A, B, and/or C." As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "non-pain-inducing strain of *Staphylococcus epidermidis*" or "NPI" refers to the bacterial strain of ATTC Patent Deposit #PTA-127829.

As used herein, the term "subject" broadly refers to any animal, including but not limited to, human and non-human animals (e.g., dogs, cats, cows, horses, sheep, poultry (e.g., chickens), fish, crustaceans, etc.). As used herein, the term "patient" typically refers to a human subject that is being treated for a disease or condition.

As used herein, the term "effective amount" refers to the amount of a composition sufficient to effect beneficial or desired results. An effective amount can be administered in one or more administrations, applications or dosages and is not intended to be limited to a particular formulation or administration route.

As used herein, the terms "administration" and "administering" refer to the act of giving a drug, prodrug, or other agent, or therapeutic treatment to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) (e.g., a pharmaceutical composition comprising beneficial bacteria, and/or additional therapeutics) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "pharmaceutical composition" refers to the combination of an active agent with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintigrants (e.g., potato starch or sodium starch glycolate), and the like. The compositions also can include stabilizers and preservatives. For examples of carriers, stabilizers and adjuvants, see, e.g., Martin, Remington's Pharmaceutical Sciences, 15th Ed., Mack Publ. Co., Easton, Pa. (1975), incorporated herein by reference in its entirety.

As used herein, a "prebiotic" refers to an ingredient that allows specific changes, both in the composition and/or activity in the gastrointestinal microbiota that may (or may not) confer benefits upon the host. In some embodiments, a prebiotic is a comestible food or beverage or ingredient thereof. In some embodiments, a prebiotic is a selectively fermented ingredient. Prebiotics may include complex carbohydrates, amino acids, peptides, minerals, or other essential nutritional components for the survival of the bacterial composition. Prebiotics include, but are not limited to, amino acids, biotin, fructooligosaccharide, galactooligosaccharides, hemicelluloses (e.g., arabinoxylan, xylan, xyloglucan, and glucomannan), inulin, chitin, lactulose, mannan oligosaccharides, oligofructose-enriched inulin, gums (e.g., guar gum, gum arabic and carregenaan), oligofructose, oligodextrose, tagatose, resistant maltodextrins (e.g., resistant starch), trans-galactooligosaccharide, pectins (e.g., xylogalactouronan, citrus pectin, apple pectin, and rhamnogalacturonan-I), dietary fibers (e.g., soy fiber, sugarbeet fiber, pea fiber, corn bran, and oat fiber) and xylooligosaccharides.

The term "species" is defined as collection of closely related organisms with greater than 97% 16S ribosomal RNA sequence homology and greater than 70% genomic hybridization and sufficiently different from all other organisms so as to be recognized as a distinct unit (e.g., an operational taxonomic unit).

The term "strain" as used herein in reference to a microorganism describes an isolate of a microorganism considered to be of the same species but with a unique genome and, if nucleotide changes are non-synonymous, a unique proteome differing from other strains of the same organism. Strains may differ in their non-chromosomal genetic complement. Typically, strains are the result of isolation from a different host or at a different location and time, but multiple strains of the same organism may be isolated from the same host.

As used herein, the term "microbiota" refers to an assemblage of microorganisms localized to a distinct environment. Microbiota may include, for example, populations of various bacteria, eukaryotes (e.g., fungi), and/or archaea that inhabit a particular environment. For example, "gut microbiota," "vaginal microbiota," and "oral microbiota" refer to an assemblage of one or more species of microorganisms that are localized to, or found in, the gut, vagina, or mouth, respectively.

"Normal microbiota" refers to a population of microorganisms that localize in a particular environment in a normal, non-pathological state (e.g., a sample of gut microbiota from a subject without sepsis). A "normal microbiota" has normal membership and normal relative abundance.

"Abnormal microbiota" refers to a population of various microorganisms that localize in a particular environment in a subject suffering from or at risk of a pathological condition (e.g., a sample of gut microbiota from a subject with sepsis). Abnormal microbiota differs from normal microbiota in terms of identity (e.g., membership), absolute amount, or relative amount (e.g., relative abundance) of the various microbes.

As used herein, the term "commensal microbe" refers to a microorganism that is non-pathogenic to a host and is part of the normal microbiota of the host.

As used herein, the term "relative abundance" relates to the abundance of microorganisms of a particular taxonomic unit or OTU in a test biological sample compared to the abundance of microorganisms of the corresponding taxonomic unit or OTU in one or more non-diseased control samples. The "relative abundance" may be reflected in e.g., the number of isolated species corresponding to a taxonomic unit or OTU or the degree to which a biomarker specific for the taxonomic unit or OTU is present or expressed in a given sample. The relative abundance of a particular taxonomic unit or OTU in a sample can be determined using culture-based methods or non-culture-based methods well known in the art. Non-culture based methods include sequence analysis of amplified polynucleotides specific for a taxonomic unit or OTU or a comparison of proteomics-based profiles in a sample reflecting the number and degree of polypeptide-based, lipid-based, polyssacharide-based or carbohydrate-based biomarkers characteristic of one or more taxonomic units or OTUs present in the samples. Relative abundance or abundance of a taxon or OTU can be calculated with reference to all taxa/OTUs detected, or with reference to some set of invariant taxa/OTUs.

Methods for profiling the relative abundances of microbial taxa in biological samples, including biological samples of gut microbiota, are well known in the art. Suitable methods may be sequencing-based or array-based. For example, the microbial component of a gut microbiota sample is characterized by sequencing a nucleic acid suitable for taxonomic classification and assigning the sequencing reads to operational taxonomic units (OTUs) with a defined (e.g., >97%) nucleotide sequence identity to a database of annotated and representative sequences. An example of such a database is Greengenes version of May 2013; however, any suitable database may be used. After OTUs are defined, a representative sequence from each OTU can be selected and compared to a reference set. If a match is identified in the reference set, that OTU can be given an identity. Relative abundance of a bacterial taxon may be defined by the number of sequencing reads that can be unambiguously assigned to each taxon after adjusting for genome uniqueness. Other methods of profiling the relative abundances of microbial taxa in biological samples are known within the field and within the scope herein.

In some embodiments, a suitable nucleic acid for taxonomic classification is universally distributed among the gut microbial population being queried allowing for the analysis of phylogenetic relationships among distant taxa, and has both a conserved region and at least one region subject to variation. The presence of at least one variable region allows sufficient diversification to provide a tool for classification, while the presence of conserved regions enables the design of suitable primers for amplification (if needed) and/or probes for hybridization for various taxa at different taxonomic levels ranging from individual strains to whole phyla. While any suitable nucleic acid known in the art may be used, one skilled in the art will appreciate that selection of a nucleic acid or region of a nucleic acid to amplify may differ by environment. In some embodiments, a nucleic acid queried is a small subunit ribosomal RNA gene. For bacterial and archaeal populations, at least the V1, V2, V3, V4, V5, V6, V7, V8, and/or V9 regions of the 16S rRNA gene are suitable, though other suitable regions are known in the art. Guidance for selecting a suitable 16S rRNA region to amplify can be found throughout the art, including Guo et al. PLOS One 8 (10) e76185, 2013; Soergel D A W et al. ISME Journal 6:1440, 2012; and Hamady M et al. Genome Res. 19:1 141, 2009, each hereby incorporated by reference in its entirety.

DETAILED DESCRIPTION

Provided herein are compositions comprising lipotechoic acid (LTA) and methods of use thereof for immune modulation. In particular, compositions comprising *S. epidermidis* lipotechoic Acid (SELTA) are provided, as well as method of use thereof for the treatment of immune—(e.g., autoimmune) and inflammation-related conditions and diseases (e.g., chronic pelvic pain syndrome (CPPS), arthritis, etc.).

CPPS, for example, is a debilitating syndrome with a wide range of symptoms, the severity of which varies significantly between patients. Lack of understanding of the complex etiology of the disorder has hampered effective treatment development. The data presented herein describe the use of a commensal bacterial strain, or compositions (e.g., LTA) derived therefrom, to ameliorate tactile allodynia in an autoimmune murine model of CPPS. These data indicate that the bacterial flora of the prostate facilitate resetting of the immune milieu of diseased prostates and thus counteract EAP induced tactile allodynia responses. Additionally, these data indicate that in some embodiments, the commensal bacterial strains described herein, or compositions (e.g., LTA) derived therefrom, find use in the treatment of a variety immune—(e.g., autoimmune) and inflammation-related conditions and diseases.

Aged male NOD mice develop spontaneous prostatitis with incidences matching the pancreatitis observed in female mice (40-60%) (refs. 10,18,34; incorporated by reference in their entireties). Induction of prostatitis can be hastened in these mice by intraurethral infection with a specific strain of E. coli isolated from human EPS (CP-1 model) (ref. 37; incorporated by reference in its entirety). Increases in CD4+ve T-cell derived IL17A is necessary for initiation of pelvic tactile allodynia in the EAP murine model (refs. 32,39; incorporated by reference in its entirety). Analysis of human EPS samples demonstrated that IL7, a cytokine involved in maintenance of activated CD4 T-cells (ref. 25; incorporated by reference in its entirety) is increased in CPPS patients and correlated with pain severity. Development of tactile allodynia responses in the CP-1 infection model is dependent on host genetic background and specific to certain bacterial strains (refs. 37-38; incorporated by reference in their entireties). Compared to C57BL/6 mice, NOD mice are susceptible to induction of tactile allodynia by CP1 (refs. 37-38; incorporated by reference in their entireties). NOD mice develop spontaneous prostatitis with age (refs. 8,10, 18; incorporated by reference in their entireties). Data presented here demonstrated that NPI instillation does not induce referred allodynia in this background. Furthermore, it did not show increases in expression of CD4 T-cell markers associated with activation of Th1, Th2, or Th17 immune responses that are associated with CP1 instillation. These data demonstrate the commensal properties of the NPI strain, indicating that the local immune response can tolerate chronic colonization with the bacteria, even in a susceptible mouse background.

The EAP autoimmune model of CPPS induces tactile allodynia in NOD and C57BL/6 mice which is mediated, at least in part, by increases in levels of CD4+ve T-cells expressing IL17 (ref. 25; incorporated by reference in its entirety). Installation of NPI into C57BL/6 mice with EAP reverses both tactile allodynia responses and associated increases in IL17 expressing cells at the level of the prostate and iliac lymph nodes. The effect of bacterial instillation on referred allodynia was detectable as early as one-day post treatment and remained for seven days. Modulation of T-cell immunity was concomitant with reduction in tactile allodynia. S. epidermidis species have been shown to prevent super-infection (ref. 1; incorporated by reference in its entirety) of the skin via modulation of the local innate immune response (ref. 2; incorporated by reference in its entirety) and additional studies have focused on the direct interaction between bacteria and neurons (refs. 6,22; incorporated by reference in its entirety). These indicate that bacterial components can directly interact with neural pathways to influence pain in acute infection, in the absence of classical pathogen-associated molecular pattern (PAMP) activation (refs. 6,22; incorporated by reference in its entirety). Reduction of IL17 alone in the EAP model is ineffective at reducing tactile allodynia response (ref. 25; incorporated by reference in its entirety).

Numerous studies that have detected bacteria and bacterial components in EPS and post-prostate massage voided bladder samples of patients (refs. 4,13,19,28,46; incorporated by reference in their entireties). The exact nature of this flora, whether it is transient or permanent and its role in diseases of the male urogenital tract has not been previously evaluated. Experiments conducted during development of embodiments herein demonstrate that the effects of NPI instillation are highly specific compared to another S. epidermidis strain isolated from a patient with CPPS. This bacterium, designated 7244, showed no capacity to reduce tactile allodynia in EAP treated C57BL/6 mice but could colonize the prostate as effectively as NPI. Infection with 7244 did not increase referred pain responses above EAP induced levels.

The LTA component of the gram-positive cell wall is highly immunogenic and has been shown to activate members of the TLR family of receptors (refs. 16,20,29,33,36; incorporated by reference in their entireties). Experiments conducted during development of embodiments herein demonstrate the specificity of SELTA to reduce tactile allodynia compared to SALTA and BSLTA. This effect may dependent on differences in superstructure of the various LTA, which have been shown to vary significantly between bacterial strains resulting in unique downstream signaling effects and receptor utilization (ref. 20; incorporated by reference in its entirety); although embodiments herein are not limited to any particular mechanism of action and an understanding of the mechanism of action is not necessary to practice such embodiments. SELTA increases expression of the CTLA-4-like ligands PDL1 and PDL2 on the surface of CD11b+ve monocytes.

IL10 secretion and FoxP3 expressing T-regulatory cells have been shown in multiple studies and disease models to dampen the effects of CD4+ve IL17 expressing activated T-cells (refs. 15,17,23-24,40,50; incorporated by reference in their entireties). Experiments conducted during development of embodiments herein demonstrate that IL10 is necessary for the effect of NPI instillation on tactile allodynia, using IL10 knockout mice, correlates neatly with the observed decreases of IL17 in these mice. Blockade of either CD25 (used here as a surrogate marker for T-regulatory cells) or the PD1 receptor, by antibody treatment, prevents SELTAs amelioration of the tactile allodynia induced by EAP. This data further indicates PD1-PDL1/2 pathway involvement SELTA activity, while also further implicating the role of T-regulatory cells in mediating these effects.

Experiments conducted during development of embodiments herein demonstrate the capacity of a commensal bacteria (e.g., S. epidermidis, specific strains thereof (e.g., NPI), taxonomically-related bacteria, and/or bacteria with similar LTA characteristics) and cell wall components thereof (e.g., LTA) to reduce referred allodynia in a murine model of CPPS. Experiments conducted during development of embodiments herein demonstrate not only the specificity of bacterial isolates from the human prostate in modulating behavioral and immune responses but highlight also the role of the host immune response in these effects.

Experiments conducted during development of embodiments herein indicated that certain strains and species of bacteria, for example, Staphylococcus epidermidis, and strains thereof, for example, the NPI strain, are useful for modulating host immune responses and for treating/preventing immune-related and/or inflammation-related diseases and conditions in a subject.

Experiments conducted during development of embodiments herein demonstrate the capacity of a LTA (or a commensal bacteria that produces LTA (e.g., S. epidermidis, specific strains thereof (e.g., NPI), taxonomically-related bacteria, and/or bacteria with similar LTA characteristics) or cell wall components thereof (e.g., LTA)) to reduce referred allodynia and arthritis in a murine collagen induced arthritis (CIA) model (e.g., an accepted model of rheumatoid arthritis).

Experiments conducted during development of embodiments herein indicated that certain strains and species of bacteria, for example, *Staphylococcus epidermidis*, and strains thereof, for example, the NPI strain, are useful for modulating host immune responses and for treating/preventing immune-related and/or inflammation-related diseases and conditions in a subject.

In some embodiments, an immune response (e.g., autoimmune response, etc.) is dependent upon conditions (e.g. local conditions (e.g., organ or tissue specific conditions), systemic conditions) within the subject (e.g., microbiota). In particular, the identity or characteristics (e.g., concentration or level) of the microflora within a subject affects a subject's own immune response. In some embodiments, the presence or level of one or more microbes (e.g., *S. epidermidis*, specific strains thereof (e.g., NPI), taxonomically-related bacteria, and/or bacteria with similar LTA characteristics) in a subject modulates immune response. In some embodiments, the absence or a decreased level of one or more microbes (e.g., *S. epidermidis*, specific strains thereof (e.g., NPI), taxonomically-related bacteria, and/or bacteria with similar LTA characteristics) in a subject results in increased immune response (e.g., autoimmune response). In some embodiments, the absence and/or decreased level of one or more microbes (e.g., *S. epidermidis*, specific strains thereof (e.g., NPI), taxonomically-related bacteria, and/or bacteria with similar LTA characteristics) causes one or more diseases of medical conditions. In some embodiments, the presence or increased level of one or more microbes (e.g., *S. epidermidis*, specific strains thereof (e.g., NPI), taxonomically-related bacteria, and/or bacteria with similar LTA characteristics) in a subject promotes evasion of immune response (e.g., an autoimmune response, a detrimentally severe immune response, etc.). In some embodiments, the presence or increased level of one or more microbes (e.g., *S. epidermidis*, specific strains thereof (e.g., NPI), taxonomically-related bacteria, and/or bacteria with similar LTA characteristics) in a subject facilitates treatment of a disease or condition related to inflammation, immune response, and/or autoimmunity.

In some embodiments, the presence of beneficial microbes (e.g., *S. epidermidis*, specific strains thereof (e.g., NPI), taxonomically-related bacteria, and/or bacteria with similar LTA characteristics) in a subject (e.g., in a local environment within a subject) creates an environment or microenvironment (e.g., metabolome) that is conducive to the treatment of immune-related, autoimmune-related, and/or inflammation-related diseases and/or conditions. In some embodiments, the presence of detrimental microbes in a subject (e.g., in a local environment within a subject) creates an environment or microenvironment (e.g., metabolome) that is conducive to immune-related, autoimmune-related, and/or inflammation-related diseases and/or conditions and/or inhibits treatment thereof. In some embodiments, modulation of levels and/or identity of the microflora (e.g., reduce levels of detrimental microbes, increase levels of *S. epidermidis*, etc.) in a subject (e.g., in a local environment within a subject) facilitates treatment of immune-related, autoimmune-related, and/or inflammation-related diseases and/or conditions.

Modulation of microflora levels and/or identity may comprise encouraging or facilitating growth of one or more types of beneficial microbes (e.g., *S. epidermidis*, specific strains thereof (e.g., NPI), taxonomically-related bacteria, and/or bacteria with similar LTA characteristics), discouraging or inhibiting growth of one or more types of detrimental microbes (e.g., microbes that facilitate immune-related, autoimmune-related, and/or inflammation-related diseases and/or conditions), administering one or more types of beneficial microbes (e.g., *S. epidermidis*, specific strains thereof (e.g., NPI), taxonomically-related bacteria, and/or bacteria with similar LTA characteristics) to the subject, and/or combinations thereof. Embodiments within the scope herein are not limited by the mechanisms for introducing one or more microbes (e.g., fecal transplant, probiotic administration, etc.), encouraging growth of beneficial microbes (e.g., administering agents that skew the environment within the subject toward growth conditions for the beneficial microbes), discouraging or inhibiting growth of detrimental microbes (e.g., administering agents that skew the environment within the subject away from growth conditions for the detrimental microbes, administration of antimicrobial(s), etc.), and combinations thereof.

In some embodiments, methods are provided for the treatment or prevention of immune-related, autoimmune-related, and/or inflammation-related diseases by the manipulation of the presence, amount, or relative ratio of commensal microflora (e.g., increasing the absolute or relative amount of *S. epidermidis*, specific strains thereof (e.g., NPI), taxonomically-related bacteria, and/or bacteria with similar LTA characteristics). In some embodiments, the presence, amount, or relative ratio of *S. epidermidis*, specific strains thereof (e.g., NPI), taxonomically-related bacteria, and/or bacteria with similar LTA characteristics within a subject is manipulated.

In some embodiments, microflora-modulation utilizes prepared probiotic compositions for administration to/by a subject. Probiotic compositions comprise one or more beneficial microbes (e.g., *S. epidermidis*, specific strains thereof (e.g., NPI), taxonomically-related bacteria, and/or bacteria with similar LTA characteristics) formulated such that administration of the probiotic (e.g., orally, rectally, by inhalation, by injection, etc.) results in population of the subject by the beneficial microbes.

In some embodiments, probiotic compositions comprise cultured microbes (e.g., *S. epidermidis*, specific strains thereof (e.g., NPI), taxonomically-related bacteria, and/or bacteria with similar LTA characteristics) that are combined and/or formulated for administration to a subject. In some embodiments, probiotics contain microbes of known genera, species, etc. and/or at known concentrations (cfus). Probiotic compositions may be in the form of a pharmaceutical-type composition (e.g., capsule, tables, liquid, aerosol, etc.) or in the form of a food supplement.

In some embodiments, probiotic microbes (e.g., bacteria including *S. epidermidis*, specific strains thereof (e.g., NPI), taxonomically-related bacteria, and/or bacteria with similar LTA characteristics) are formulated in a pharmaceutically acceptable composition for delivery to a subject. In some embodiments, probiotics are formulated with a pharmaceutically acceptable carrier suitable for a solid or semi-solid formulation. In some embodiments, probiotic microbes are formulated with a pharmaceutically acceptable carrier suitable for a liquid or gel formulation. Probiotic formulations may be formulated for enteral delivery, e.g., oral delivery, or delivery as a suppository, but can also be formulated for parenteral delivery, e.g., vaginal delivery, inhalational delivery (e.g., oral delivery, nasal delivery, and intrapulmonary delivery), injection, and the like.

The probiotic compositions that find use in embodiments described herein may be formulated in a wide variety of oral administration dosage forms, with one or more pharmaceutically acceptable carriers. The pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is a mixture with the probiotic microbes. In tablets, the microbes are mixed with the carrier having the necessary binding capacity in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Other forms suitable for oral administration include liquid form preparations such as emulsions, syrups, elixirs, aqueous solutions, aqueous suspensions, or solid form preparations which are intended to be converted shortly before use to liquid form preparations. Aqueous suspensions can be prepared by dispersing the probiotic microbes in water with viscous material, such as natural or synthetic gums, resins, methylcellulose, sodium carboxymethylcellulose, and other well-known suspending agents.

The probiotic compositions (e.g., microbes (e.g., bacteria)) may be formulated for administration as suppositories. A low melting wax, such as a mixture of fatty acid glycerides or cocoa butter is first melted and the probiotic microbes are dispersed homogeneously, for example, by stirring. The molten homogeneous mixture is then poured into conveniently sized molds, allowed to cool, and to solidify.

The probiotic compositions (e.g., microbes (e.g., bacteria)) may be formulated for vaginal administration. Pessaries, tampons, creams, gels, pastes, foams or sprays, may contain agents in addition to the bacteria, such carriers, known in the art to be appropriate.

In some embodiments, probiotic compositions (e.g., microbes (e.g., bacteria)) may be formulated for delivery by inhalation. As used herein, the term "aerosol" is used in its conventional sense as referring to very fine liquid or solid particles carries by a propellant gas under pressure to a site of therapeutic application. The term "liquid formulation for delivery to respiratory tissue" and the like, as used herein, describe compositions comprising probiotic microbes with a pharmaceutically acceptable carrier in flowable liquid form. Such formulations, when used for delivery to a respiratory tissue, are generally solutions, e.g. aqueous solutions, ethanolic solutions, aqueous/ethanolic solutions, saline solutions and colloidal suspensions.

Rather than pharmaceutical-type formulation, probiotic compositions may be formulated as food additive and/or food product and incorporated into a variety of foods and beverages. Suitable foods and beverages include, but are not limited to, yogurts, ice creams, cheeses, baked products such as bread, biscuits and cakes, dairy and dairy substitute foods, soy-based food products, grain-based food products, starch-based food products, confectionery products, edible oil compositions, spreads, breakfast cereals, infant formulas, juices, power drinks, and the like.

In some embodiments, a probiotic composition is administered over a dosing time period (e.g., <1 minute, <1 hour, <2 hours, <4 hours, <6 hours, <12 hours, <24 hours, etc.) in an amount that is sufficient to provide a desired therapeutic benefit (e.g., as a single dose, in combination with other doses, in combination with a co-administered therapeutic, etc.) In some embodiments, the dose of the probiotic composition administered for the dosing time period is concentration of from about 10 to about $1 \times 10^{14}$ colony forming units (cfu) of the commensal microbial agent(s) (e.g., 10 cfu, 100 cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, or any suitable ranges therein (e.g., from about $10^2$ cfu to about $10^{13}$ cfu, about $1 \times 10^4$ to about $1 \times 10^{11}$ cfu, about $1 \times 10^6$ to about $1 \times 10^9$ cfu, about $1 \times 10^{10}$ to about $1 \times 10^{12}$ cf, etc.), etc.).

In some embodiments, the microbial make-up of a probiotic composition consists or consists essentially of one or more beneficial microbes (e.g., S. epidermidis, specific strains thereof (e.g., NPI), taxonomically-related bacteria, and/or bacteria with similar LTA characteristics). In some embodiments, the microbial make-up of a probiotic composition consists or consists essentially of 1, 2, 3, 4, 5, 6, 7, 8, 9, 10, 15, 20, 25, 30, 40, 50, 60, 70, 80, 90, 100, or any ranges therein (e.g., 1-4, 5-10, 8-20, etc.) strains and/or species of microbes. In some embodiments, fewer than 50 microbial strains (e.g., 1, 2, 3, 4, 5, 6, 7, 8, 9, 10, 15, 20, 25, 30, 40, 50, or any ranges therein (e.g., 1-4, 5-10, 8-20, etc.) are at least 50% (e.g., 50%, 60%, 70%, 80%, 85%, 90%, 91%, 92%, 93%, 94%, 95%, 96%, 97%, 98%, 99%, 99.5%. 99.9%, 99.99%) of the microbial population (e.g., by mass, by cfu, etc.) of a probiotic composition. For example, in some embodiments, a single species or strain of S. epidermidis, specific strains thereof (e.g., NPI), taxonomically-related bacteria, and/or bacteria with similar LTA characteristics is at least 95% of the microbial population, as measured by colony forming units, of a particular probiotic composition. As another example, in some embodiments, a single species or strain of S. epidermidis, specific strains thereof (e.g., NPI), taxonomically-related bacteria, and/or bacteria with similar LTA characteristics is at least 40% of the microbial population, as measured by mass, of a particular probiotic composition. These examples are not limiting.

In some embodiments, microflora in a subject (e.g., a subject suffering from an immune-related, autoimmune-related and/or inflammation-related disease) are modulated by transplantation of microbiota from a subject with favorable characteristics (e.g., a healthy subject) into the recipient subject. In some embodiments, donor microflora are obtained sampling microflora from the desired region of the donor subject body (e.g., colon, oral cavity, vagina, etc.). In particular embodiments, fecal material (e.g., 100 g-500 g) is obtained from a donor. The material may be administered to a recipient subject with or without subsequent preparation steps (e.g., diluting, mixing, oxygenating, filtering, supplementing (e.g., with prebiotics, with growth media, etc.), testing (e.g., for pathogens or detrimental microbes), etc.). The donor microflora (e.g., fecal material) may be administered without preservation (e.g., administered within 12 hours (e.g., <6 hours, <4 hours, <2 hours, <1 hour, etc.)) or may be preserved (e.g., frozen, freeze dried, etc.), for example, to allow for delay (e.g., 1 day, 2, days, 1 week, 1 month, or more) before delivery to the subject. In some embodiments, donor microflora are proceed to remove one or more components. For example, parasitic of detrimental microbes may be removed or killed. Contaminants within the donor sample may be removed. In some embodiments, donor microflora is enriched (e.g., 2-fold, 3-fold, 4 fold, 10-fold, 20-fold, or more enrichment) for one or more specific microbes (e.g., S. epidermidis, specific strains thereof (e.g., NPI), taxonomically-related bacteria, and/or bacteria with similar LTA characteristics). In some embodiments, donor microflora is enriched such that at least 1% (e.g., 1%, 2%, 3%, 4%, 5%, 6%, 7%, 8%, 9%, 10%, 15%, 20%, 25%, 30%, 40%, 50%, 60%, 70%, 80%, 90%, or more) of the microbes in the population are the desired beneficial microbes (e.g., S. epidermidis, specific strains thereof (e.g., NPI), taxonomically-related bacteria, and/or bacteria with similar LTA characteristics). In some embodiments, donor microflora are doped with one or more cultured beneficial microbes.

In particular embodiments, transplanted microflora may be administered to the recipient subject by any suitable delivery mechanism, including but not limited to enema, colonoscope, nasogastric or nasoduodenal tube, lavage or irrigation, or orally (e.g., in the form of a capsule).

In some embodiments, a commensal microbial agent or population of microbial agents is administered (e.g., via probiotic composition or microflora transplant) over a dosing time period (e.g., <1 minute, <1 hour, <2 hours, <4 hours, <6 hours, <12 hours, <24 hours, etc.) in an amount that is sufficient to provide a desired therapeutic benefit (e.g., as a single dose, in combination with other doses, in combination with a co-administered therapeutic, etc.) In some embodiments, the dose of commensal microbial agent(s) administered for the dosing time period is concentration of from about 10 to about $1 \times 10^{14}$ colony forming units (cfu) of the commensal microbial agent(s) (e.g., 10 cfu, 100 cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, or any suitable ranges therein (e.g., from about $10^2$ cfu to about $10^{13}$ cfu, about $1 \times 10^4$ to about $1 \times 10^{11}$ cfu, about $1 \times 10^6$ to about $1 \times 10^9$ cfu, about $1 \times 10^{10}$ to about $1 \times 10^{12}$ cf, etc.), etc.).

The dose can be administered in a single unit dose administered at any time during a day. Alternatively, the loading dose can be administered in two or more doses administered at a single time of day or at two or more separate times of day. Over the course of multiple dosing periods, the dose can be tapered from an initial dose to a higher dose (or increased from an initial dose to a higher dose), on predetermined timing or by the when the subject and/or clinician based on the results of the treatment. The appropriate dosage amount will vary by, for example, an individual subject's age, weight, condition or disease, severity of disease, etc.

In some embodiments, microbes (e.g., *S. epidermidis*, specific strains thereof (e.g., NPI), taxonomically-related bacteria, and/or bacteria with similar LTA characteristics) for probiotic compositions are obtained from culture. In some embodiments, strains of beneficial microbes are genetically engineered to enhance one or more of production (e.g., at scale), formulation, delivery, or the biological effect of the microbe. In some embodiments, microbes are engineered to express a detectable marker that allows tracking of the microbes within a subject, or confirmation that the microbe has integrated into a subject's microflora. In some embodiments, microbes are engineered to express therapeutic agents (e.g., anti-inflammatory agent or other drug).

In some embodiments, one or more prebiotics are administered to a subject as an independent treatment (e.g., to increase the level of *S. epidermidis*, specific strains thereof (e.g., NPI), taxonomically-related bacteria, and/or bacteria with similar LTA characteristics) or in conjunction with other treatments described herein. Prebiotics are agents that increase the in vivo growth rate or activity of commensal microbes, such as *S. epidermidis*, specific strains thereof (e.g., NPI), taxonomically-related bacteria, and/or bacteria with similar LTA characteristics. In some embodiments, prebiotics are soluble fiber sources. In some embodiments, when prebiotics are administered (e.g., fed) to a subject they are not digested or are not fully digested by the subject's digestive enzymes, but rather support the intestinal health of the subject and provide an energy source for the beneficial microbes and enhance the growth thereof. Prebiotics include, for example, naturally occurring lecithins and/or oleic acid, and are described, for example in U.S. Pat. No. 8,449,878 which is herein incorporated by reference in its entirety.

In some embodiments, the level or presence of one or more detrimental microbes (e.g., microbes that facilitate autoimmunity, inflammation, etc.) is modulated, for example, by the administration of one or more antimicrobial agents to a subject or modulation of conditions within the subject to disfavor growth of the detrimental microbes. In some embodiments, antimicrobial agents are administered.

In some embodiments, the antimicrobial agent is an antibiotic. Exemplary antibiotics that may find use in some embodiments include, but are not limited to: amikacin, gentamicin, kanamycin, neomycin, netilmicin, streptomycin, tobramycin, paromycin, geldanamycin, herbimycin, loracarbef, ertapenem, doripenem, imipenem, meropenem, cefaclor, cefamandole, cefotoxin, cefprozil, cefuroxime, cefixime, cefdinir, cefditoren, cefpodoxime, ceftazidime, ceftibuten, ceftizoxime, ceftriaxone, cefepime, ceftobirprole, vancomycin, azithromycin, clarithromycin, dirithromycin, erythromycin, roxithromycin, troleandomycin, telithromycin, spectinomycin, aztreonam, amoxicillin, ampicillin, azociling, carbenicillin, cloxacillin, dicloxacillin, flucloxacillin, mezlocillin, meticillin, nafcillin, oxacillin, peperacillin, ticarcillin, bacitracin, colistin, polymyxin B, ciprofloxacin, clavulanic acid, enoxacin, gatifloxacin, levofloxacin, lomefloxacin, moxifloxacin, nonfloxacin, ofloxacin, trovafloxacin, grepafloxacin, sparfloxacin, AL-15469A, AL-38905, OP-145, afenide, prontosil, sulfacetamide, sulfamethiazole, sulfanamide, sulfasalazine, sulfisoxazole, trimethoprim, cotrimoxazole, demeclocycline, doxycycline, minocycline, oxytetracycline, tetraycline, linezolid, arsogebanubem chloramphenicol, clindamycin, lincomycin, ethambutol, fosfomycin, fusidic acid, furazolidone, isoniazid, linezolid, metronidazole, mupirocin, nitrofurantoin, rifampicin, thamphenicol, tinidazole, amoxicillin+clavulanic acid, Maximin H5, Dermcidin, Cecropins, andropin, moricin, ceratotoxin, melittin, Magainin, dermaseptin, bombinin, brevinin-1,esculentins and buforin II, CAP 18, LL37, abaecin, apidaecins, prophenin, indolicidin, brevinins, protegrin, tachyplesins, defensins, drosomycin, alamethicin, pexiganan or MSI-78, MSI-843, MSI-594, polyphemusin, colicin, pyocin, klebicin, subtilin, epidermin, herbicolacin, brevicin, halocin, agrocin, alveicin, carnocin, curvaticin, divercin,enterocin, enterolysin, erwiniocin, glycinecin, lactococin, lacticin, leucoccin, mesentericin, pediocin, plantaricin, sakacin, sulfolobicin, vibriocin, warnerinand, nisin, or a salt or cocrystal, or prodrug or solvate thereof, or a combination thereof.

In some embodiments, the antimicrobial is an antifungal agent. Exemplary antifungals that may find use in some embodiments include, but are not limited to: amrolfine, utenafine, naftifine, terbinafine, flucytosine, fluconazole, itraconazole, ketoconazole, posaconazole, ravuconazole, voriconazole, clotrimazole, econazole, miconazole, oxiconazole, sulconazole, terconazole, tioconazole, nikkomycin Z, caspofungin, micafungin, anidulafungin, amphotericin B, liposomal nystastin, pimaricin, griseofulvin, ciclopirox olamine, haloprogin, tolnaftate, undecylenate, clioquinol, and combinations thereof.

In some embodiments, the antimicrobial is an antiparasitic. Exemplary antiparasitics that may find use in some embodiments include, but are not limited to: amitraz, amoscanate, avermectin, carbadox, diethylcarbamizine, dimetridazole, diminazene, ivermectin, macrofilaricide, malathion, mitaban, oxamniquine, permethrin, praziquantel, prantel pamoate, selamectin, sodium stibogluconate, thiabendazole, and combinations thereof.

In some embodiments, methods and compositions for reduction of detrimental microbe levels are co-administered (e.g., serially, concurrently, etc.) with methods and compositions for increasing beneficial microbe levels. In some embodiments, by reducing overall microbe levels or by reducing the levels of specific microbes (e.g., detrimental microbes, high population microbes, etc.), the population of beneficial microbes can more effectively be modulated (e.g., increased).

In some embodiments, in order to develop a microflora population within a subject that inhibits inflammation/autoimmunity and/or facilitates treatment of inflammation/autoimmunity, antimicrobial agents are first administered to eliminate or reduce the microflora within the subject, and then the microflora population is reestablished using the methods and compositions described herein (e.g., administration of beneficial microbes (e.g., S. epidermidis, specific strains thereof (e.g., NPI), taxonomically-related bacteria, and/or bacteria with similar LTA characteristics). In some embodiments, antimicrobials (e.g., antibiotics) that reduce the microbe (e.g., bacteria) population generally are employed. In some embodiments, antimicrobials that target detrimental microbes preferentially are employed.

In certain embodiments, microflora composition is manipulated along with one or more other therapies (e.g., anti-inflammatory therapies, treatment of autoimmune disease, etc.). In some embodiments, manipulation of the microflora composition (e.g., identity and/or level) treats inflammation/autoimmunity by a mechanism independent of one or more additional therapeutics. In other embodiments, modulation of microflora composition facilitates (e.g., increases the effectiveness of) co-administered therapeutics/therapies. In some embodiments, one or more therapeutics/therapies enhance the effectiveness of the modulation of microflora composition. Embodiments herein are not limited by the types of additional therapeutics/therapies unless specifically noted.

Experiments conducted during development of embodiments herein indicated that certain compositions comprising lipoteichoic acid (LTA), for example, LTA derived from the cell will of *Staphylococcus epidermidis*, LTA derived from certain strains thereof (e.g., the NPI strain), and/or LTA comprising similar or the same structural/functional characteristics as the aforementioned are useful for modulating host immune responses and for treating/preventing immune-related and/or inflammation-related diseases and conditions in a subject.

Lipoteichoic acid (LTA) is a major constituent of the cell wall of gram-positive bacteria. The structure of LTA varies between the different species of Gram positive bacteria. LTA comprises an oligomer of glycerophosphates linked to a glycolipid anchor by a disaccharide. The LTA is anchored to the cell membrane via a diacylglycerol. In some embodiments, LTA comprises formula I:

(Formula I)

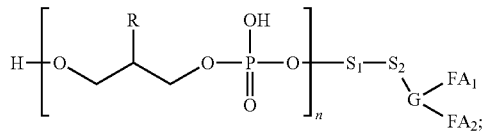

wherein n is 2-100 (e.g., 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or ranges therebetween; wherein each R is any suitable amino acid (e.g., D-alanine), saccharide (e.g., N-acetylglucosamine, glucose, galactose, etc.), or H; wherein $S_1$ and $S_2$ are monosaccharides (e.g., D-glucose, fructose, mannose, galactose, glucosamine, xylopyranose, rhamnose, etc.) connected by any suitable linker (e.g., $\alpha(1\rightarrow2)$, $\alpha(1\rightarrow3)$, $\alpha(1\rightarrow6)$, $\beta(1\rightarrow2)\beta$, $\beta(1\rightarrow2)$, $\beta(1\rightarrow3)$, $\beta(1\rightarrow6)$, etc.), wherein G is a glyceride moiety and $FA_1$ and $FA_2$ are fatty acids (e.g., saturated or unsaturated) of any suitable length (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, or ranges therebetween). In some embodiments, LTA of Formula I is administered to a subject.

In some embodiments, saccharides of the LTA described herein (e.g., R, $S_1$ and $S_2$ groups) are monosaccharides. In some embodiments, monosaccharides comprise include trioses, such as glycerose and dihydroxyacetone; textroses such as erythrose and erythrulose; pentoses, such as xylose, arabinose, ribose, xylulose ribulose; methyl pentoses (6-deoxyhexoses), such as rhamnose and fucose; hexoses, such as ascarylose, glucose, mannose, galactose, fructose, and sorbose; and heptoses, such as glucoheptose, galamannoheptose, sedoheptulose, and mannoheptulose. Exemplary monosaccharides embrace radicals of allose, altrose, arabinose, cladinose, erythrose, erythrulose, fructose, D-fucitol, L-fucitol, fucosamine, fucose, fuculose, galactosamine, D-galactosaminitol, N-acetyl-galactosamine, galactose, glucosamine, N-acetyl-glucosamine, glucosaminitol, glucose, glucose-6-phosphate, gulose glyceraldehyde, L-glycero-D-mannos-heptose, glycerol, glycerone, gulose, idose, lyxose, mannosamine, mannose, mannose-6-phosphate, psicose, quinovose, quinovasamine, rhamnitol, rhamnosamine, rhamnose, ribose, ribulose, sedoheptulose, sorbose, tagatose, talose, tartaric acid, threose, xylose, and xylulose. The monosaccharide can be in D- or L-configuration.

In some embodiments, $S_1$ and $S_2$ are present in an LTA as a disaccharide. Exemplary disaccharides present in the LTA herein include: sucrose, lactulose, lactose, maltose, trehalose, cellobiose, chitobiose, kojibiose, nigerose, isomaltose, $\beta,\beta$-trehalose, $\alpha,\beta$-trehalose, sophorose, laminaribiose, gentiobiose, turanose, maltulose, palatinose, gentiobiulose, mannobiose, melibiose, melibiulose, rutinose, rutinulose, and xylobiose. In particular embodiments, $S_1$ and $S_2$ are present in an LTA as gentiobiose.

In some embodiments, R of Formula I is any suitable natural amino acid, unnatural amino acid, or amino acid analog. In some embodiments, the amino acid may be present in the D or L stereoisomer, unless otherwise indicated, if their structures allow such stereoisomeric forms. Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V). Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg"). Amino acid analogs include to a natural or unnatural amino acid where one or more of the C-terminal carboxy group, the N-terminal amino group and side-chain functional group has been chemically blocked, reversibly or irreversibly, or otherwise modified to another functional group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

In some embodiments, $FA_1$ and $FA_2$ of Formula I are any suitable fatty acid. For example, $FA_1$ and $FA_2$ independently comprise carboxylic acids with long aliphatic chains, which are either saturated or unsaturated. Examples of fatty acids that find use in embodiments herein, include:

make-up of natural *S. epidermidis* LTA, and/or (ii) elicits the immune-modulatory/anti-inflammatory effects of *S. epidermidis* LTA.

In some embodiments, the compositions and methods herein find use the treatment, prevention, and/or symptom reduction of diseases related to autoimmunity, inflammation, improper immune response, and/or pain. Autoimmune diseases are those which are characterized as having a component of self-recognition. Examples of autoimmune diseases include, but are not limited to, autoimmune hepatitis, multiple sclerosis, systemic lupus erythematosus, myasthenia gravis, type i diabetes, rheumatoid arthritis, psoriasis, hashimoto's thyroiditis, grave's disease, ankylosing spondylitis sjogrens disease, CREST syndrome, scleroderma, etc. Most autoimmune diseases are also chronic inflammatory diseases. This is defined as a disease process associated with long-term (>6 months) activation of inflammatory cells (e.g., leukocytes). The chronic inflammation leads to damage of patient organs or tissues. Many other diseases are inflammatory disorders, but are not necessarily known to have an autoimmune basis. For example, chronic pelvic pain syndrome, atherosclerosis, congestive heart failure, Crohn's disease, ulcerative colitis, polyarteritis nodosa, Whipple's Disease, Primary Sclerosing Cholangitis, etc. The clinical manifestations of autoimmune and inflammatory diseases range from mild to severe. Mild disease encompasses symptoms that may be function-altering and/or comfort-altering, but are neither immediately organ-threatening nor life-

| Common Name | Chemical Structure | C:D |
|---|---|---|
| Myristoleic acid | $CH_3(CH_2)_3CH=CH(CH_2)_7COOH$ | 14:1 |
| Palmitoleic acid | $CH_3(CH_2)_5CH=CH(CH_2)_7COOH$ | 16:1 |
| Sapienic acid | $CH_3(CH_2)_8CH=CH(CH_2)_4COOH$ | 16:1 |
| Oleic acid | $CH_3(CH_2)_7CH=CH(CH_2)_7COOH$ | 18:1 |
| Elaidic acid | $CH_3(CH_2)_7CH=CH(CH_2)_7COOH$ | 18:1 |
| Vaccenic acid | $CH_3(CH_2)_5CH=CH(CH_2)_9COOH$ | 18:1 |
| Linoleic acid | $CH_3(CH_2)_4CH=CHCH_2CH=CH(CH_2)_7COOH$ | 18:2 |
| Linoelaidic acid | $CH_3(CH_2)_4CH=CHCH_2CH=CH(CH_2)_7COOH$ | 18:2 |
| α-Linolenic acid | $CH_3(CH_2)CH=CHCH_2CH=CHCH_2CH=CH(CH_2)_7COOH$ | 18:3 |
| Arachidonic acid | $CH_3(CH_2)CH=CHCH_2CH=CHCH_2CH=CH(CH_2)_3COOH^{NIST}$ | 20:4 |
| Eicosapentaenoic acid | $CH_3(CH_2)CH=CHCH_2CH=CHCH_2CH=CHCH_2CH=CH(CH_2)_3COOH^{NIST}$ | 20:5 |
| Erucic acid | $CH_3(CH_2)_7CH=CH(CH_2)_{11}COOH$ | 22:1 |
| Docosahexaenoic acid | $CH_3(CH_2)CH=CHCH_2CH=CHCH_2CH=CHCH_2CH=CHCH_2CH=CH(CH_2)COOH$ | 22:6 |
| Caprylic acid | $CH_3(CH_2)_6COOH$ | 8:0 |
| Capric acid | $CH_3(CH_2)_8COOH$ | 10:0 |
| Lauric acid | $CH_3(CH_2)_{10}COOH$ | 12:0 |
| Myristic acid | $CH_3(CH_2)_{12}COOH$ | 14:0 |
| Palmitic acid | $CH_3(CH_2)_{14}COOH$ | 16:0 |
| Stearic acid | $CH_3(CH_2)_{16}COOH$ | 18:0 |
| Arachidic acid | $CH_3(CH_2)_{18}COOH$ | 20:0 |
| Behenic acid | $CH_3(CH_2)_{20}COOH$ | 22:0 |
| Lignoceric acid | $CH_3(CH_2)_{22}COOH$ | 24:0 |
| Cerotic acid | $CH_3(CH_2)_{24}COOH$ | 26:0 |

In some embodiments, LTA comprises the chemical make-up (e.g., one or more species comprising specific chemical formulas or chemical genera (e.g., in appropriate ratios), etc.) of the LTA of *S. epidermidis*. In some embodiments, LTA is prepared from *S. epidermidis* (e.g., a culture of *S. epidermidis*). In other embodiments, an LTA composition is prepared (e.g., synthetically), to match the natural make-up of LTA obtained from *S. epidermidis* (e.g., or sufficiently similar thereto to elicit a beneficial effect when administered to a subject). In some embodiments, an LTA composition comprises one or more LTA chemical species. In some embodiments, an LTa composition comprises two or more LTA species present in a ration that (i) simulates the threatening. Severe disease entails organ-threatening and/or life-threatening symptoms. For example, severe autoimmune disease is often associated with clinical manifestations such as nephritis, vasculitis, central nervous system disease, premature atherosclerosis or lung disease, or combinations thereof, which require aggressive treatment and may be associated with premature death. In some embodiments, the compositions and methods described herein find use in treatment, prevention (when applicable), and/or symptom reduction of the aforementioned diseases and conditions.

In some embodiments, compositions and methods herein comprise multiple modes for modulating host immune responses and for treating/preventing immune-related and/or inflammation-related diseases and conditions in a subject. In some embodiments, the treatments described herein are co-administered with prebiotics and/or other agents that facilitate the growth of the beneficial microbes. In some embodiments, beneficial microbes are provided/administered (e.g., by a probiotic composition, fecal transplant, etc.) with antimicrobial(s) (e.g., antibiotics) directed to kill or inhibit the growth of detrimental microbes. In some embodiments, prebiotics and/or other agents that facilitate the growth of the beneficial microbes are provided/administered with antimicrobial(s) (e.g., antibiotics) directed to kill or inhibit the growth of detrimental microbes. In some embodiments, beneficial microbes, prebiotics and/or other agents that facilitate the growth of the beneficial microbes, and an antimicrobial(s) (e.g., antibiotics) directed to kill or inhibit the growth of detrimental microbes are all co-administered. In some embodiments, LTA is administered with one or more agents that further treat inflammation and/or the diseases/conditions caused by or underlying the inflammation.

In some embodiments, the co-administered agents are formulated into a single dose and/or composition. In some embodiments, the co-administered agents are in separate doses and/or compositions. In some embodiments in which separate doses and/or compositions are administered, the doses and/or compositions are administered simultaneously, consecutively, or spaced over a time span (e.g., <30 minutes, 1 hour, 2 hours, 4 hours, 6 hours, 12 hours, 1 day, 2 days, 3 days, 4 days, 5 days, 6 days, 1 week, or more, or any suitable ranges therebetween).

In some embodiments, compositions described herein are co-administered with one or more therapeutics useful for the treatment of rheumatoid arthritis, such as disease-modifying antirheumatic drugs (DMARDs) (e.g., methotrexate, hydroxychloroquine, sulfasalazine, leflunomide, TNF-alpha inhibitors (e.g., certolizumab, infliximab and etanercept), abatacept, anakinra, rituximab, tocilizumab, etc.), anti-inflammatory and analgesic agents (e.g., Glucocorticoids, non-NSAID drugs to relieve pain (e.g., paracetamol), NSAIDs, etc.

In some embodiments, compositions described herein are co-administered with one or more therapeutics useful for the treatment of CPPS, such as alpha blockers (e.g., tamsulosin, alfuzosin, etc.), antibiotics (e.g., fluoroquinolones, tetracyclines, macrolides, etc.), NSAIDS, estrogen reabsorption inhibitors (e.g., mepartricin, etc.), etc.

EXPERIMENTAL

Example 1

Additional description of the experiments and results of Example 1 are described in Murphy et al. (2017), which is herein incorporated by reference in its entirety.

Materials and Methods

Animal Use

Male 5-7 week old C57BL/6 (B6), NOD/ShiLtJ (NOD) and B6.129P2-Il10$^{tm1Ggn}$ (IL10KO) mice were purchased from Jackson Laboratory (Bar Harbor, ME). All comparisons were made directly between genetically identical commercially obtained animals. Experiments were conducted in male mice, as the disease condition being studied is restricted to men. EAP was induced in specific mice by subcutaneous injection of rat prostate homogenate at a 1:1 ratio with TITERMAX adjuvant. Following this injection referred pain responses were measured by Von Frey force filament behavioral testing for tactile allodynia, as described (ref. 15; incorporated by reference in its entirety). Testing was performed prior to EAP induction (baseline) and then every 7 days unless otherwise stated. Results were calculated as a percentage change above baseline and for each Von Frey filament of increasing force per group individually, values were averaged across experimental groups. Behavioral testing was performed following treatments (with bacteria or LTA) in a blinded manner with no knowledge of treated versus untreated groups. After 28 days of EAP (unless otherwise stated) mice were sacrificed and relevant tissues removed. Prostate and bladder tissues were dissociated using collagenase/DNase buffer (1640-RPMI (Corning) containing 10% FCS (Hyclone), 0.1 ul/ml DNase (Thermo-scientific) and 1 ug/ml collagenase D (Roche)) and shaking for 2 hours at 37° C. Tissues were then made into single cell suspensions by passing through 0.2 μm mesh filter membranes and washing with 2% FCS (HyClone) in PBS (Gibco). For splenic and iliac lymph node tissues, single cell suspensions were generated without collagenase treatment.

Bacterial Isolation, Growth and Instillation

Human expressed prostatic secretion (EPS) and voided bladder 1, 2 and 3 samples were collected from the urology clinic at Northwestern Memorial Hospital. *S. epidermidis* was isolated from both the VB3 (post-massage urine) and EPS of a healthy control sample. The bacterial isolate was grown in Luria Broth, as previously described for UPEC strains (ref. 13; incorporated by reference in its entirety). Bacteria were grown in 3 ml at 37° C. overnight followed by transfer of 100 μl of this culture to 40 ml and growing for 37° C. without shaking. Following this bacterial was pelleted and re-suspended in ice cold sterile PBS, the solution was then made up to an OD 420 value of 1.00, corresponding to 2×10^10 bacteria per ml. 10 μl of the NPI strain preparation was introduced into anesthetized male mice by catheterization. This correlates with 2×10^8 bacteria per infection per mouse.

LTA Isolation and Treatment

The NPI strain was shipped on dry ice to a commercial biofermentation lab (University of Maryland, Rockville, MD) followed by purification by HPLC at FinoBiolabs (Rockville MD). Purified LTA was returned (3.011 mg from a 10L culture) as a desiccated powder. This was reconstituted using DNA grade water (Gibco) and stored at 1 mg/ml at −80° C., until use. 10 μl of a 1:100 dilution of this solution (100 ng) was used per mouse per treatment, this was calculated based on an estimation of the LTA content of the dry weight of the 2×10^8 bacteria normally used in infections. *S. aureus* and *B. subtilis* LTA were purchased from Invivogen and equal doses were administered as above. Mice were treated by intraurethral instillation under anesthesia in a similar manner to the infection protocol.

In Vivo Antibody Treatment

Blockade of CD25 and PD1 was performed, therapeutically; by intraperitoneal injection with 100 μg anti-CD25 (PC61) (BioLegend 102002) or 100 μg anti-PD1 (BxCell BE0146) or relevant IgG isotype control antibody at Day 19 post-EAP treatment and repeated every two days with pain/tactile allodynia assessed every alternate day until Day 28.

QRTPCR

RNA isolation was performed from respective tissues (collagenase treated prostate and bladder homogenates) using Trizol™ (Invitrogen). RNA concentration was measured using a NANODROP spectrophotometer (Thermo Scientific) and normalized to 1ug per cDNA synthesis reaction. cDNA was synthesized using qScript Supermix (Quanta) according to manufacturer instructions. QRTPCR was performed using perfeCTa qPCR Supermix (Quanta) with 50 ng of template per 25 µl reaction and run on the CFX CONNECT (Biorad) platform. Primers were designed using the online NIH curated primer blast tool. A full table of primer sequences is below. ddCT calculations were performed in EXCEL, mouse genes were normalized first against the L19 housekeeping gene and finally by expression of CD4, human genes normalized to GAPDH and both analyzed using GraphPad PRISM software.

Mouse Sequences

| Gene | Forward | SEQ ID NO: | Reverse | SEQ ID NO: |
|---|---|---|---|---|
| L19 | CAACTCCCGCCAGCAGAT | 1 | CCGGGAATGGACAGTCACA | 11 |
| CD4 | GCTCAAGGAGACCACCATGTG | 2 | GCGAAGGCGAACCTCCTC | 12 |
| Tbet | TGTTCCCAGCCGTTTCTACC | 3 | GCTCGGAACTCCGCTTCATA | 13 |
| IFNγ | ACACTGCATCTTGGCTTTGC | 4 | CTTTCAATGACTGTGCCGTGG | 14 |
| GATA3 | AAGCTCAGTATCCGCTGACG | 5 | GATACCTCTGCACCGTAGCC | 15 |
| IL4 | CCATATCCACGGATGCGACA | 6 | CGTTGCTGTGAGGACGTTTG | 16 |
| RorγT | AGGGCCTACAATGCCAACAA | 7 | CAGCTCCACACCACCGTATT | 17 |
| IL17A | TCTCCACCGCAATGAAGACC | 8 | TTTCCCTCCGCATTGACACA | 18 |
| FoxP3 | CACCCAGGAAAGACACAACC | 9 | GCAAGAGCTCTTGTCCATTGA | 19 |
| IL10 | AAGGGTTACTTGGGTTGCCA | 10 | CCTGGGGCATCACTTCTACC | 20 |

Flow Cytometry Analyses.

Flow cytometry was performed on single cell suspensions using mouse antibodies: PerCp-CD4, ALEXA™ 488-CD4, ALEXA™ 488-647-FoxP3, PE-IL17A, FITC-CD25, PE-PD1 (Biolegend), PE-FoxP3, PC-IL17, FITC-CD25, APC-CD11b, FITC-PDL2, PE-PDL1 (eBiosciences). Flow was run on an Accuri benchtop C6 cytometer and analysed using FLOWJO software. Unless otherwise stated, samples were gated on lymphocyte populations based on size, as assessed by SSC and FSC, followed by gating for CD4 positivity. Intracellular staining was performed by fixation and permeabilization using eBioscience Fix-Perm Intracellular staining buffers (Cat. Num 8222-49 and 8333-56). Staining was performed for 1 hour at room temperature followed by washing in FACS buffer (2% FCS (Hyclone), in PBS (Gibco)) Analyses were performed using FLOWJO and data statistically tested using GraphPad PRISM software, with tests described in respective figure legends.

Immunofluorescent Staining

10% formalin-fixed tissues were mounted and embedded in paraffin and sectioned (5 µm) onto slides. These were then rehydrated in xylene (VWR), followed by increasing dilutions in ethanol (100%, 75%, 50% and 25%). Antigen retrieval was performed by boiling for 25 mins in 10 mM Sodium Citrate Buffer at a of pH 6.0, sections were then transferred to PBS (Gibco), excess liquid removed and staining performed using rabbit anti-mouse PDL1 antibody (AbCam ab58810) or PDL2 antibody (AbCam ab21239). Secondary staining with ALEXA™ 488-anti-rabbit was then performed, sections mounted in Anti-fade mounting media containing DAPI and imaged using a Leica DMLA microscope.

Statistical Analyses

Statistical analyses were performed using GraphPad PRISM software. Flow cytometric samples were compared using one-way ANOVA with Tukey's multiple comparison test across samples. Datasets were treated as normal, unless otherwise stated, as assessed by median to mean agreement.

Results

NOD Mice do not Develop Tactile Allodynia in Response to *S. epidermidis* Instillation.

Figure 1B:
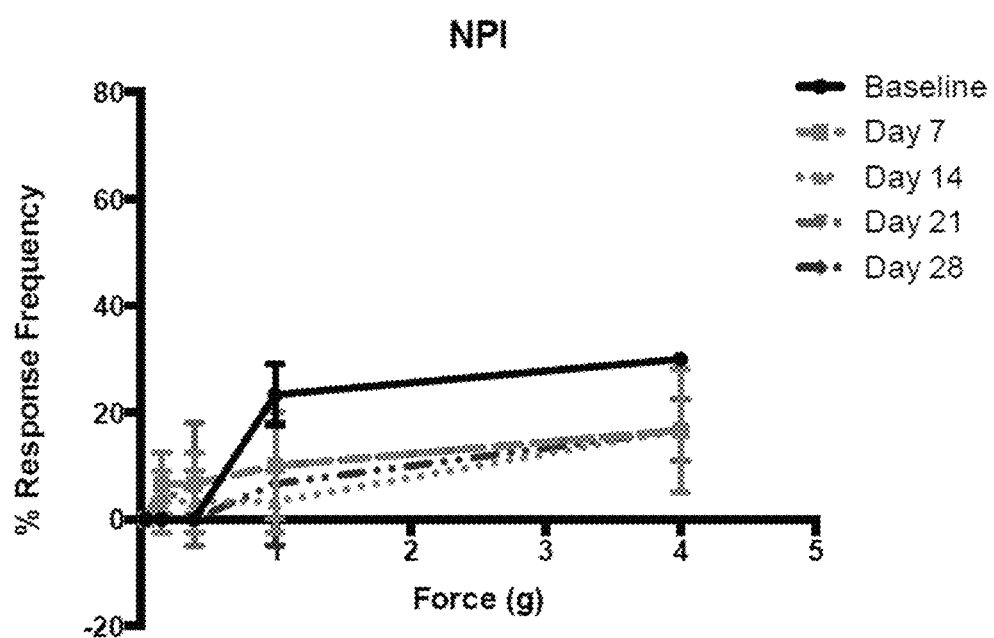
Figure 1C:
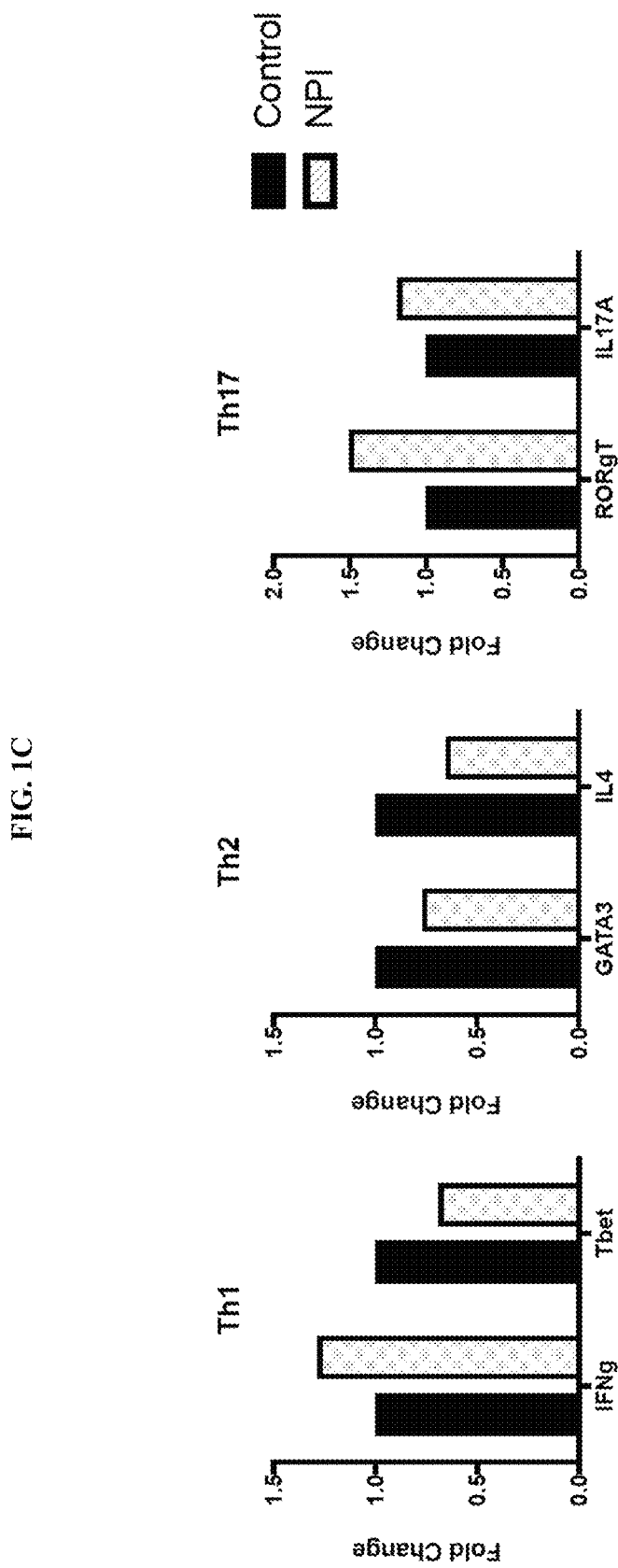

A strain of *Staphylococcus epidermidis*, NPI, was isolated from the expressed prostatic secretions (EPS) of a healthy male subject who reported no pelvic pain symptoms or symptoms related to prostate dysfunction. Experiments were conducted during development of embodiments herein to determine the consequences of NPI instillation in mice genetically predisposed to the development of pelvic tactile allodynia through altered T cell immune responses. NPI strain was administered intraurethrally into NOD mice (refs. 32,37; incorporated by reference in their entireties) and analyzed tactile allodynia responses every 7 days for 28 days and immune activation by QRTPCR. Tactile allodynia responses as assessed by behavioral testing for referred pelvic pain by tactile allodynia (ref. 31; incorporated by reference in its entirety) showed no increase in NPI treated mice compared to naïve counterparts, FIG. 1a. Expression of genes associated with CD4 T-cell subsets (T-bet, IFNg, GATA3, IL4, RORgT and IL17A) was examined in prostate tissues at day 28 and demonstrated no significant impact of bacterial instillation, FIG. 1b. These data show that NPI does not induce T-cell activation and fails to induce tactile allodynia in the genetically predisposed NOD mouse strain. These results are consistent with the nonpathogenic/commensal nature of this specific *Staphylococcus epidermidis* NPI strain in the healthy human subject from whom it was first isolated.

Intra-Urethral NPI Instillation in EAP Mice Reduces Referred Pelvic Pain.

Figure 2A:
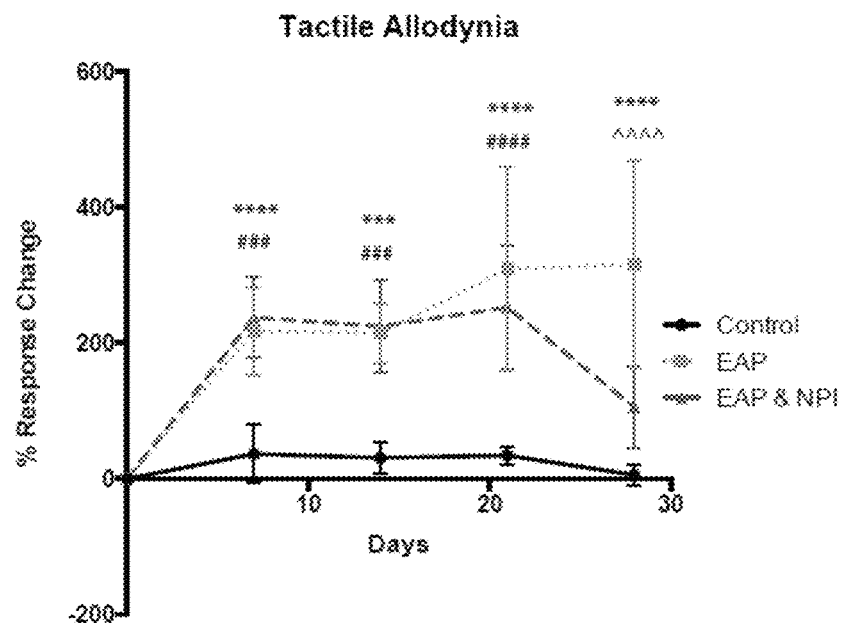
Figure 2B:
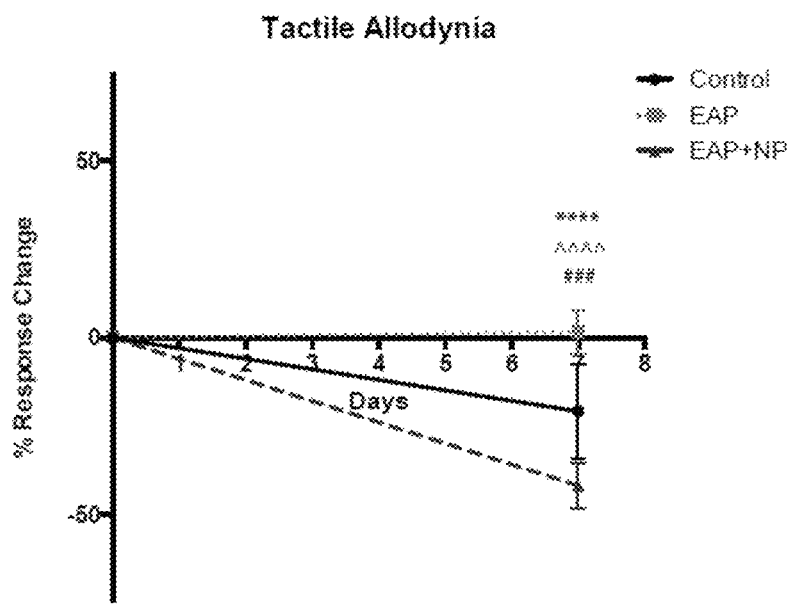
Figure 2C:
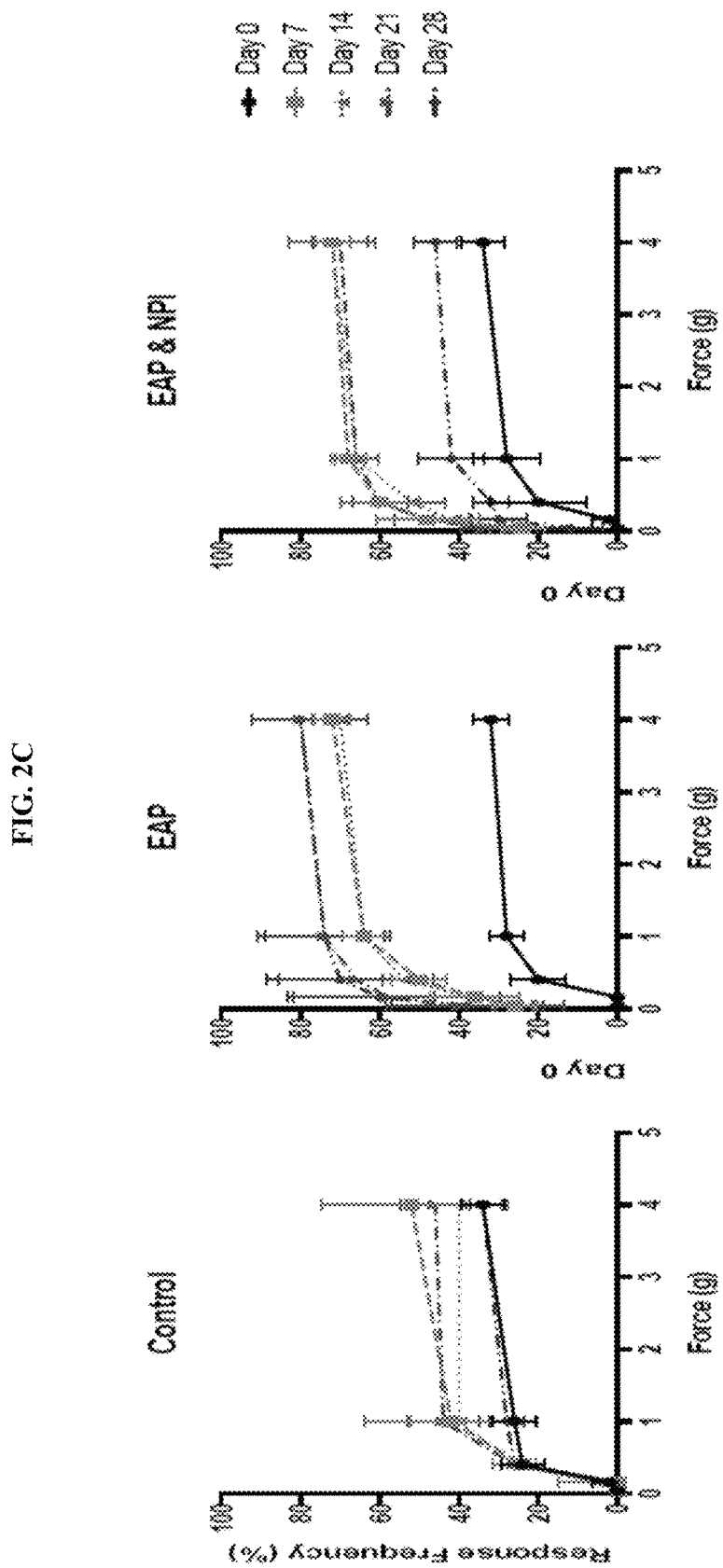
Figure 2E:
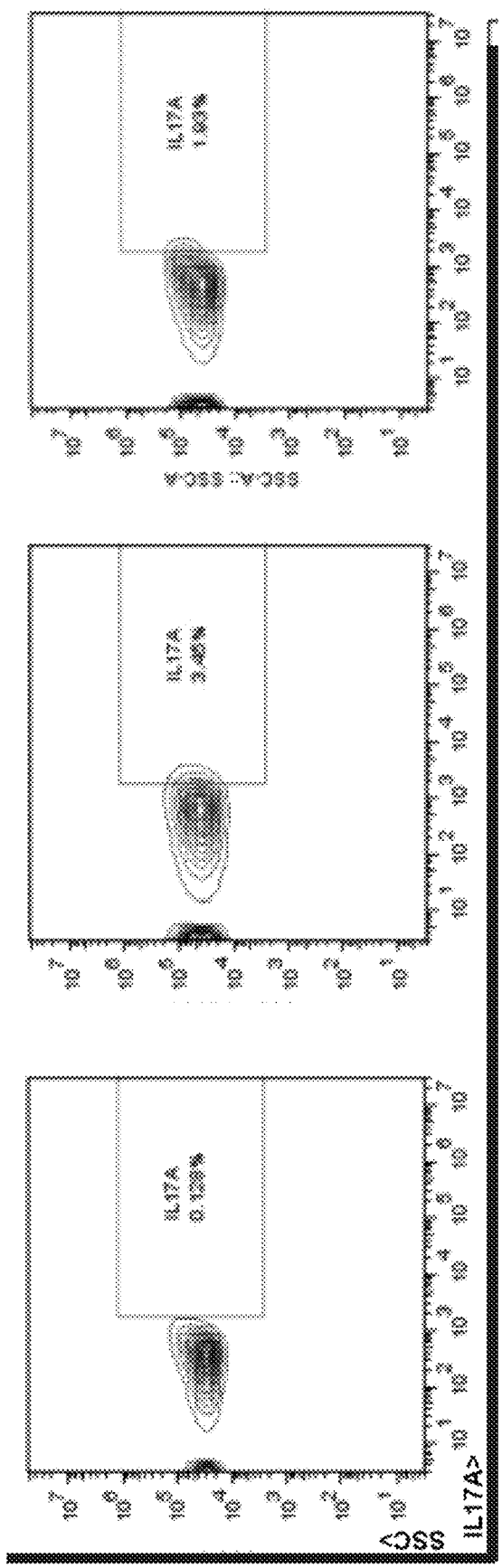
Figure 2E:
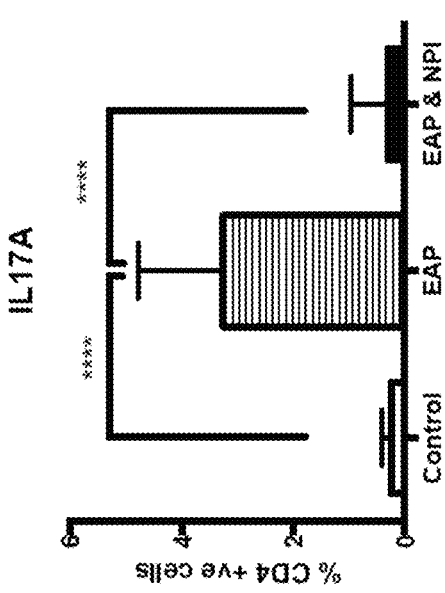
Figure 3A:
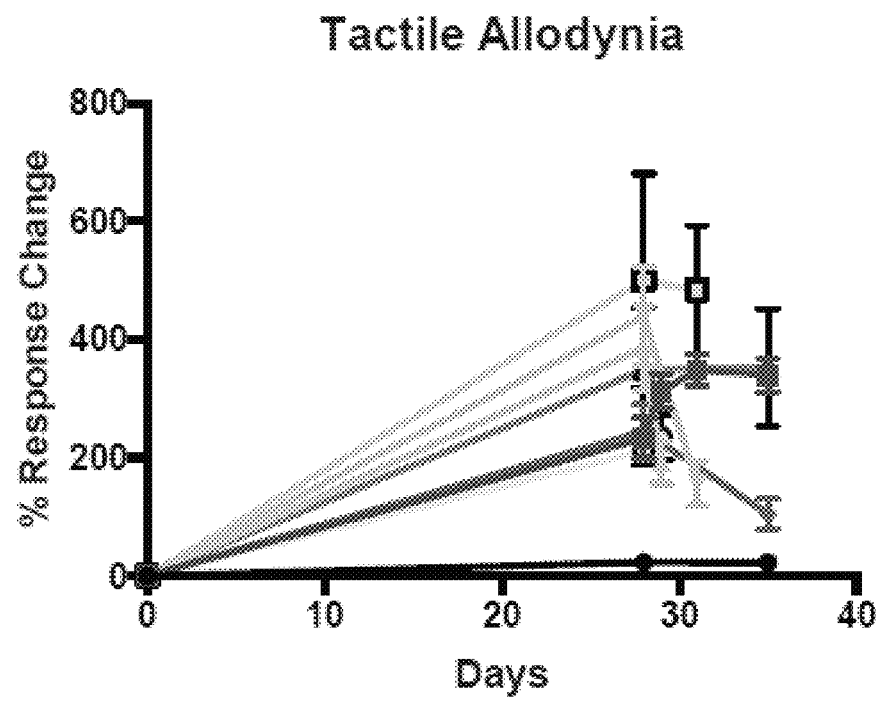
FIGS. 3A-F. Modulation of tactile allodynia by instillation of NPI is not due to differential colonization of the mouse prostate.
Figure 3A:
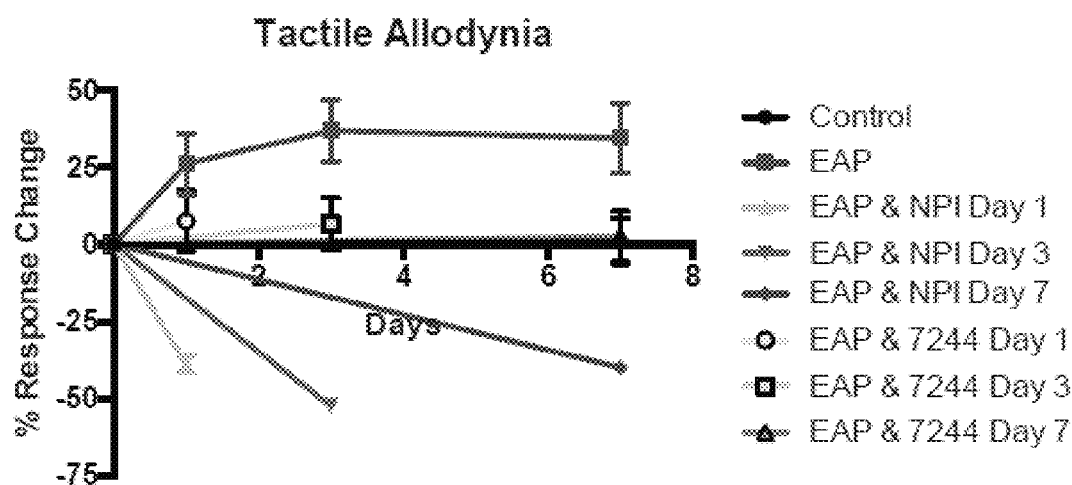
Figure 3B:
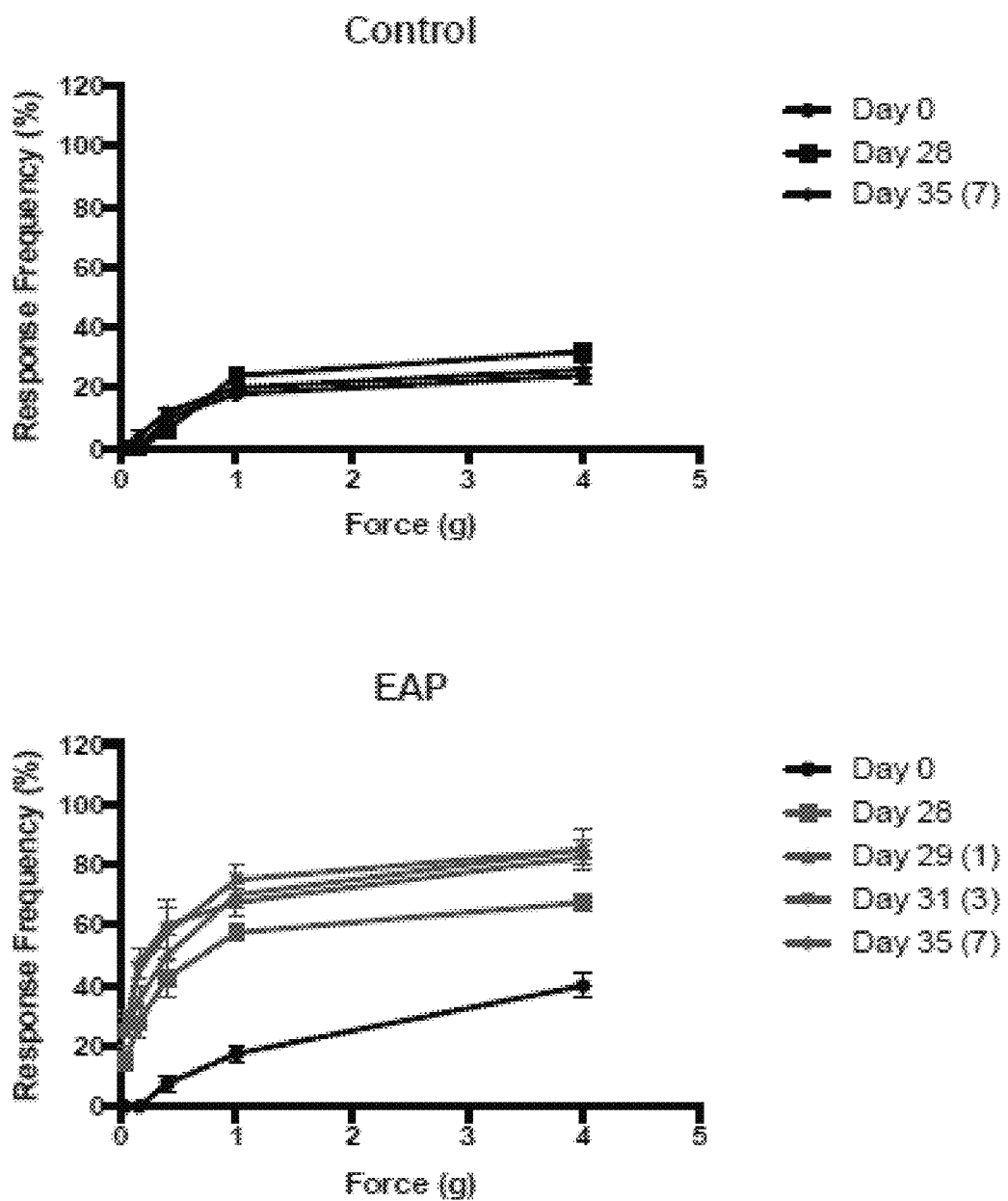
Figure 3C:
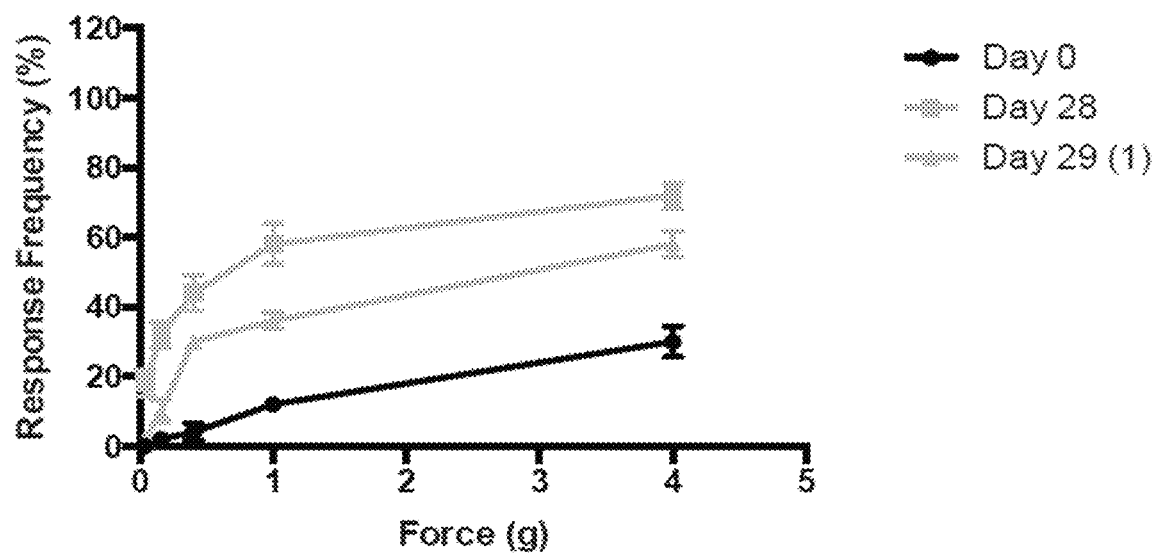
Figure 3C:
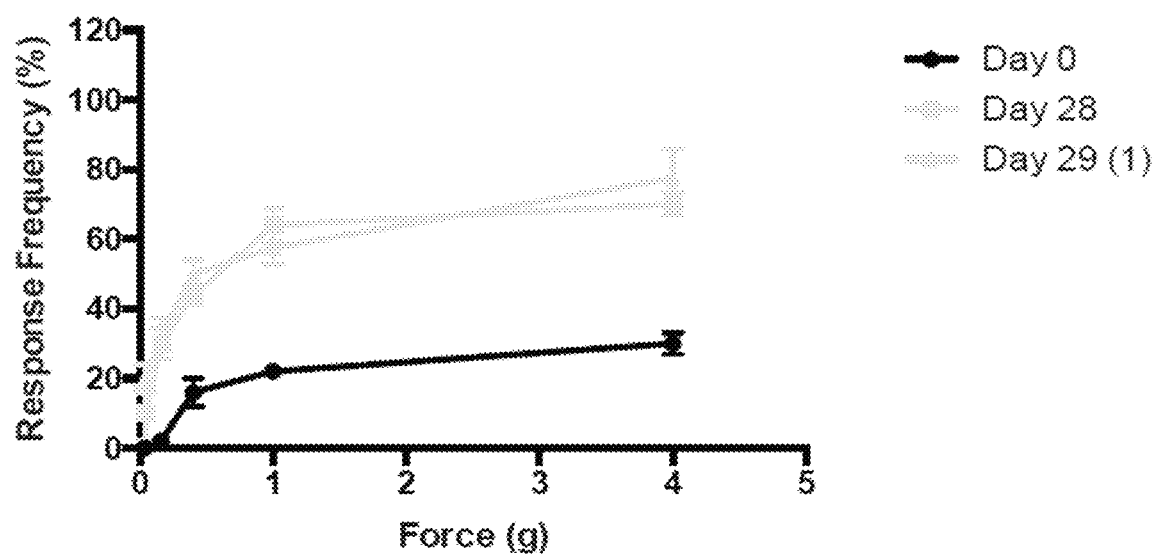
Figure 3D:
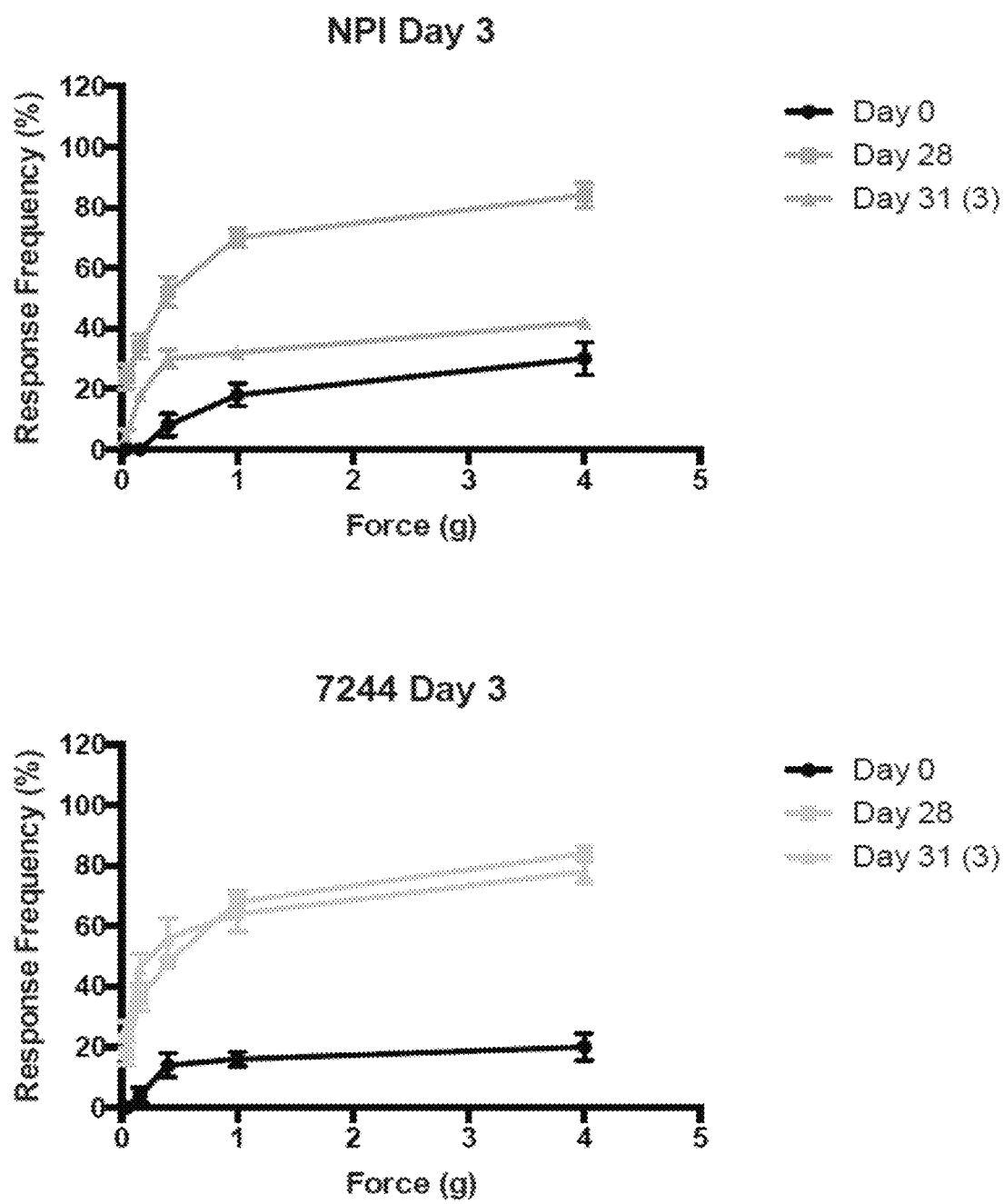
Figure 3E:
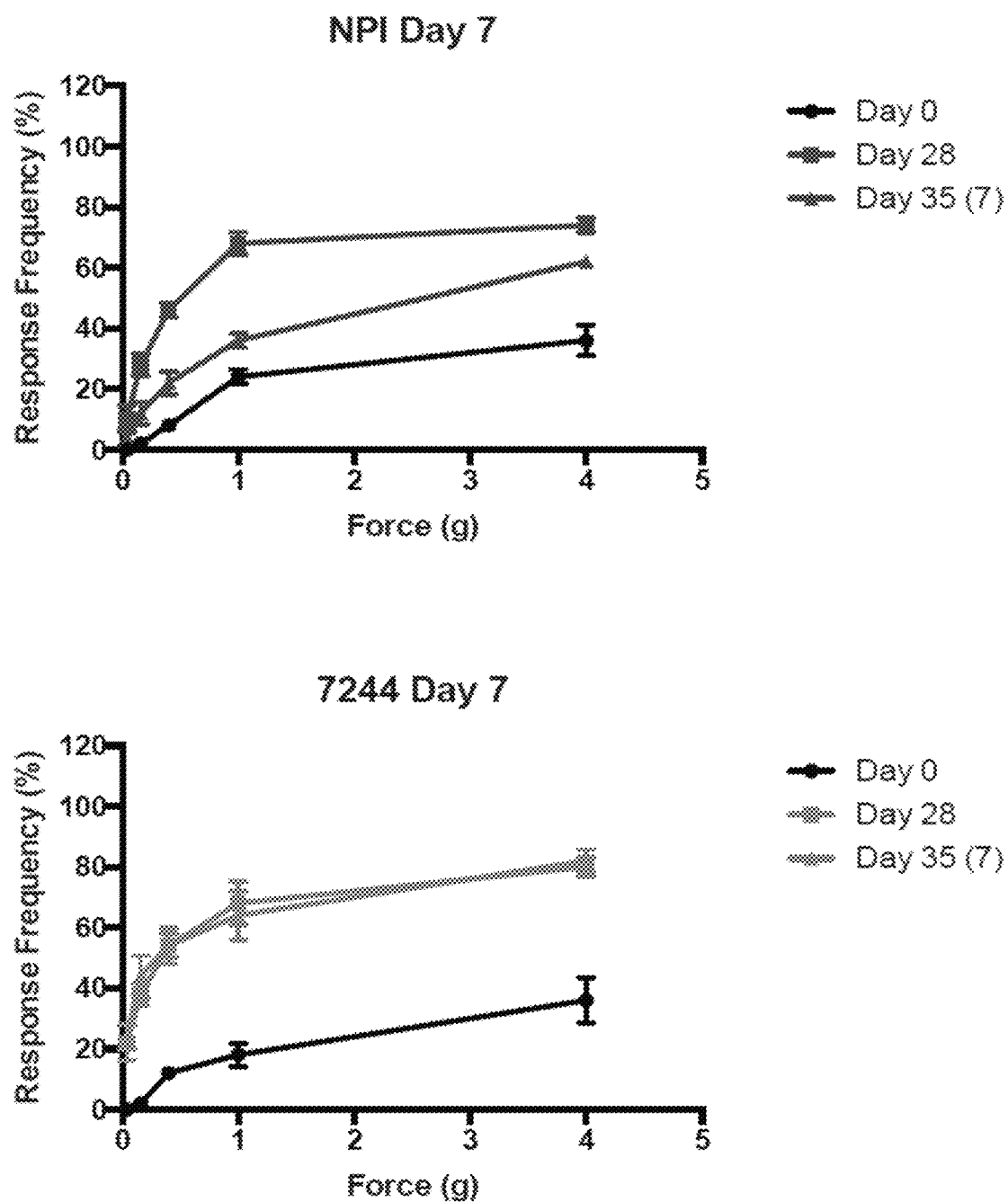
Figure 3F:
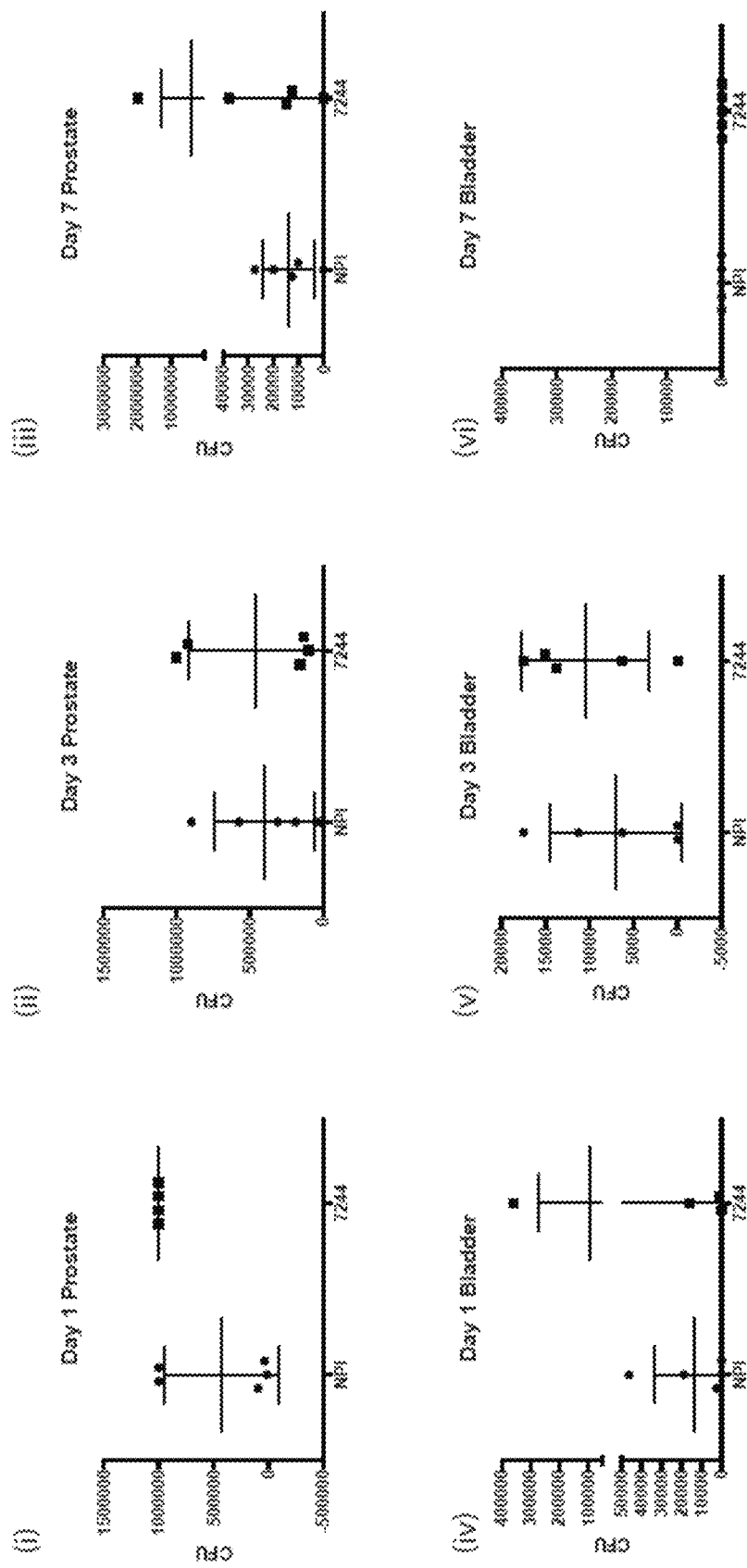
Figure 4A:
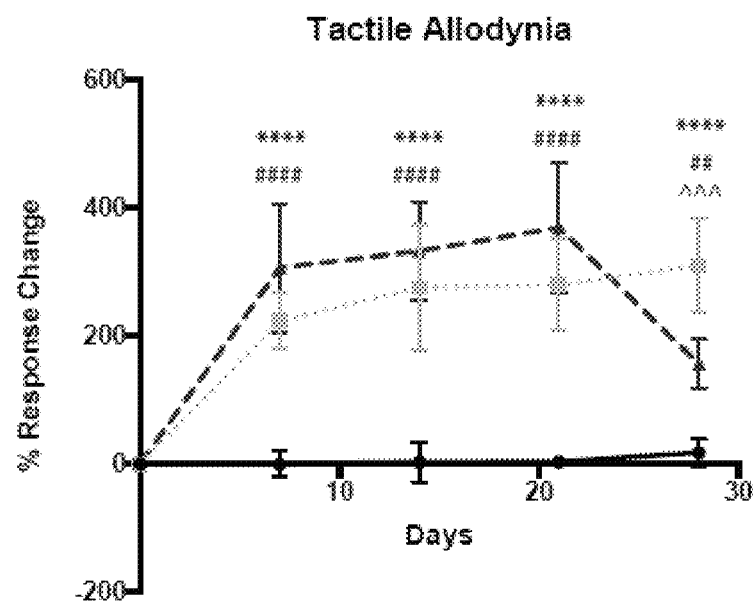
FIGS. 4A-I. Intraurethral treatment of EAP mice with LTA from the NPI strain instillation ameliorates tactile allodynia in a strain specific manner.
Figure 4B:
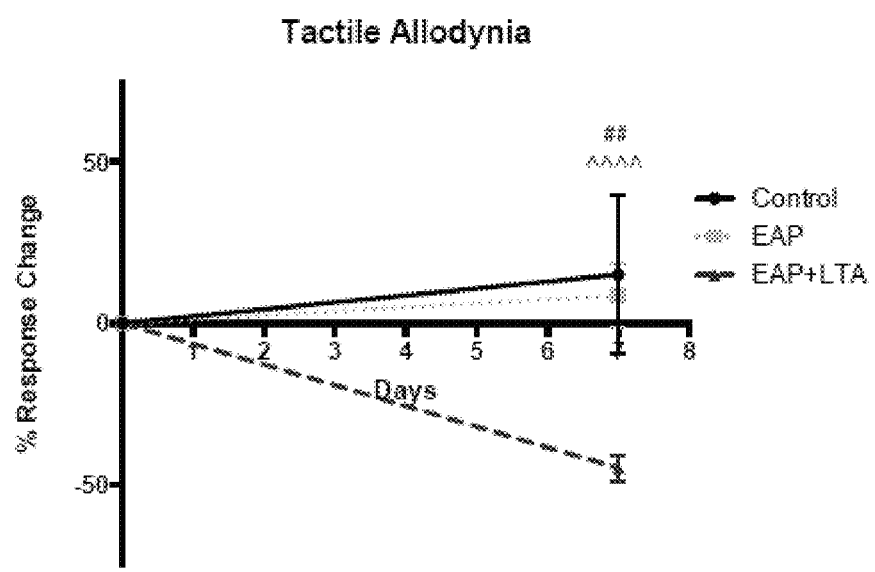
Figure 4C:
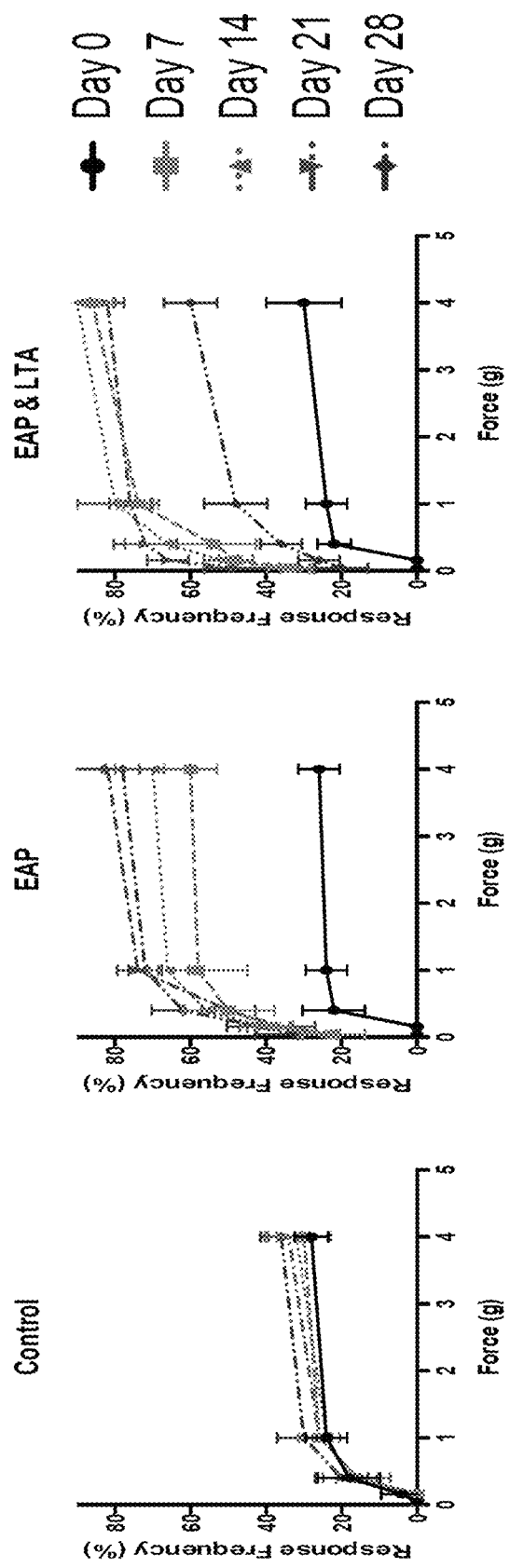
Figure 4D:
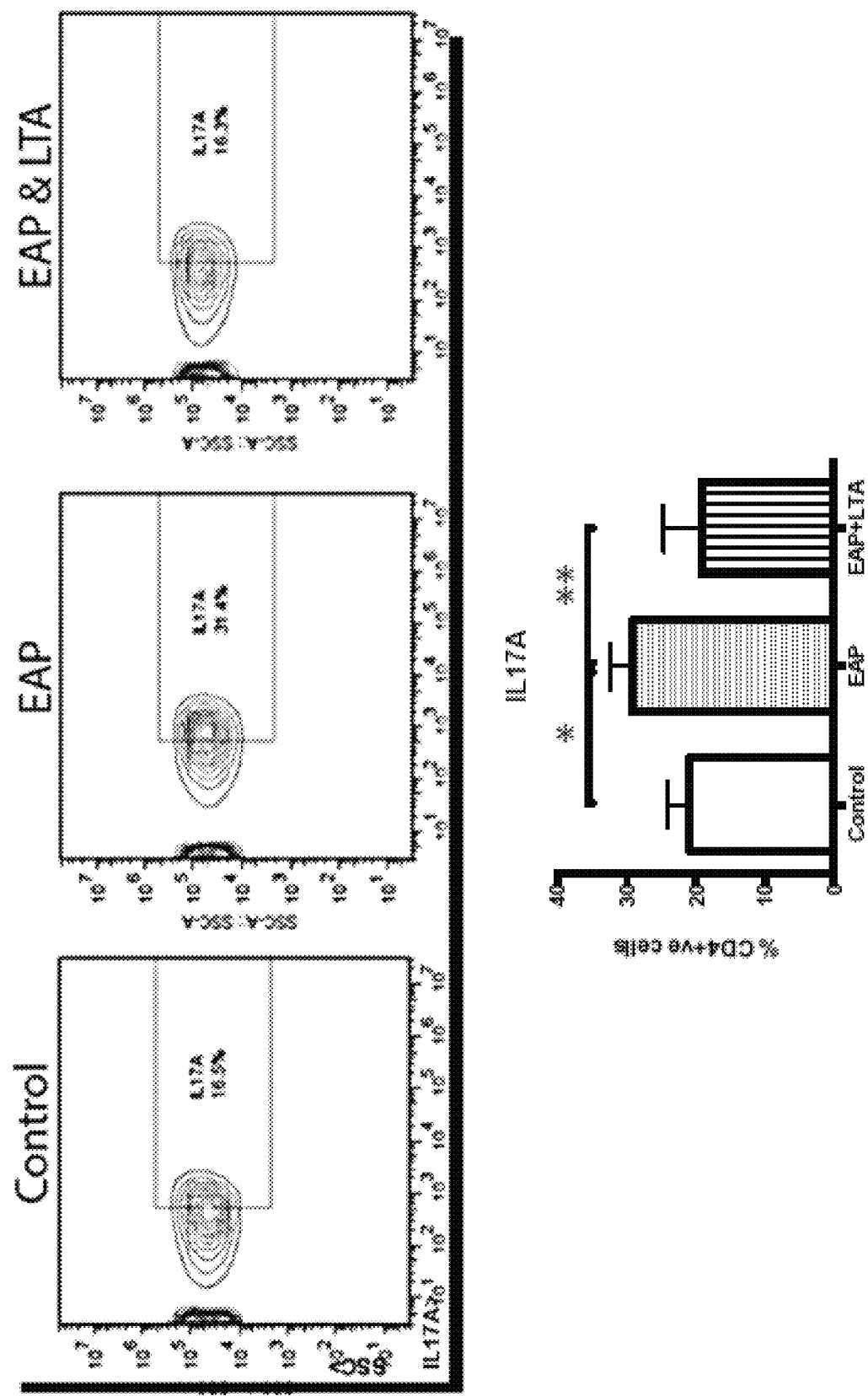
Figure 4E:
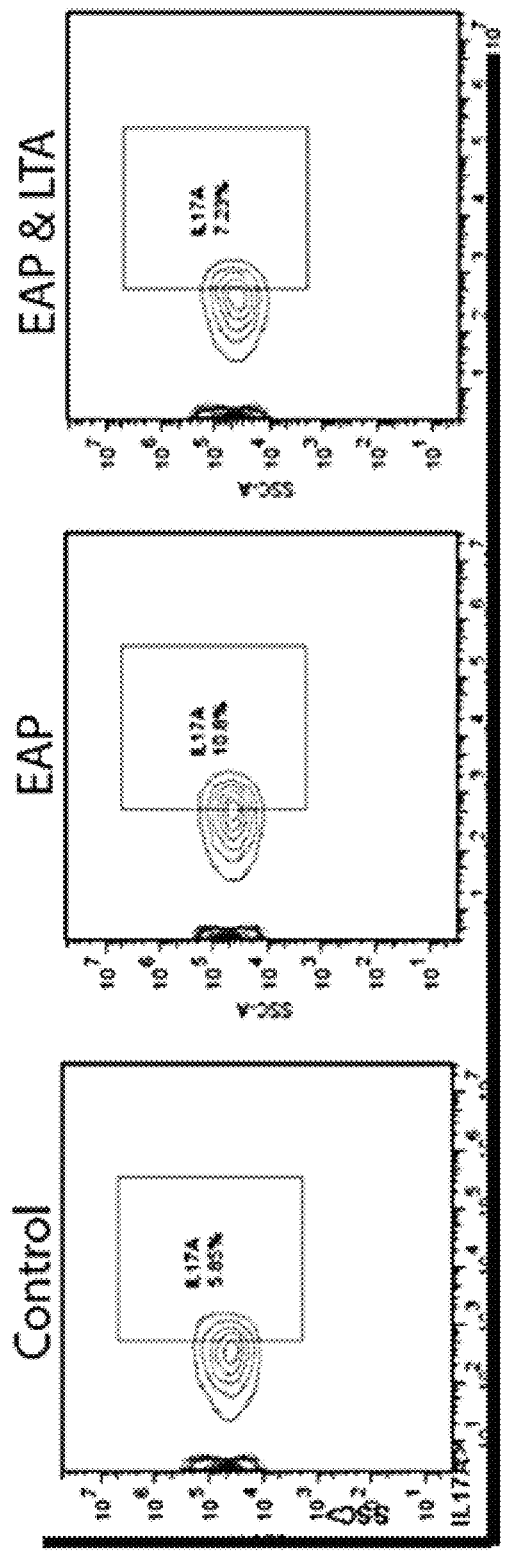
Figure 4E:
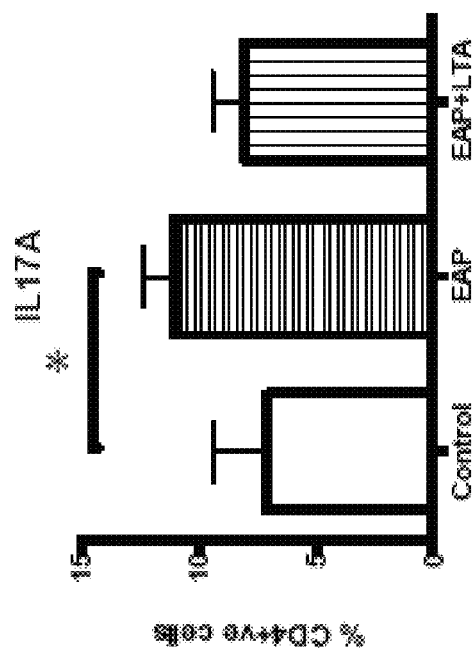
Figure 4F:
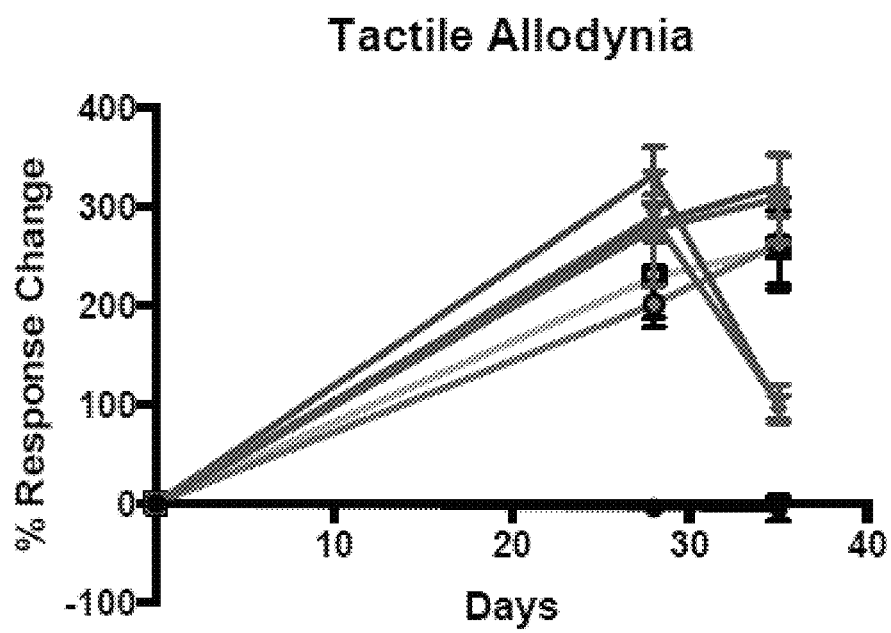
Figure 4G:
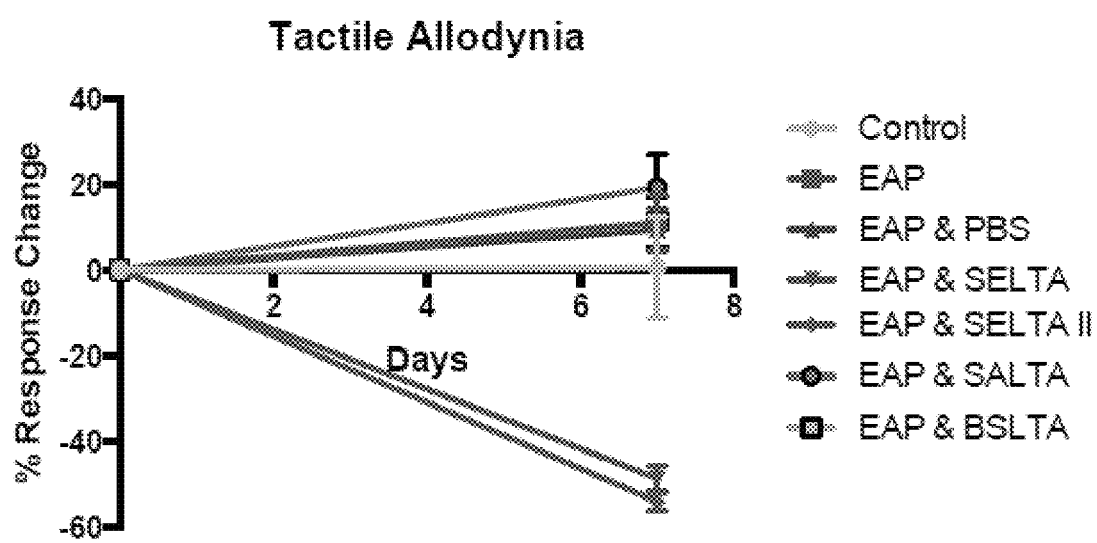
Figure 4H:
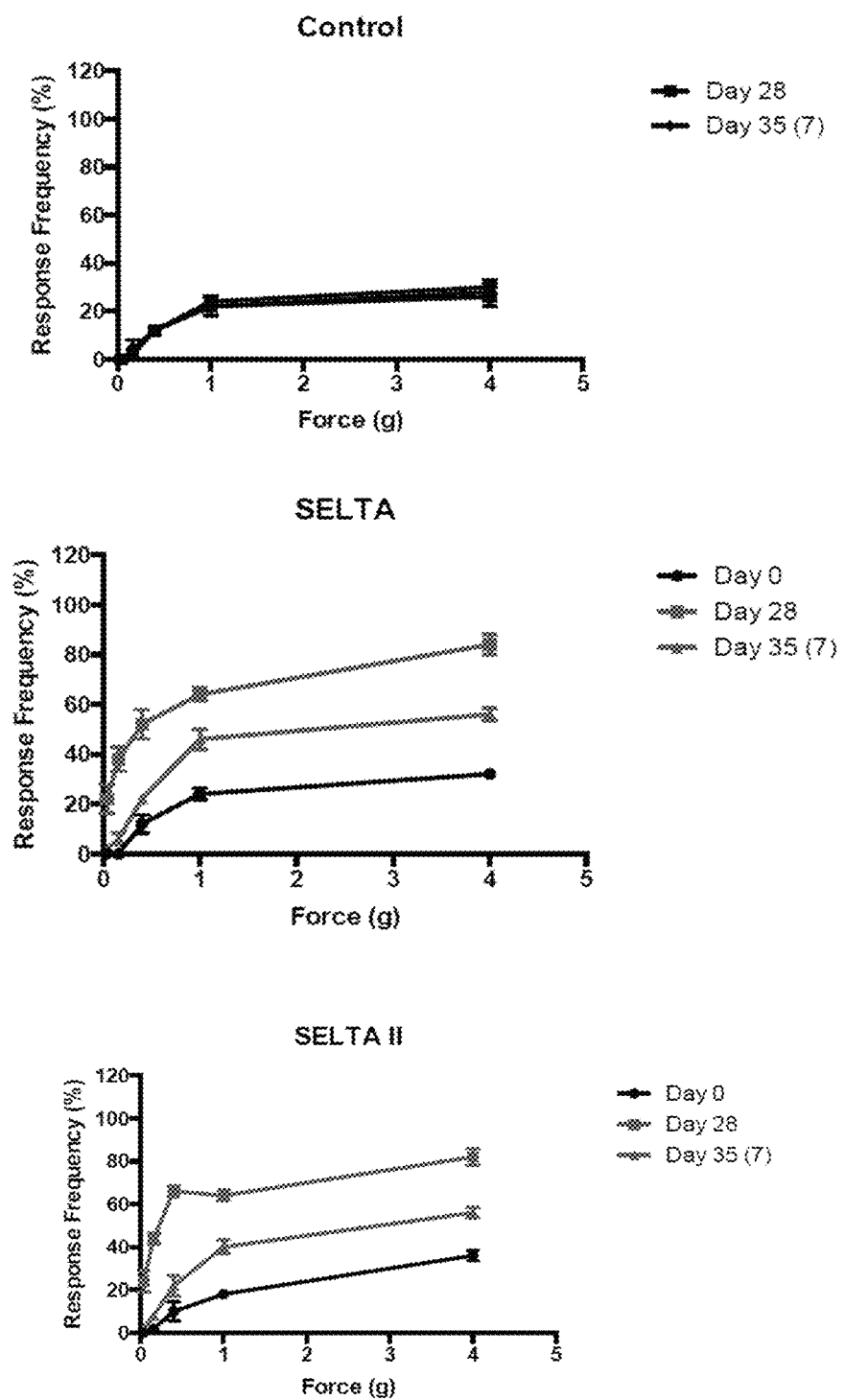
Figure 4I:
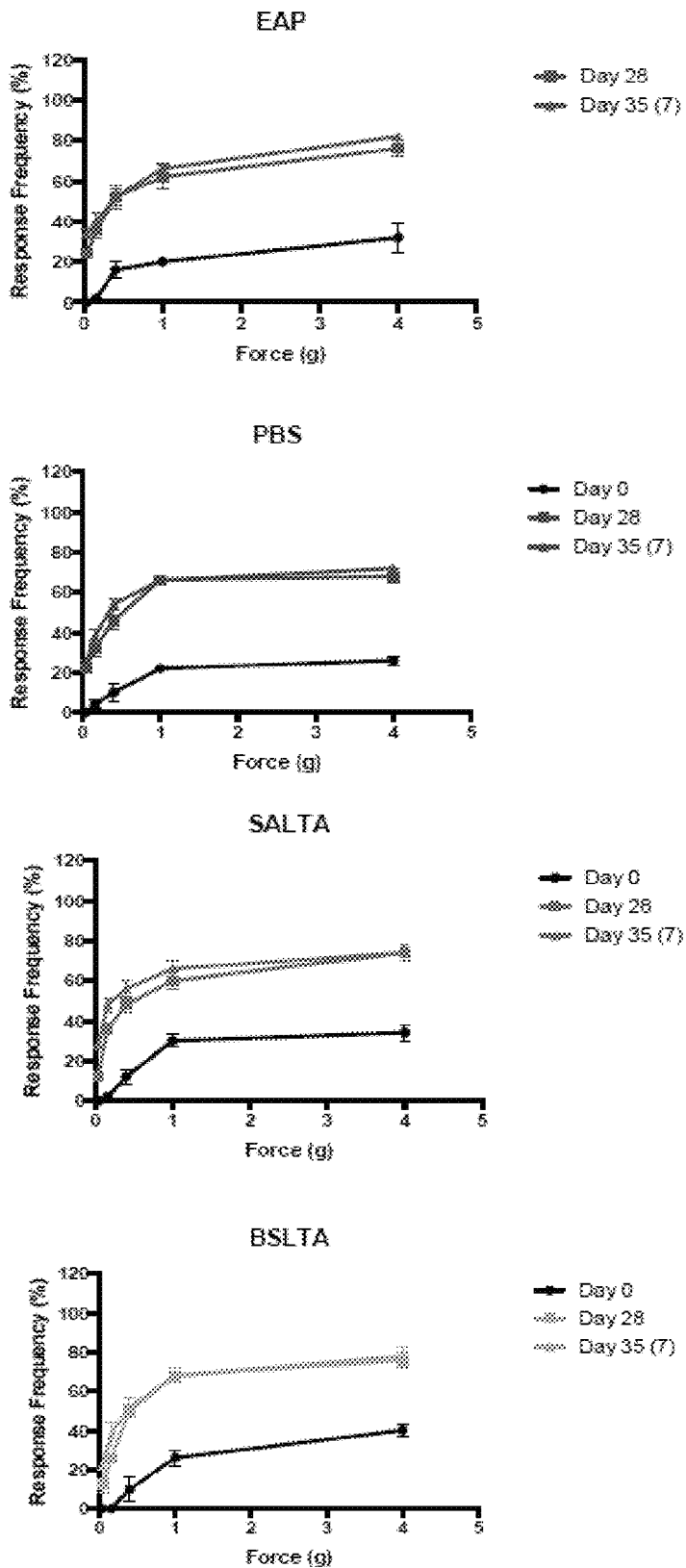

Experiments were conducted during development of embodiments herein to examine what effect instillation of NPI would have on tactile allodynia responses during ongoing inflammation using the xenogeneic model of prostatitis. EAP was induced in immunocompetent C57BL/6 mice (refs. 35,39; incorporated by reference in their entireties) and symptom development was monitored by behavioral testing every seven days for 21 days. At day 21, when prostatitis induction is deemed chronic as characterized by the presence of chronic tactile allodynia and alterations in immune response, NPI was intraurethrally instilled and the experiment continued for a further 7 days. Increased tactile allodynia responses upon EAP induction were observed (FIG. 2a) but these were significantly blunted following instillation with the bacteria at day 21. Tactile allodynia responses were ameliorated up to 50% compared to EAP mice alone (FIG. 2b). These findings were consistent for every Von Frey filament analyzed (FIG. 2c). Mice were sacrificed at day 28 and the effect of NPI instillation on prostatic immune responses examined by flow cytometric analysis of CD4+ve T-cells. Increased levels of CD4+ve IL17A+ve T-cells were observed upon induction of EAP in prostate tissues (ref. 25; incorporated by reference in its entirety) (FIG. 2d), this increase was lost upon treatment with NPI for 7 days. These findings were mirrored by loss of increased IL17A expressing CD4 T-cells in the iliac lymph nodes of EAP and NPI treated mice (FIG. 2e).

NPI's Effects on Tactile Allodynia are Strain Specific but not Dependent on Levels of Prostate Bacterial Colonization.

To examine whether the effects on tactile allodynia and immune modulation were specific to the commensal *Staphylococcus* species isolated from the normal prostate, experiments were conducted during development of embodiments herein to directly compare the ability of NPI to reduce tactile allodynia in EAP mice with that of an *S. epidermidis* 7244 strain isolated from the EPS of a CPPS patient with active disease. Mice were given EAP for 28 days and behavioral testing was performed at both Day 0 and Day 28. Following this, mice were instilled with either the NPI or the 7244 strains. Behavioral testing was performed at Day 29 (1-day post treatment), Day 31 (3 days post treatment) and Day 35 (7 days post treatment). At each time point (days 1, 3 & 7) mice were sacrificed (4-5 per group) and colony formation assays performed on both prostate and bladder tissues. The NPI strain showed reduced tactile allodynia responses in C57BL/6 mice when compared to 7244, FIG. 3A-E, in NOD mice. There were no significant differences observed between the ability of the NPI and 7244 strains to colonize the bladder (days 1 and 3) and prostate (days 1, 3 and 7), FIG. 3 F (i-vi). Taken together these data demonstrate that bacterial colonization does not account for reduced responses observed upon instillation with NPI. Rather it is the ability of this strain to modulate the prostate immune milieu that accounts, at least in part, for these effects.

LTA is the Immunogenic Component of NPI

Due to the apparent strain specific nature of NPI to counteract EAP induced tactile allodynia response, experiments were conducted during development of embodiments herein to determine the bacterial component responsible. LTA was isolated from the NPI bacterial strain by HPLC and intra-urethrally instilled into naïve and EAP mice. LTA treatment significantly decreased tactile allodynia responses (FIG. 4A, & B) for every filament examined, FIG. 4C. Flow cytometric analysis of prostate single cell suspensions for CD4 T-cells revealed decreased levels of IL17A expression upon treatment with LTA for 7-days, FIG. 4D. LTA treatment also resulted in decreased IL17A producing T-cells in the iliac lymph nodes, FIG. 4E. In order to investigate the specificity of this isolated LTA from the NPI strain we compared the ability of additional LTA molecules to modulate tactile allodynia responses upon EAP. Mice were given EAP and tactile allodynia allowed to develop for 28 days following which mice were treated intra-urethrally with either PBS, *S. epidermidis* LTA (SELTA), a second batch of SELTA, LTA isolated from *S. aureus* (SALTA) or LTA from *B. subtilis* (BSLTA). FIG. 4(F-I), shows tactile allodynia response curves from these mice demonstrating that the effect of LTA is specific only to that isolated from the *S. epidermidis* NPI strain. Taken together these data indicate that instillation with NPI modulates tactile allodynia responses via the LTA constituent of its cell wall. LTA molecules vary significantly between microbes and this is also borne out by the inability of the LTA molecules tested, with the exception of SELTA, to reduce tactile allodynia in response to EAP.

LTA Increases Expression of CD274/CD273 (PDL1/2) on CD11b+Ve Cells.

Figure 5A:
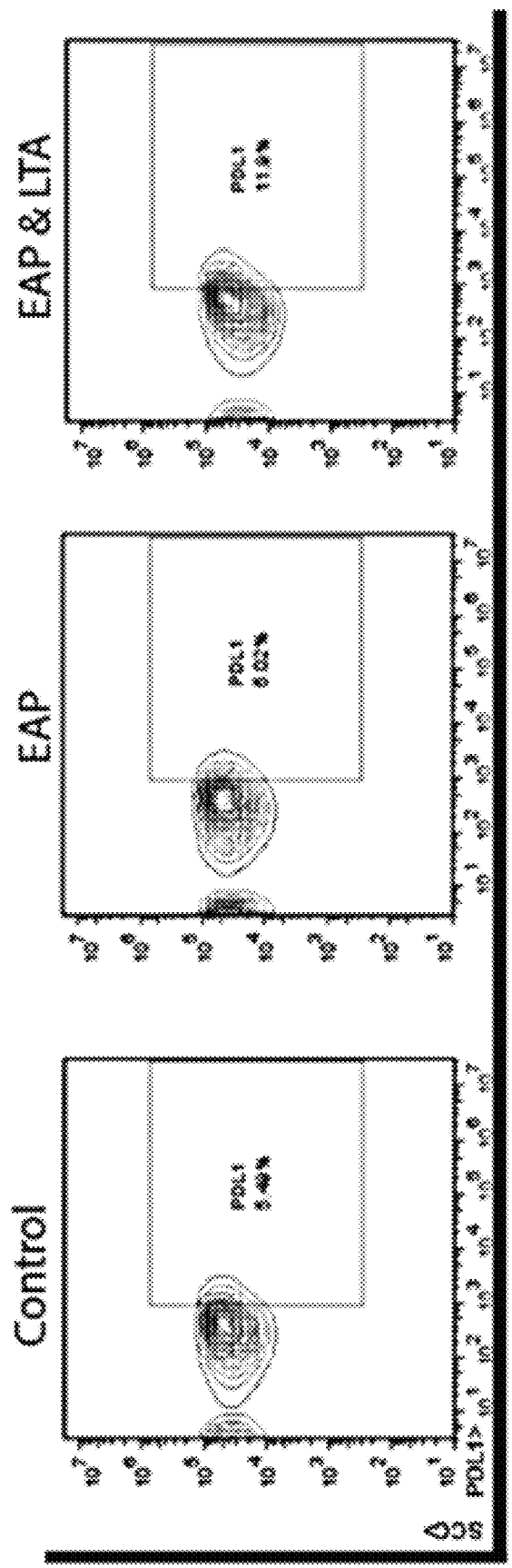
FIGS. 5A-E. LTA induces PDL1/2 expression on the surface of APC of the prostate.
Figure 5A:
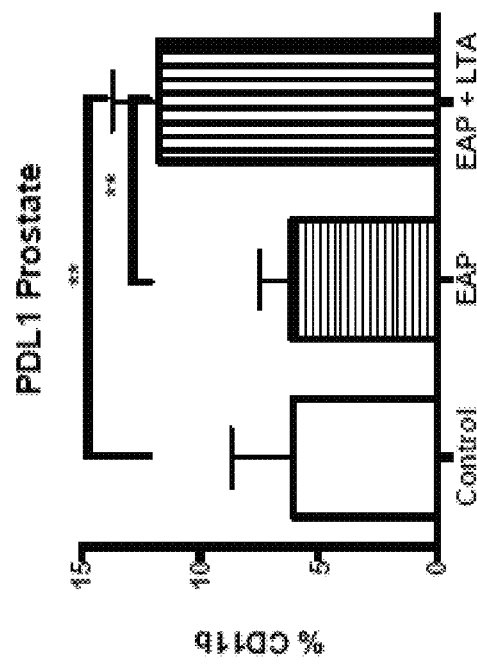
Figure 5B:
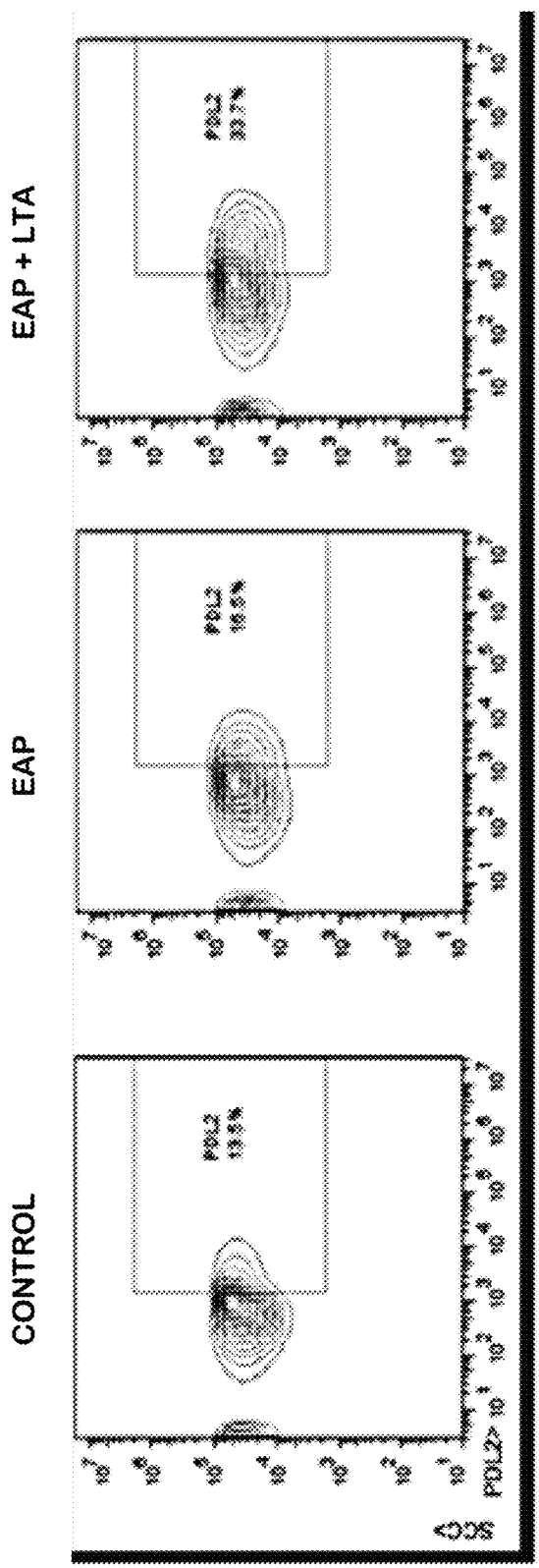
Figure 5B:
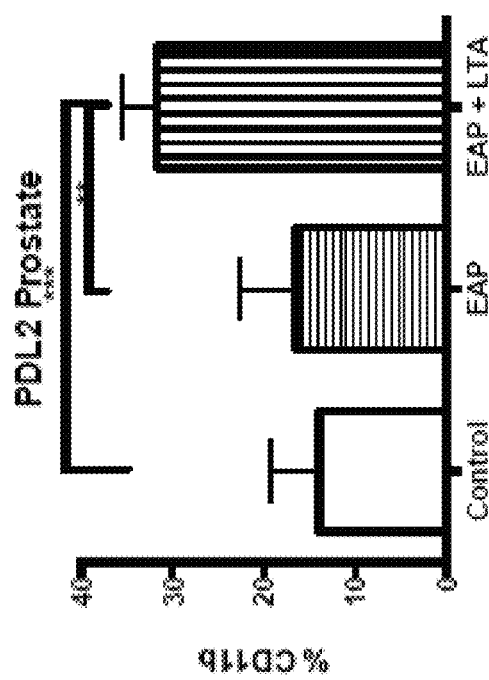
Figure 5C:
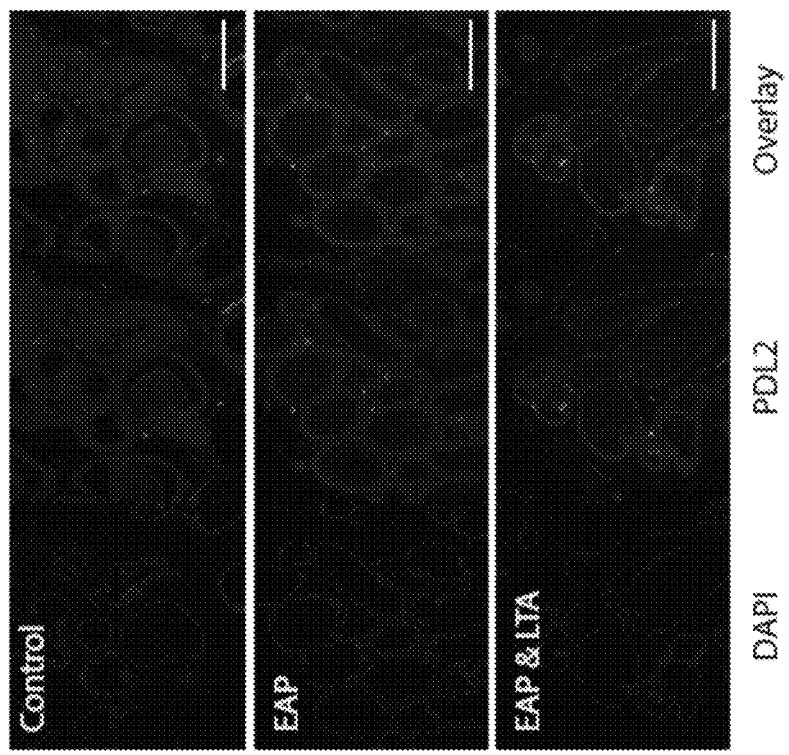
Figure 5D:
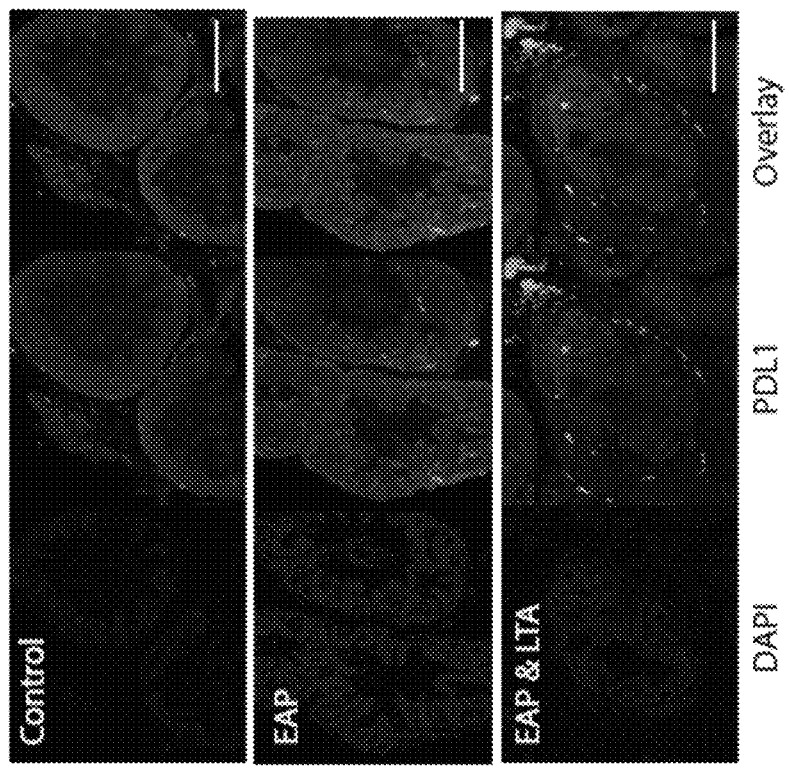
Figure 5E:
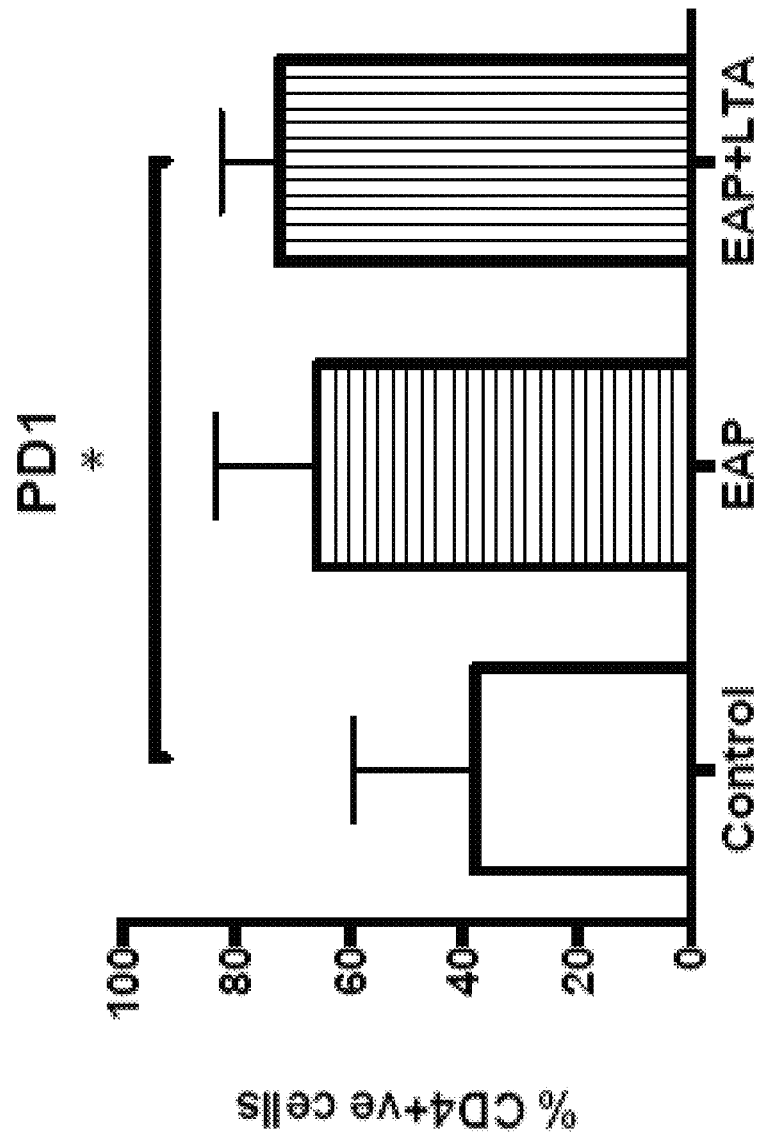
Figure 6A:
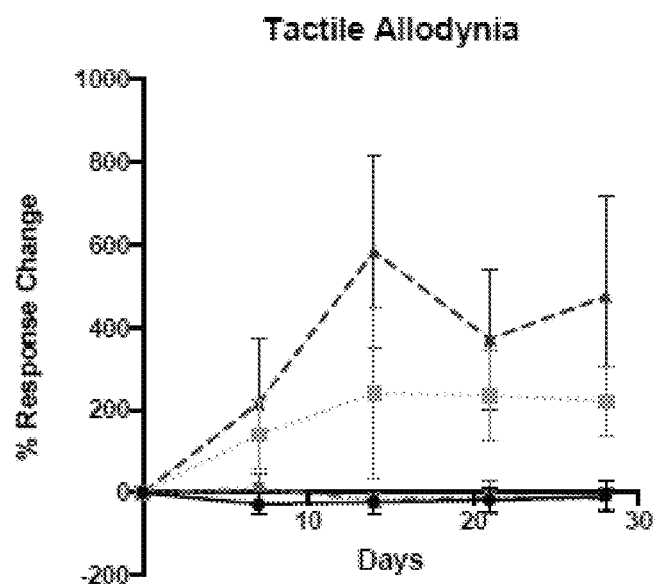
FIGS. 6A-G. Effects of NPI and LTA on tactile allodynia is dependent on IL10, PD1 and CD25 expressing cells.
Figure 6B:
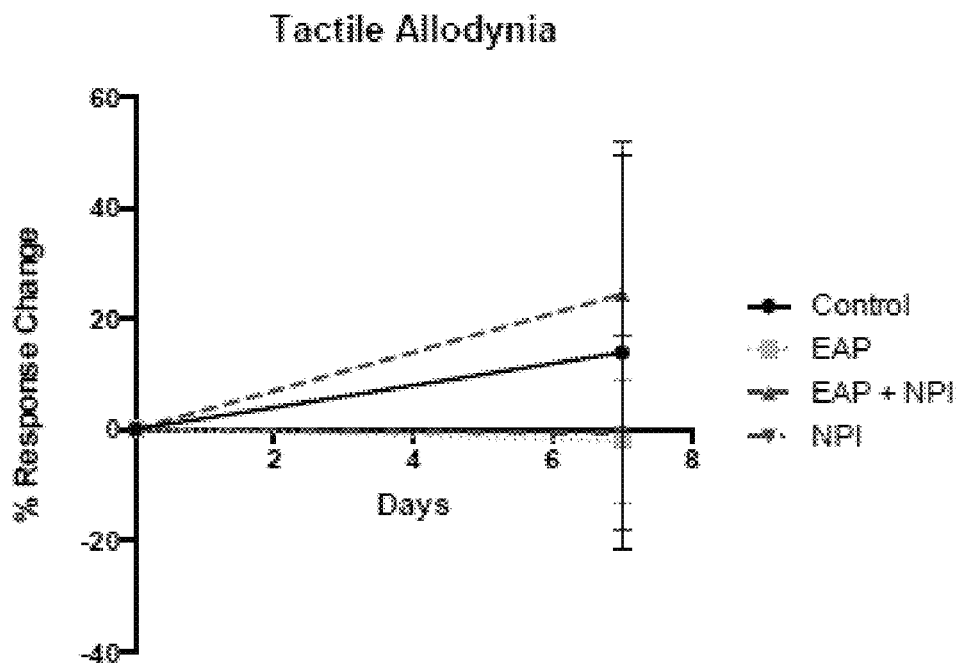
Figure 6C:
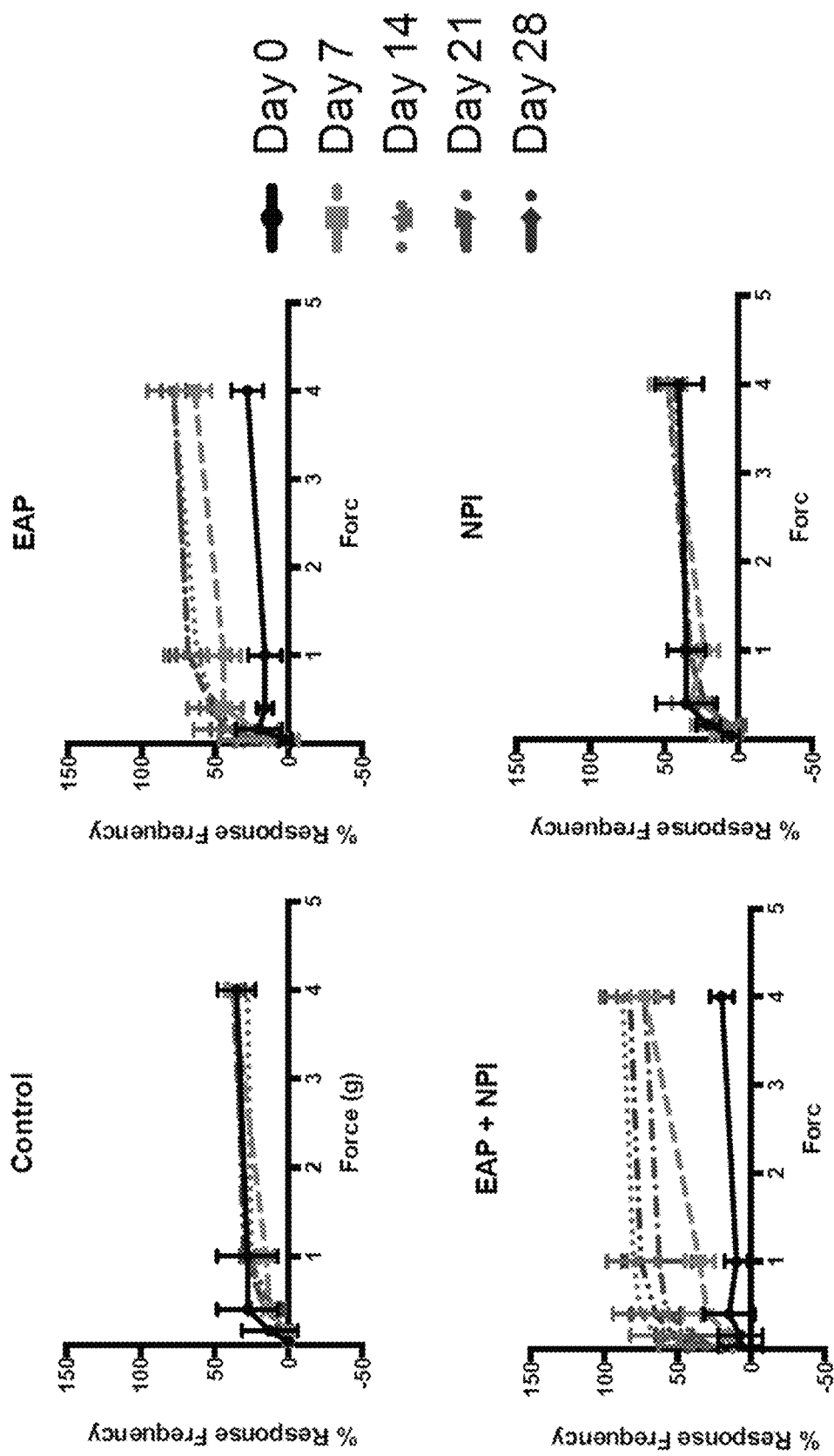
Figure 6D:
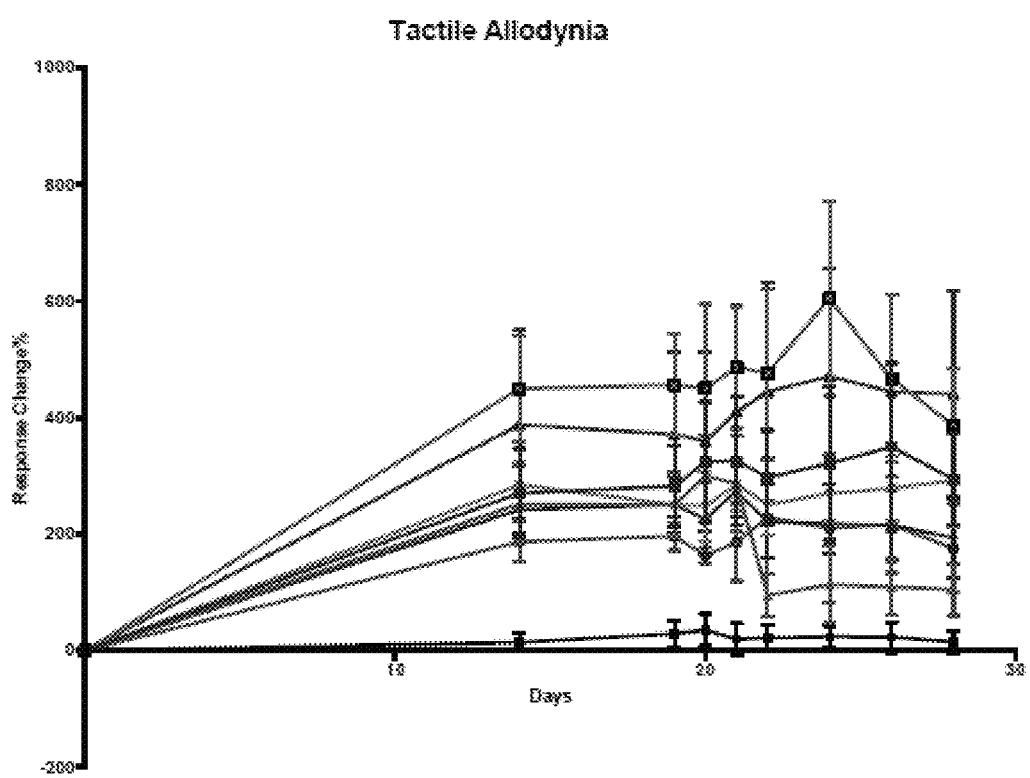
Figure 6E:
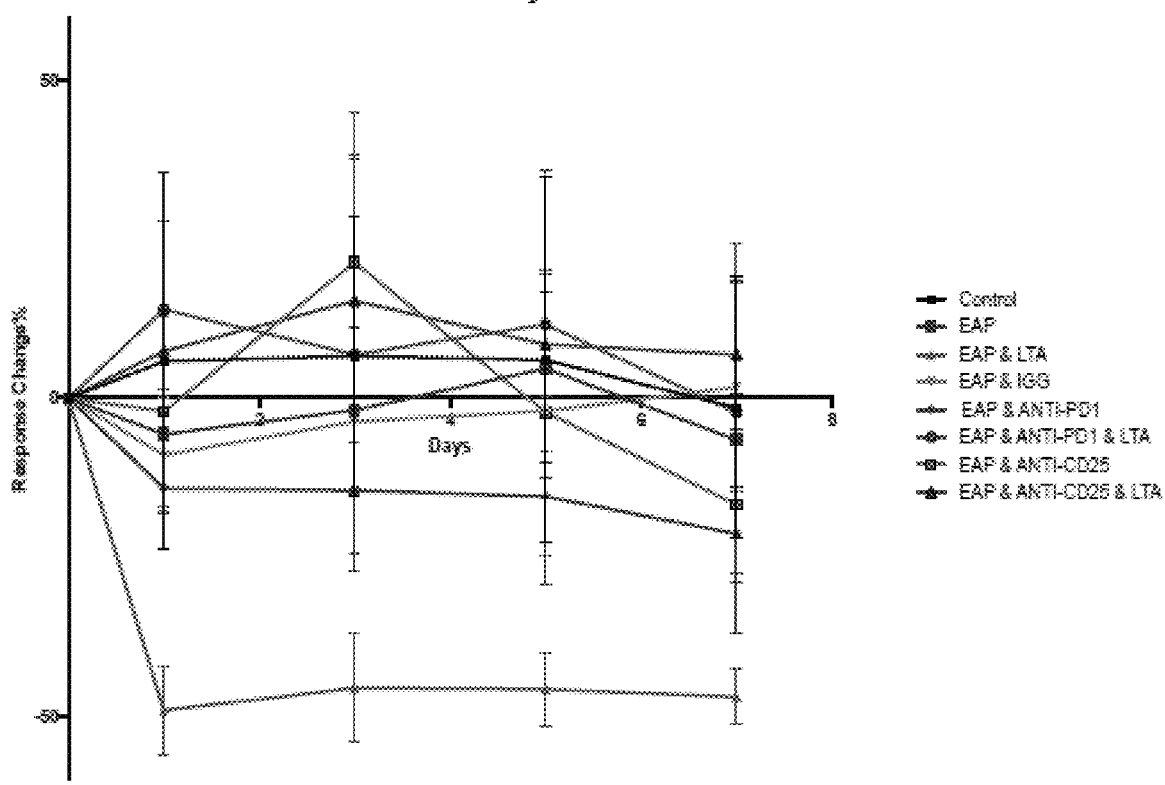
Figure 6F:
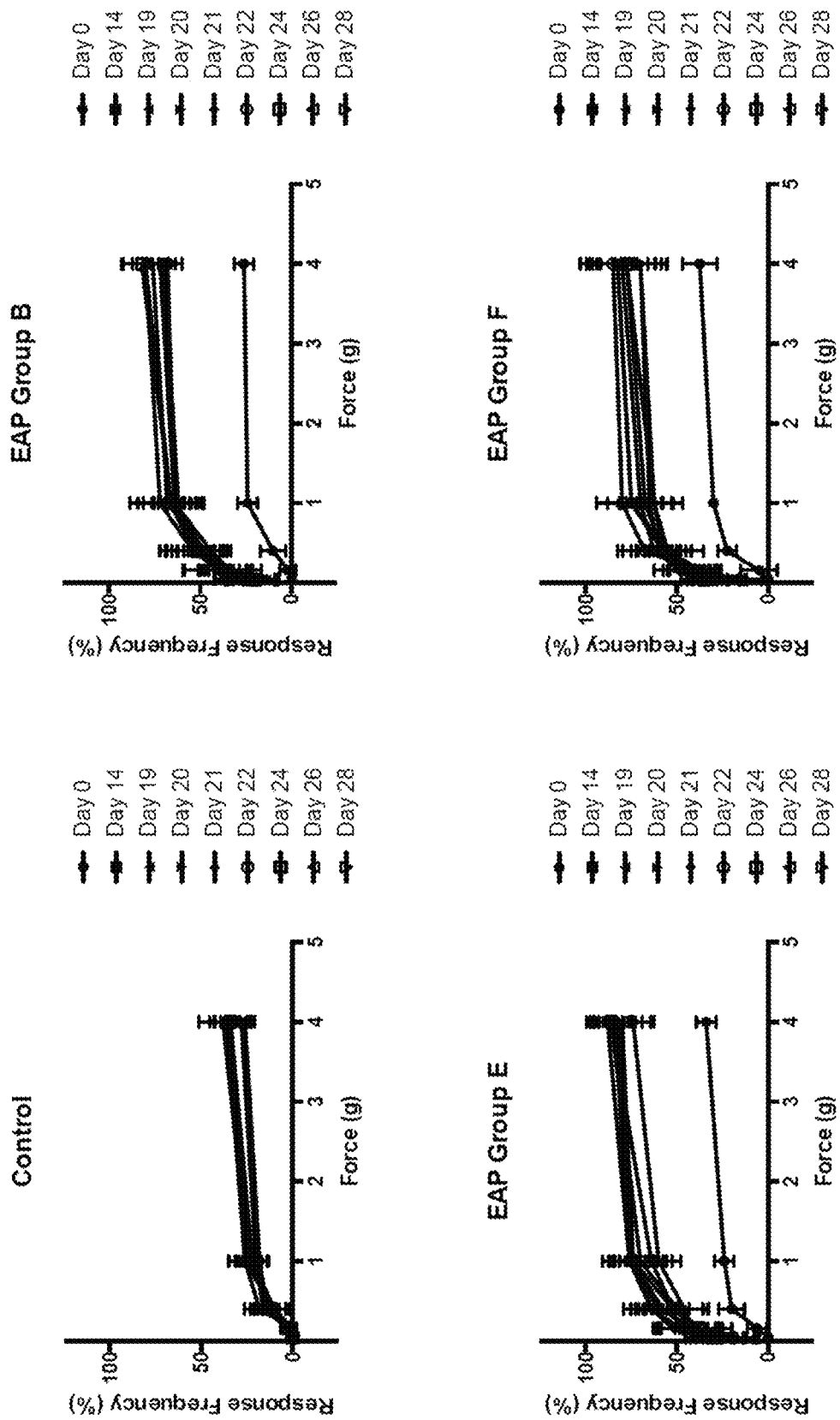
Figure 6G:
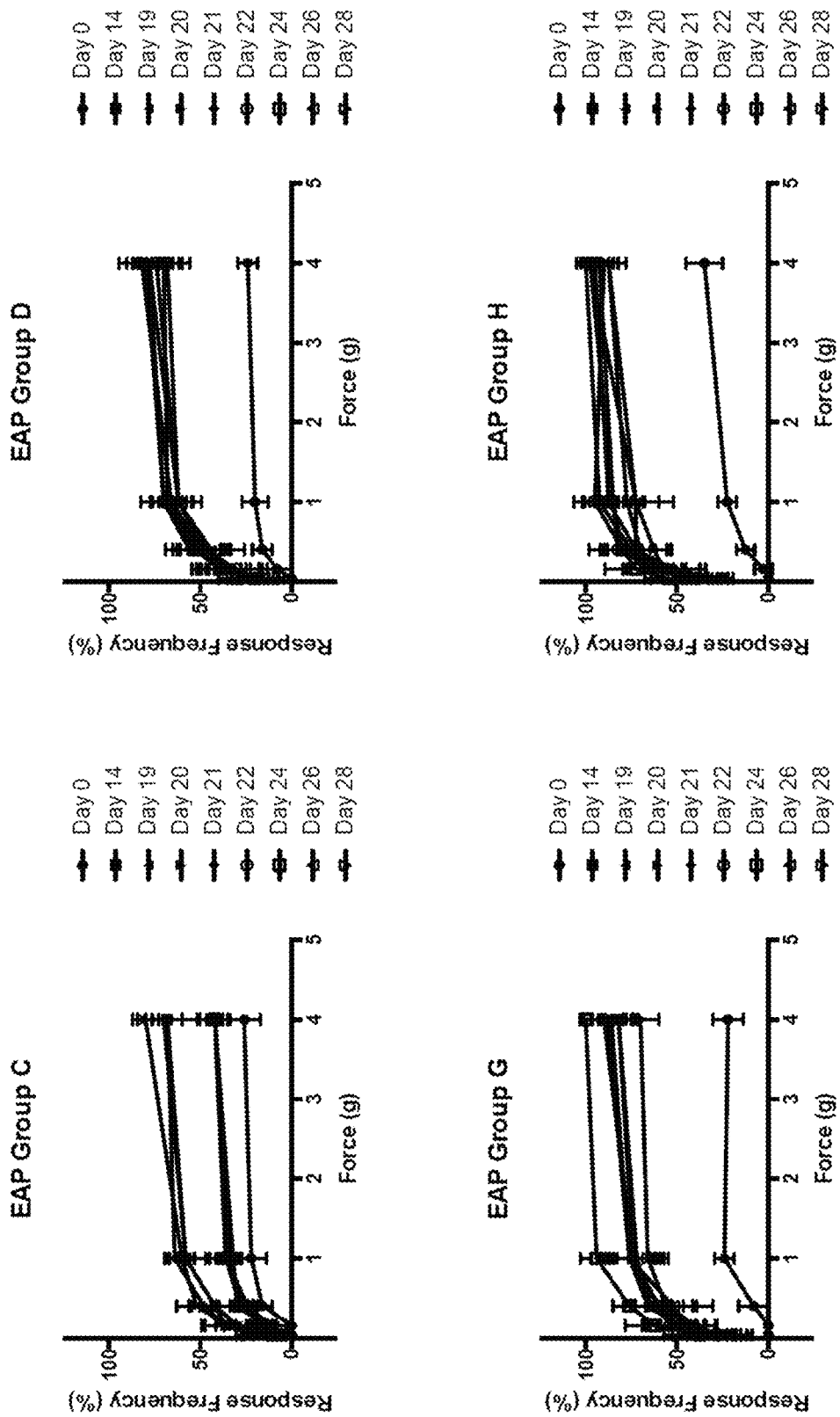
Figure 7A:
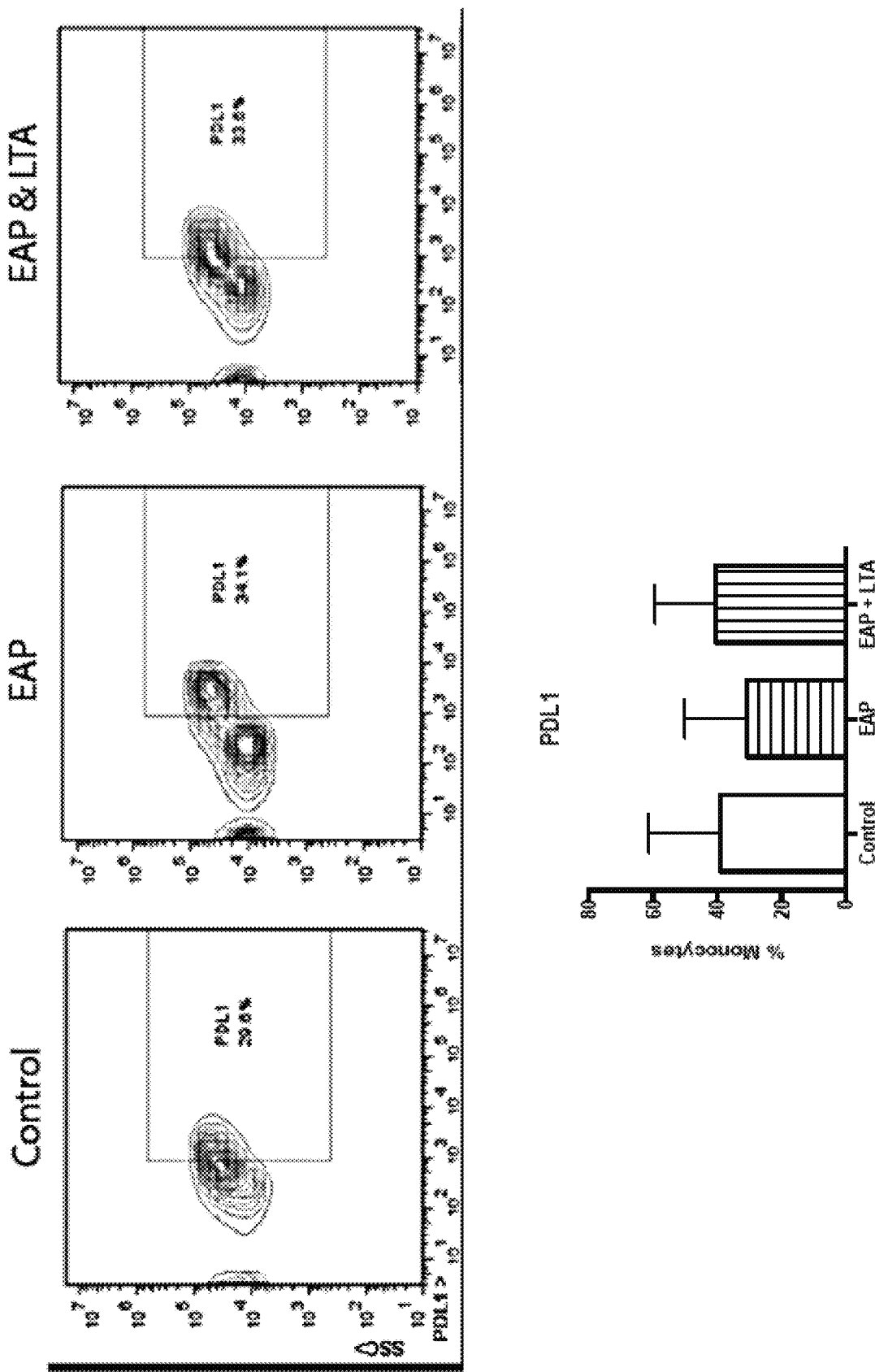
Figure 7B:
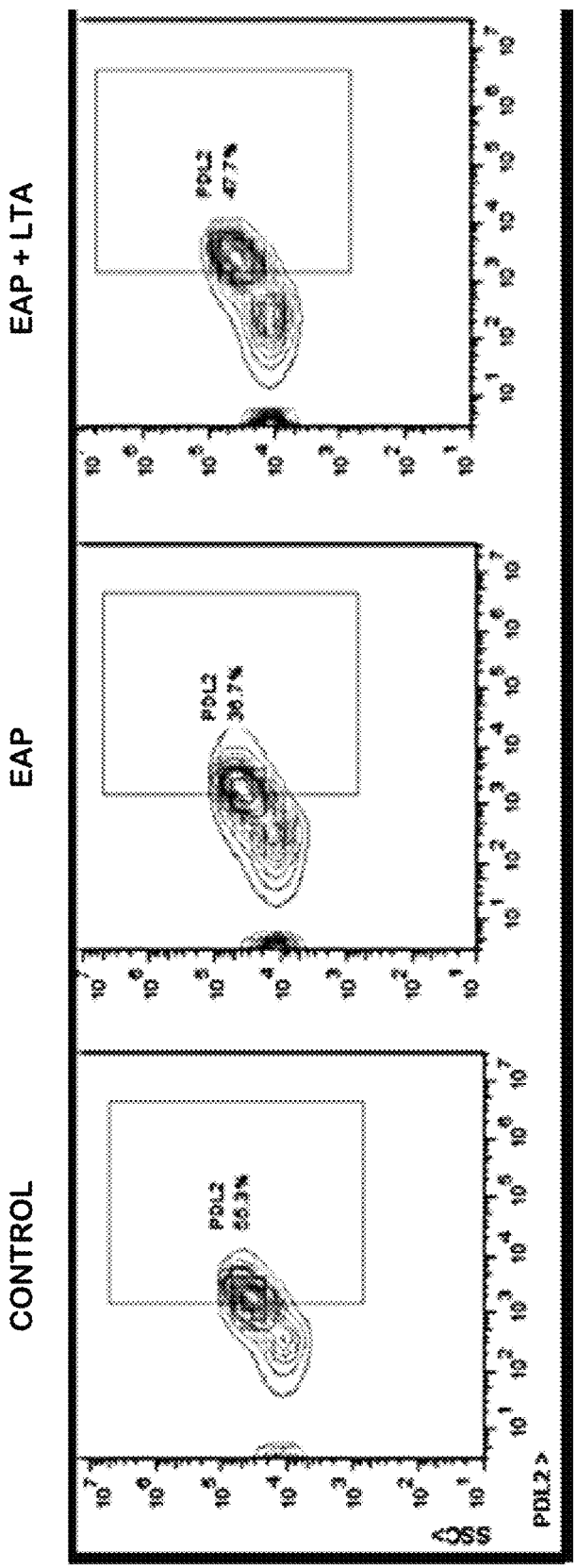
Figure 7B:
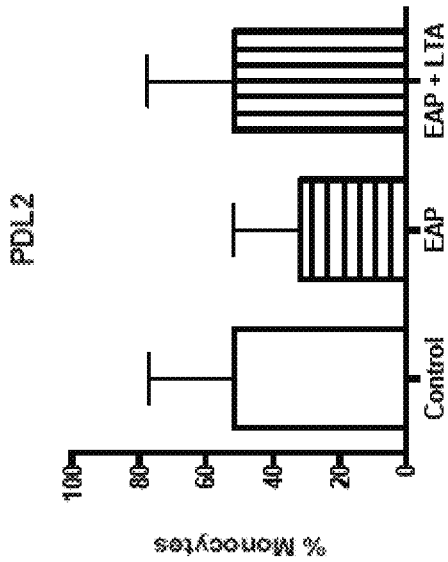
Figure 7D:
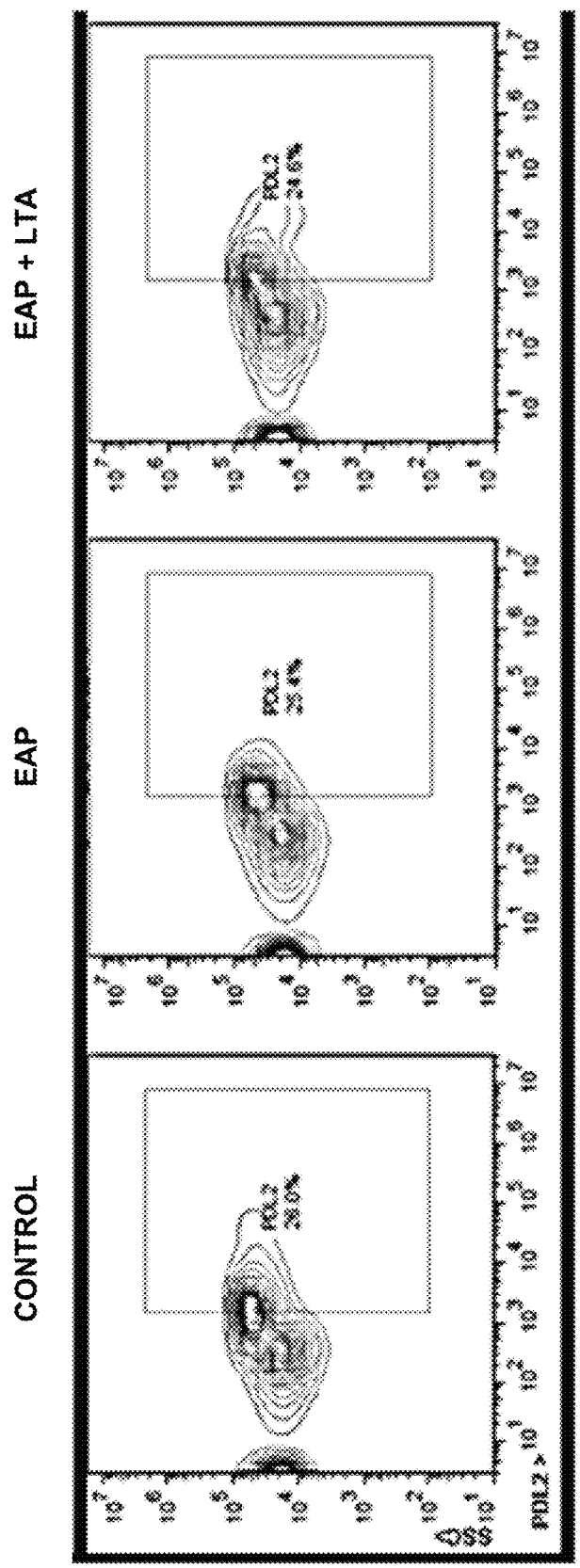
Figure 7D:
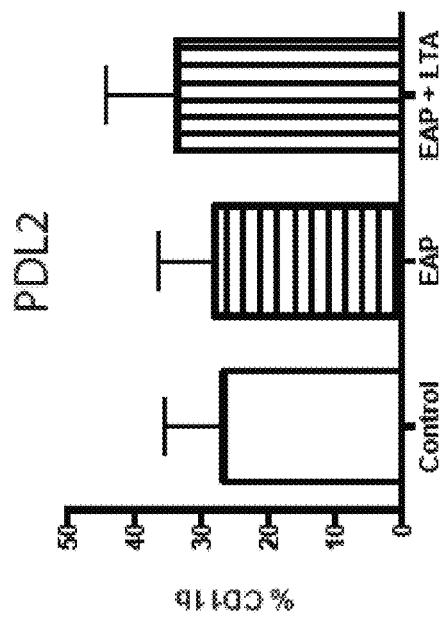
Figure 7E:
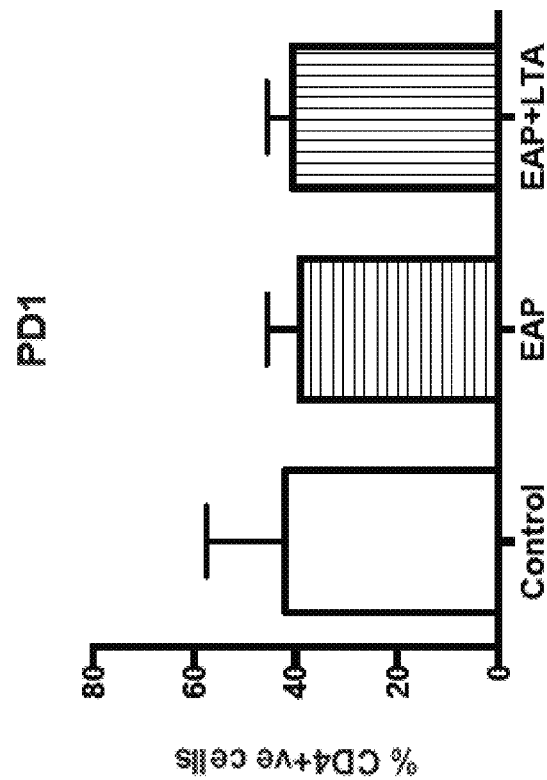
Figure 7E:
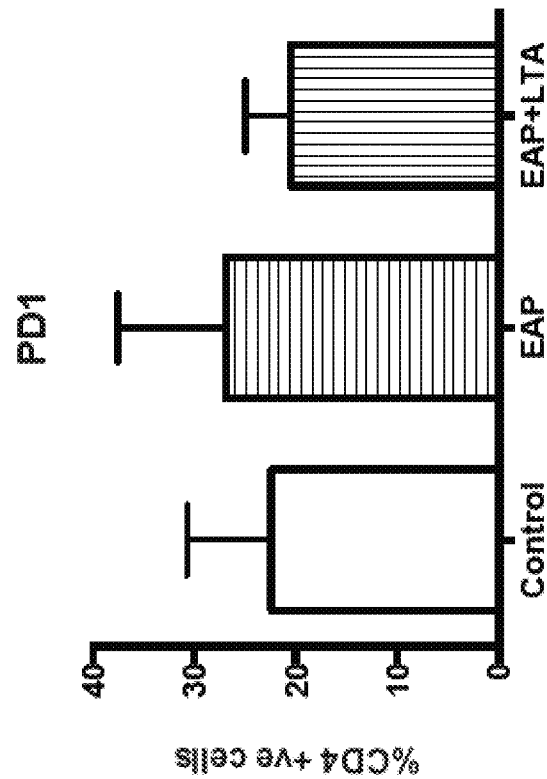

TLR2 is expressed on a wide variety of tissues including macrophages and dendritic cells (refs. 3,41; incorporated by reference in their entireties). Given the ability of these monocytic cell types to modulate CD4 T-cell activation and differentiation, experiments were conducted during development of embodiments herein to examine the effect of LTA on CD11b+ve monocytes in the prostate. Findings indicate that this specific LTA dampens pro-inflammatory Th17 responses; therefore, experiments focused on the expression of the negative CTLA4-like co-stimulatory molecules PDL1 and PDL2 in response to EAP and/or LTA treatment in prostate tissues. Flow cytometry revealed that although EAP induction had no effect on PDL1/2 expression on CD11b+ve cells at day 28, EAP followed by LTA treatment significantly increased expression level of these ligands, FIG. 5A. Data from iliac lymph node and bladder tissues revealed that these increases were prostate tissue specific (FIG. 7A-D). To further demonstrate these increases, immune-fluorescent staining for PDL1 and PDL2 was performed on prostate sections from EAP and EAP and LTA treated mice, FIG. 5C, and D. The cognate receptor for the PDL1/2 ligands, PD-1, is expressed on the surface of the CD4 T-cell (refs. 42,47; incorporated by reference in their entireties). Flow cytometric analysis revealed a slight increase in PD-1 expression upon LTA treatment in EAP mice (FIG. 5E) that was also prostate specific. These data indicate that LTA exploits the negative feedback loop induced by engagement of TLR2 to dampen CD4+ve T-effector cell activation by inhibiting T-cell co-stimulation.

Modulations in Referred Pain are Dependent on IL10, PD1 and CD25 Expressing Cells.

Figure 8A:
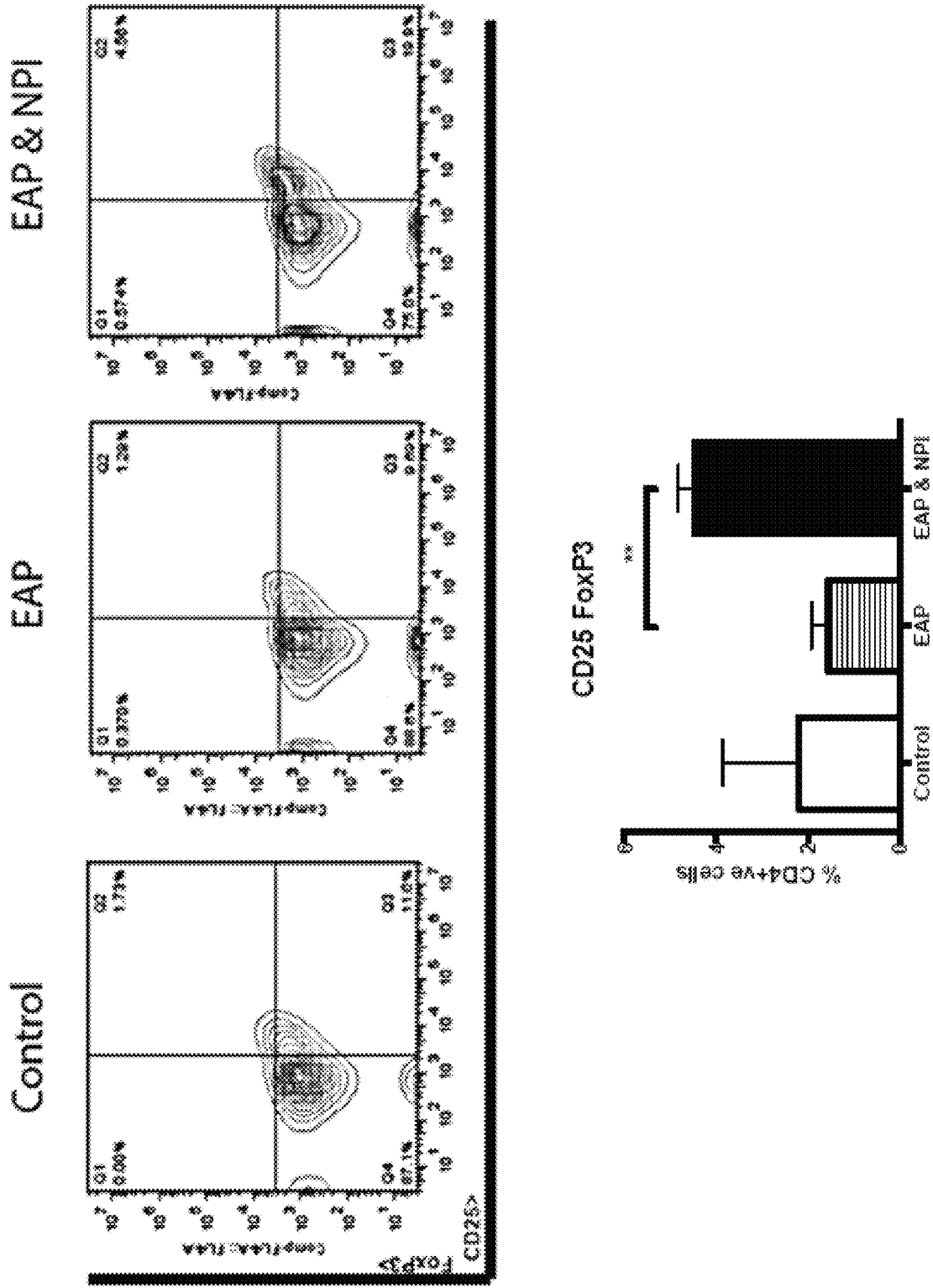
FIGS. 8A-B. LTA increases number of CD4 CD25 FoxP3+ve T-regs in prostate tissues. Representative flow cytometry plots for CD25 and FoxP3 expression (gated on lymphocytes and in CD4 expression) in single cell suspensions of (FIG. 8A) prostate tissues and (FIG. 8B) iliac lymph nodes from control and NPI instilled C57BL/6 mice.
Figure 8B:
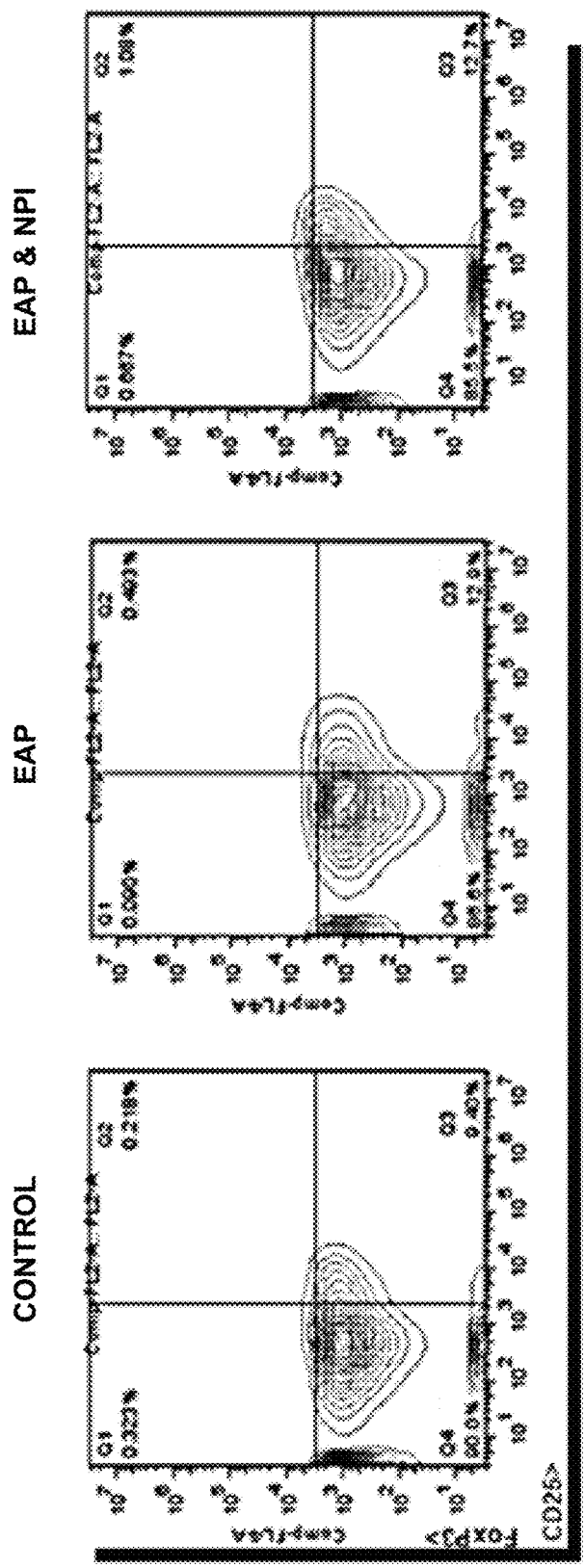
Figure 8B:
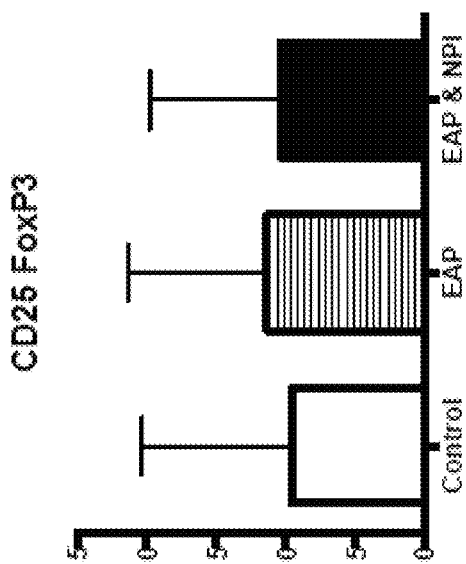
Figure 9A:
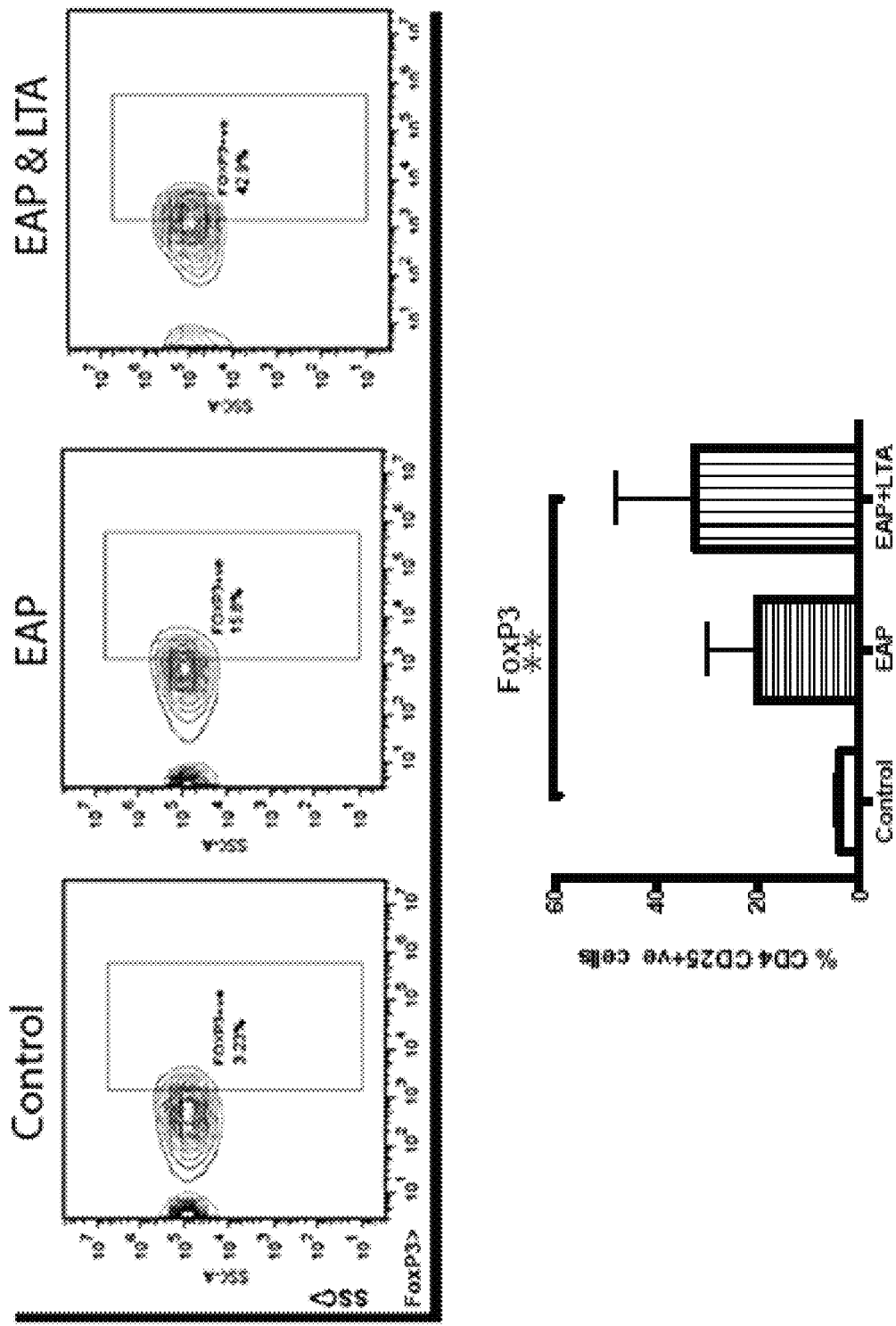
FIGS. 9A-B. NPI increases number of CD4 CD25 FoxP3+ve T-regs in prostate tissues. Representative flow cytometry plots for CD25 and FoxP3 expression (gated on lymphocytes and CD4 expression) in single cell suspensions of (FIG. 9A) prostate tissues and (FIG. 9B) iliac lymph nodes from control and NPI instilled C57BL/6 mice.
Figure 9B:
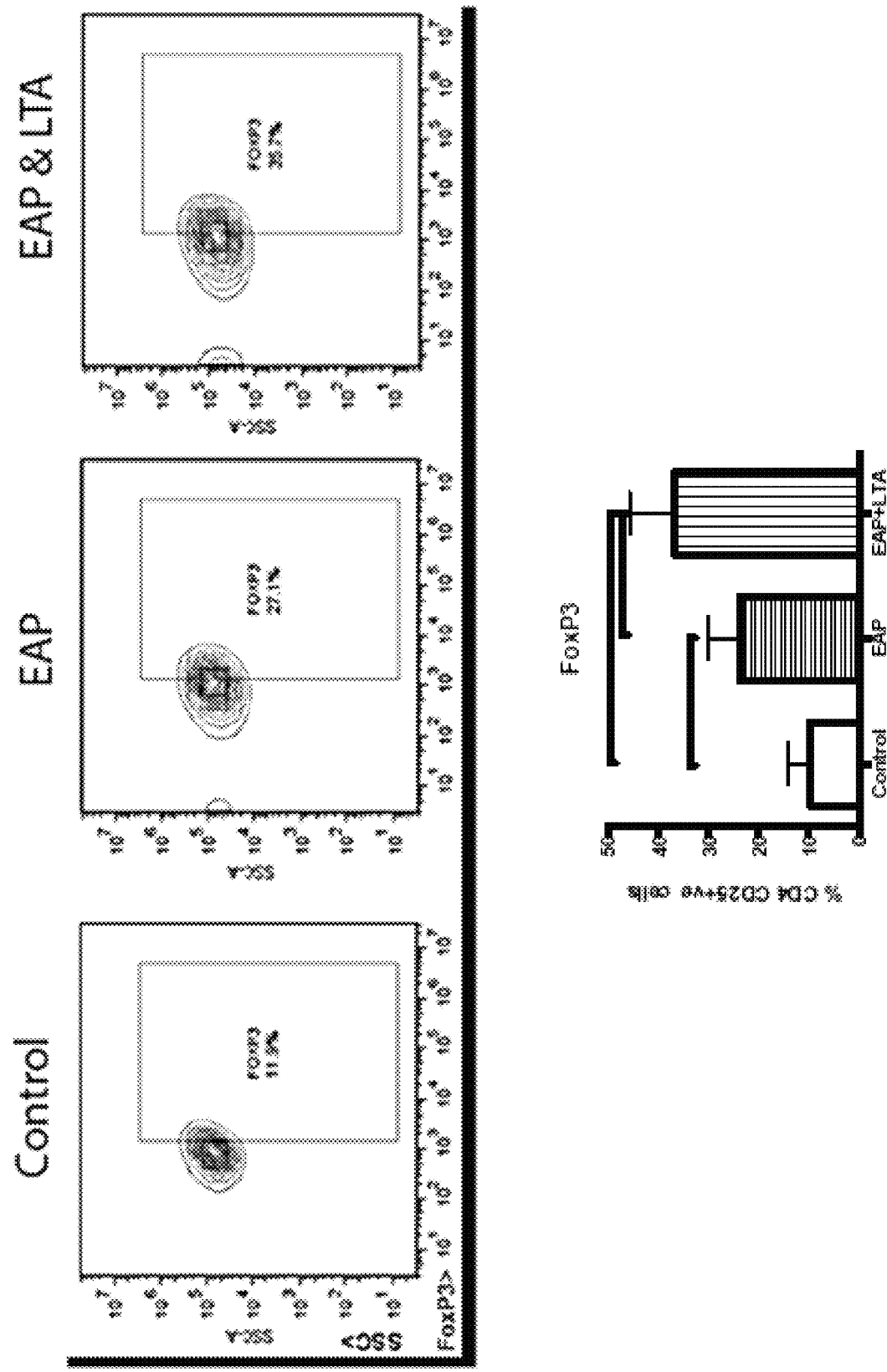

Given the increased level of PDL1 and PDL2 expression associated with LTA treatment, experiments were conducted during development of embodiments herein to determine whether IL10 secreted by CD11b+ve cells may serve to dampen tactile allodynia responses in the prostate. Such increases in IL10 secretion could also account for the decreased levels of IL17 expressing CD4+ve T-cells observed when EAP mice are treated with either NPI or NPI-LTA. To interrogate this, EAP was induced in IL10KO mice and subsequently one group was instilled with NPI at day 21. As demonstrated in FIG. 6A-C, IL10KO mice develop tactile allodynia in response to EAP similarly to C57BL/6 animals but these tactile allodynia responses are not ameliorated by instillation with the NPI bacteria. IL10 secretion from APCs is tied to PDL1 and PDL2 function and in order to further highlight their role in mitigating tactile allodynia and to investigate the source of IL10 we performed an antibody blocking experiment directed against both the PD1 receptor and CD25, a surface marker of IL10 producing T-regulatory cells. Antibody treatment was initiated at Day 19 post-EAP induction and repeated every two days until experimental end point. LTA treatment was given at Day 21 and behavioral testing performed every two days until Day 28. FIG. 6 d-f, demonstrate that antibody blockade of PD1 and/or CD25 prevented LTA treatment from amelioration of tactile allodynia. Taken together these data highlight the role of the PD1: PDL1/2 pathway, IL10 production and CD25 expressing cells in modulating tactile allodynia in response to NPI and NPI-LTA treatment. Flow cytometric analyses of CD4+CD25+FoxP3+ve T-cells in response to NPI instillation and NPI-LTA treatment in both prostate and iliac lymph node tissues revealed a trend towards increased numbers of these cells, (FIGS. 8 & 9). T-regulatory cells are induced by IL10 secretion and can dampen activated CD4 T-cell responses such as IL17. Additionally, expression of PDL1 and PDL2 are induced by IL10 and FoxP3+ve cells are a source of IL-10 (refs. 30,43,45; incorporated by reference in their entireties). These data further point to the role of IL10 and modulation of T-cell immunity in amelioration of tactile allodynia responses.

Example 2

Testing the Effectiveness of Lipotechoic Acid (LTA) in Collagen Induced Arthritis (CIA)

Figure 10A:
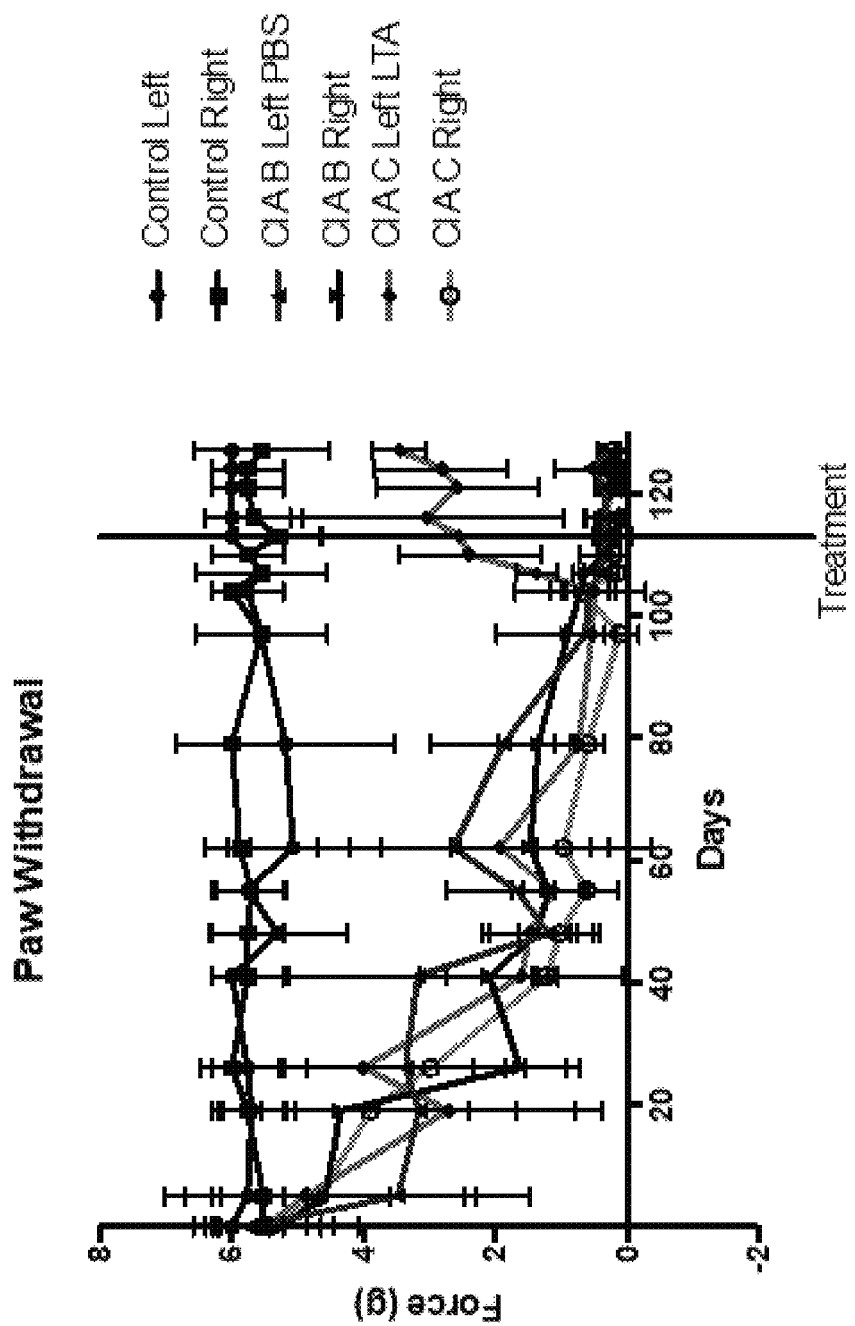
FIGS. 10A-B. Paw withdrawal threshold scores.

Collagen Induced Arthritis (CIA) is a murine model of autoimmune driven arthritis (e.g., rheumatoid arthritis) induced by intradermal tail vein injection of collagen antigen and Complete Freud's Adjuvant (CFA). The model induces joint destruction and immune cell infiltration into the joints of the hind limbs and paws of affected mice. This model was used as it has been shown to be mediated by IL17 expression and also has technical similarities to the experimental auto-immune prostatitis (EAP) model where pelvic tactile allodynia is induced by subcutaneous injection of prostate antigen and an adjuvant. In order to assess arthritis onset in our C57BL/6 animals, paw withdrawal testing was performed, which uses Von Frey filaments to examine the force necessary for mouse paw withdrawal from filaments with varying hardness. The lower the force necessary for paw retraction indicating a hyper-response to the filaments and thus paw discomfort. This acted as a non-invasive metric for extent of allodynia and arthritis in affected mice. Experiments conducted during development of embodiments herein demonstrate effective induction of the model in both paws of treated mice (CIA B and CIA C above) compared to Naïve control animals (FIG. 10A). Disease course was followed over a period of 100 days with a booster injection given at Day 60 in order to ensure maximum responses.

Figure 10B:
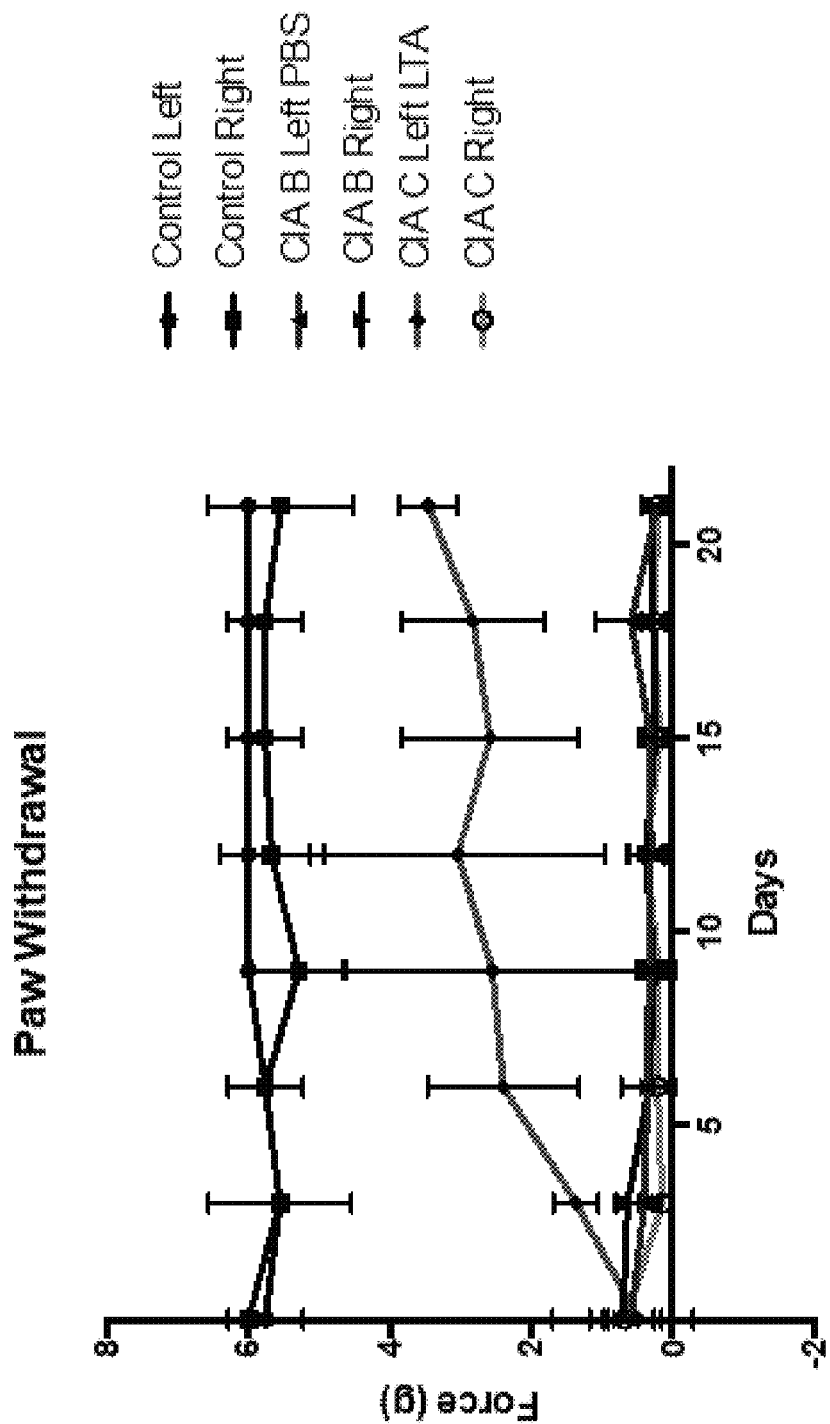

Treatment with the Lipotechoic acid (LTA) moiety was performed at day 104 and repeated every 3 days to allow for mouse recovery following injection. LTA was applied by direction injection into the mouse foot-pad. Paw-withdrawal measurements post-treatment from day 0 and continued until day 21 (FIG. 10B). Mice were treated only in their left paw allowing an internal control for each animal (untreated right paw). Mice treated with LTA (CIA C Left LTA) above show decreased paw-withdrawal as early as Day 3 post-treatment, which continues for the term of the experiment. The right paw of these mice or the sham-injected group did not show such amelioration of symptoms. Taken together these data demonstrate effective induction of CIA in these animals and that hyper-responsiveness to Von Frey filaments can be reversed upon localized treatment with LTA.

REFERENCES

The following references, some of which are cited above by number, are herein incorporated by reference in their entireties.

[1] Belkaid Y, Naik S. Compartmentalized and systemic control of tissue immunity by commensals. Nature immunology 2013; 14 (7): 646-653.

[2] Belkaid Y, Segre J A. Dialogue between skin microbiota and immunity. Science 2014; 346 (6212): 954-959.

[3] Benwell R K, Lee D R. Essential and synergistic roles of IL1 and IL6 in human Th17 differentiation directed by TLR ligand-activated dendritic cells. Clinical immunology 2010; 134 (2): 178-187.

[4] Bowie W R, Pollock H M, Forsyth P S, Floyd J F, Alexander E R, Wang S P, Holmes K K. Bacteriology of the urethra in normal men and men with nongonococcal urethritis. Journal of clinical microbiology 1977; 6 (5): 482-488.

[5] Buttner H, Mack D, Rohde H. Structural basis of *Staphylococcus epidermidis* biofilm formation: mechanisms and molecular interactions. Frontiers in cellular and infection microbiology 2015; 5:14.

[6] Chiu I M, Heesters B A, Ghasemlou N, Von Hehn C A, Zhao F, Tran J, Wainger B, Strominger A, Muralidharan S, Horswill A R, Bubeck Wardenburg J, Hwang S W, Carroll M C, Woolf C J. Bacteria activate sensory neurons that modulate pain and inflammation. Nature 2013; 501 (7465): 52-57.

[7] Christensen G J, Bruggemann H. Bacterial skin commensals and their role as host guardians. Beneficial microbes 2014; 5 (2): 201-215.

[8] Desireddi N V, Campbell P L, Stern J A, Sobkoviak R, Chuai S, Shahrara S, Thumbikat P, Pope R M, Landis J R, Koch A E, Schaeffer A J. Monocyte chemoattractant protein-1 and macrophage inflammatory protein-1alpha as possible biomarkers for the chronic pelvic pain syndrome. The Journal of urology 2008; 179 (5): 1857-1861; discussion 1861-1852.

[9] Gaddis D E, Maynard C L, Weaver C T, Michalek S M, Katz J. Role of TLR2-dependent IL-10 production in the inhibition of the initial IFN-gamma T cell response to *Porphyromonas gingivalis*. Journal of leukocyte biology 2013; 93 (1): 21-31.

[10] Gallegos A M, Bevan M J. Driven to autoimmunity: the nod mouse. Cell 2004; 117 (2): 149-151.

[11] Gallo R L, Nakatsuji T. Microbial symbiosis with the innate immune defense system of the skin. The Journal of investigative dermatology 2011; 131 (10): 1974-1980.

[12] Gao Y, Chen L, Hou M, Chen Y, Ji M, Wu H, Wu G. TLR2 directing P D-L2 expression inhibit T cells response in *Schistosoma japonicum* infection. PloS one 2013; 8 (12): e82480.

[13] Hou D S, Long W M, Shen J, Zhao L P, Pang X Y, Xu C. Characterisation of the bacterial community in expressed prostatic secretions from patients with chronic prostatitis/chronic pelvic pain syndrome and infertile men: a preliminary investigation. Asian journal of andrology 2012; 14 (4): 566-573.

[14] Huang B R, Tsai C F, Lin H Y, Tseng W P, Huang S S, Wu C R, Lin C, Yeh W L, Lu D Y. Interaction of inflammatory and anti-inflammatory responses in microglia by *Staphylococcus aureus*-derived lipoteichoic acid. Toxicology and applied pharmacology 2013; 269 (1): 43-50.

[15] Kim C F, Moalem-Taylor G. Interleukin-17 contributes to neuroinflammation and neuropathic pain following peripheral nerve injury in mice. The journal of pain: official journal of the American Pain Society 2011; 12 (3): 370-383.

[16] Kirschning C J, Bauer S. Toll-like receptors: cellular signal transducers for exogenous molecular patterns causing immune responses. International journal of medical microbiology: IJMM 2001; 291 (4): 251-260.

[17] Kunz M, Ibrahim S M. Cytokines and cytokine profiles in human autoimmune diseases and animal models of autoimmunity. Mediators of inflammation 2009; 2009: 979258.

[18] Kuriya G, Uchida T, Akazawa S, Kobayashi M, Nakamura K, Satoh T, Horie I, Kawasaki E, Yamasaki H, Yu L, Iwakura Y, Sasaki H, Nagayama Y, Kawakami A, Abiru N. Double deficiency in IL-17 and IFN-gamma signalling significantly suppresses the development of diabetes in the NOD mouse. Diabetologia 2013; 56 (8): 1773-1780.

[19] Lewis D A, Brown R, Williams J, White P, Jacobson S K, Marchesi J R, Drake M J. The human urinary microbiome; bacterial DNA in voided urine of asymptomatic adults. Frontiers in cellular and infection microbiology 2013; 3:41.

[20] Liu Y, Yin H, Zhao M, Lu Q. TLR2 and TLR4 in autoimmune diseases: a comprehensive review. Clinical reviews in allergy & immunology 2014; 47 (2): 136-147.

[21] Magetsari Ph D R, Dewo Ph D P, Saputro Md B K, Lanodiyu Md Z. Cinnamon Oil and Chitosan Coating on Orthopaedic Implant Surface for Prevention of *Staphylococcus Epidermidis* Biofilm Formation. Malaysian orthopaedic journal 2014; 8 (3): 11-14.

[22] McMahon S B, La Russa F, Bennett D L. Crosstalk between the nociceptive and immune systems in host defence and disease. Nature reviews Neuroscience 2015; 16 (7): 389-402.

[23] Morrison P J, Bending D, Fouser L A, Wright J F, Stockinger B, Cooke A, Kullberg M C. Th17-cell plasticity in *Helicobacter hepaticus*-induced intestinal inflammation. Mucosal immunology 2013; 6 (6): 1143-1156.

[24] Murphy A C, Lalor S J, Lynch M A, Mills K H. Infiltration of Th1 and Th17 cells and activation of microglia in the CNS during the course of experimental autoimmune encephalomyelitis. Brain, behavior, and immunity 2010; 24 (4): 641-651.

[25] Murphy S F, Schaeffer A J, Done J, Wong L, Bell-Cohn A, Roman K, Cashy J, Ohlhausen M, Thumbikat P. IL17 Mediates Pelvic Pain in Experimental Autoimmune Prostatitis (EAP). PloS one 2015; 10 (5): e0125623.

[26] Naik S, Bouladoux N, Linehan J L, Han S J, Harrison O J, Wilhelm C, Conlan S, Himmelfarb S, Byrd A L, Deming C, Quinones M, Brenchley J M, Kong H H, Tussiwand R, Murphy K M, Merad M, Segre J A, Belkaid Y. Commensal-dendritic-cell interaction specifies a unique protective skin immune signature. Nature 2015; 520 (7545): 104-108.

[27] Naik S, Bouladoux N, Wilhelm C, Molloy M J, Salcedo R, Kastenmuller W, Deming C, Quinones M, Koo L, Conlan S, Spencer S, Hall J A, Dzutsev A, Kong H, Campbell D J, Trinchieri G, Segre J A, Belkaid Y. Compartmentalized control of skin immunity by resident commensals. Science 2012; 337 (6098): 1115-1119.

[28] Nickel J C, Stephens A, Landis J R, Chen J, Mullins C, van Bokhoven A, Lucia M S, Melton-Kreft R, Ehrlich G D. Search for Microorganisms in Men with Urologic Chronic Pelvic Pain Syndrome: A Culture-Independent Analysis in the MAPP Research Network. The Journal of urology 2015.

[29] Pietrocola G, Arciola C R, Rindi S, Di Poto A, Missineo A, Montanaro L, Speziale P. Toll-like receptors (TLRs) in innate immune defense against *Staphylococcus aureus*. The International journal of artificial organs 2011; 34 (9): 799-810.

[30] Polanczyk M J, Hopke C, Vandenbark A A, Offner H. Estrogen-mediated immunomodulation involves reduced activation of effector T cells, potentiation of Treg cells, and enhanced expression of the PD-1 costimulatory pathway. Journal of neuroscience research 2006; 84 (2): 370-378.

[31] Quick M L, Done J D, Thumbikat P. Measurement of tactile allodynia in a murine model of bacterial prostatitis. Journal of visualized experiments: JoVE 2013 (71): e50158.

[32] Quick M L, Wong L, Mukherjee S, Done J D, Schaeffer A J, Thumbikat P. Th1-Th17 cells contribute to the development of uropathogenic *Escherichia coli*-induced chronic pelvic pain. PloS one 2013; 8 (4): e60987.

[33] Rashidi N, Mirahmadian M, Jeddi-Tehrani M, Rezania S, Ghasemi J, Kazemnejad S, Mirzadegan E, Vafaei S, Kashanian M, Rasoulzadeh Z, Zarnani A H. Lipopolysaccharide- and Lipoteichoic Acid-mediated Pro-inflammatory Cytokine Production and Modulation of TLR2, TLR4 and MyD88 Expression in Human Endometrial Cells. Journal of reproduction & infertility 2015; 16 (2): 72-81.

[34] Rivero V E, Cailleau C, Depiante-Depaoli M, Riera C M, Carnaud C. Non-obese diabetic (NOD) mice are genetically susceptible to experimental autoimmune prostatitis (EAP). Journal of autoimmunity 1998; 11 (6): 603-610.

[35] Roman K, Done J D, Schaeffer A J, Murphy S F, Thumbikat P. Tryptase-PAR2 axis in experimental autoimmune prostatitis, a model for chronic pelvic pain syndrome. Pain 2014; 155 (7): 1328-1338.

[36] Round J L, Lee S M, Li J, Tran G, Jabri B, Chatila T A, Mazmanian S K. The Toll-like receptor 2 pathway establishes colonization by a commensal of the human microbiota. Science 2011; 332 (6032): 974-977.

[37] Rudick C N, Berry R E, Johnson J R, Johnston B, Klumpp D J, Schaeffer A J, Thumbikat P. Uropathogenic *Escherichia coli* induces chronic pelvic pain. Infection and immunity 2011; 79 (2): 628-635.

[38] Rudick C N, Billips B K, Pavlov V I, Yaggie R E, Schaeffer A J, Klumpp D J. Host-pathogen interactions mediating pain of urinary tract infection. The Journal of infectious diseases 2010; 201 (8): 1240-1249.

[39] Rudick C N, Schaeffer A J, Thumbikat P. Experimental autoimmune prostatitis induces chronic pelvic pain. American journal of physiology Regulatory, integrative and comparative physiology 2008; 294 (4): R1268-1275.

[40] Singh R P, Hasan S, Sharma S, Nagra S, Yamaguchi D T, Wong D, Bh H, Hossain A. Th17 cells in inflammation and autoimmunity. Autoimmunity reviews 2014.

[41] Stokes J A, Corr M, Yaksh T L. Spinal toll-like receptor signaling and nociceptive processing: regulatory balance between TIRAP and TRIF cascades mediated by TNF and IFNbeta. Pain 2013; 154 (5): 733-742.

[42] Tang X, Li Q, Zhu Y, Zheng D, Dai J, Ni W, Wei J, Xue Y, Chen K, Hou W, Zhang C, Feng X, Liang Y. The advantages of PD1 activating chimeric receptor (PD1-ACR) engineered lymphocytes for PDL1 (+) cancer therapy. American journal of translational research 2015; 7 (3): 460-473.

[43] Tripathi S, Guleria I. Role of PD1/PDL1 pathway, and TH17 and treg cells in maternal tolerance to the fetus. Biomedical journal 2015; 38 (1): 25-31.

[44] von Aulock S, Morath S, Hareng L, Knapp S, van Kessel K P, van Strijp J A, Hartung T. Lipoteichoic acid from *Staphylococcus aureus* is a potent stimulus for neutrophil recruitment. Immunobiology 2003; 208 (4): 413-422.

[45] Wang J, Roderiquez G, Norcross M A. Control of adaptive immune responses by *Staphylococcus aureus* through IL-10, P D-L1, and TLR2. Scientific reports 2012; 2:606.
[46] Woolley P D, Kinghorn G R, Talbot M D, Duerden B I. Microbiological flora in men with non-gonococcal urethritis with particular reference to anaerobic bacteria. International journal of STD & AIDS 1990; 1 (2): 122-125.
[47] Yao S, Zhu Y, Chen L. Advances in targeting cell surface signalling molecules for immune modulation. Nature reviews Drug discovery 2013; 12 (2): 130-146.
[48] Yu H, Meng H, Zhou F, Ni X, Shen S, Das U N. Urinary microbiota in patients with prostate cancer and benign prostatic hyperplasia. Archives of medical science: AMS 2015; 11 (2): 385-394.
[49] Zhang Y, Fu Y, Yu J, Ai Q, Li J, Peng N, Song S, He Y, Wang Z. Synergy of ambroxol with vancomycin in elimination of catheter-related *Staphylococcus epidermidis* biofilm in vitro and in vivo. Journal of infection and chemotherapy: official journal of the Japan Society of Chemotherapy 2015.
[50] Zielinski C E, Mele F, Aschenbrenner D, Jarrossay D, Ronchi F, Gattorno M, Monticelli S, Lanzavecchia A, Sallusto F. Pathogen-induced human TH17 cells produce IFN-gamma or IL-10 and are regulated by I L-Ibeta. Nature 2012; 484 (7395): 514-518.
[51] Murphy S F, et al. Commensal bacterial modulation of the host immune response to ameliorate pain in a murine model of chronic prostatitis. Pain 2017; 158 (8): 1517-1527.

We claim:

1. A method of treating an inflammation-related and/or immune-related autoimmune disease or condition in a subject, the method comprising administering to the subject s composition formulated for administration to a subject comprising lipoteichoic acid (LTA) obtained from a non-pain-inducing (NPI) strain of *Staphylococcus epidermidis* having the deposit number PTA-127829.

2. The method of claim 1, wherein an immune response of the subject is modulated.

3. The method of claim 1, wherein the disease is chronic pelvic pain syndrome (CPPS).

4. The method of claim 1, wherein the disease is rheumatoid arthritis.

5. The method of claim 1, wherein the composition is administered orally.

6. The method of claim 1, wherein the composition is administered rectally.

* * * * *

SEQUENCE LISTING

```
<160> NUMBER OF SEQ ID NOS: 20

<210> SEQ ID NO 1
<211> LENGTH: 18
<212> TYPE: DNA
<213> ORGANISM: Mus musculus

<400> SEQUENCE: 1
caactcccgc cagcagat                                                       18

<210> SEQ ID NO 2
<211> LENGTH: 21
<212> TYPE: DNA
<213> ORGANISM: Mus musculus

<400> SEQUENCE: 2
gctcaaggag accaccatgt g                                                   21

<210> SEQ ID NO 3
<211> LENGTH: 20
<212> TYPE: DNA
<213> ORGANISM: Mus musculus

<400> SEQUENCE: 3
tgttcccagc cgtttctacc                                                     20

<210> SEQ ID NO 4
<211> LENGTH: 20
<212> TYPE: DNA
<213> ORGANISM: Mus musculus

<400> SEQUENCE: 4
acactgcatc ttggctttgc                                                     20

<210> SEQ ID NO 5
<211> LENGTH: 20
<212> TYPE: DNA
<213> ORGANISM: Mus musculus

<400> SEQUENCE: 5
aagctcagta tccgctgacg                                                     20

<210> SEQ ID NO 6
<211> LENGTH: 20
<212> TYPE: DNA
<213> ORGANISM: Mus musculus
```

```
<400> SEQUENCE: 6
ccatatccac ggatgcgaca                                               20

<210> SEQ ID NO 7
<211> LENGTH: 20
<212> TYPE: DNA
<213> ORGANISM: Mus musculus

<400> SEQUENCE: 7
agggcctaca atgccaacaa                                               20

<210> SEQ ID NO 8
<211> LENGTH: 20
<212> TYPE: DNA
<213> ORGANISM: Mus musculus

<400> SEQUENCE: 8
tctccaccgc aatgaagacc                                               20

<210> SEQ ID NO 9
<211> LENGTH: 20
<212> TYPE: DNA
<213> ORGANISM: Mus musculus

<400> SEQUENCE: 9
cacccaggaa agacacaacc                                               20

<210> SEQ ID NO 10
<211> LENGTH: 20
<212> TYPE: DNA
<213> ORGANISM: Mus musculus

<400> SEQUENCE: 10
aagggttact tgggttgcca                                               20

<210> SEQ ID NO 11
<211> LENGTH: 19
<212> TYPE: DNA
<213> ORGANISM: Mus musculus

<400> SEQUENCE: 11
ccgggaatgg acagtcaca                                                19

<210> SEQ ID NO 12
<211> LENGTH: 18
<212> TYPE: DNA
<213> ORGANISM: Mus musculus

<400> SEQUENCE: 12
gcgaaggcga acctcctc                                                 18

<210> SEQ ID NO 13
<211> LENGTH: 20
<212> TYPE: DNA
<213> ORGANISM: Mus musculus

<400> SEQUENCE: 13
gctcggaact ccgcttcata                                               20

<210> SEQ ID NO 14
<211> LENGTH: 21
<212> TYPE: DNA
<213> ORGANISM: Mus musculus
```

```
<400> SEQUENCE: 14
ctttcaatga ctgtgccgtg g                                              21

<210> SEQ ID NO 15
<211> LENGTH: 20
<212> TYPE: DNA
<213> ORGANISM: Mus musculus

<400> SEQUENCE: 15
gatacctctg caccgtagcc                                                20

<210> SEQ ID NO 16
<211> LENGTH: 20
<212> TYPE: DNA
<213> ORGANISM: Mus musculus

<400> SEQUENCE: 16
cgttgctgtg aggacgtttg                                                20

<210> SEQ ID NO 17
<211> LENGTH: 20
<212> TYPE: DNA
<213> ORGANISM: Mus musculus

<400> SEQUENCE: 17
cagctccaca ccaccgtatt                                                20

<210> SEQ ID NO 18
<211> LENGTH: 20
<212> TYPE: DNA
<213> ORGANISM: Mus musculus

<400> SEQUENCE: 18
tttccctccg cattgacaca                                                20

<210> SEQ ID NO 19
<211> LENGTH: 21
<212> TYPE: DNA
<213> ORGANISM: Mus musculus

<400> SEQUENCE: 19
gcaagagctc ttgtccattg a                                              21

<210> SEQ ID NO 20
<211> LENGTH: 20
<212> TYPE: DNA
<213> ORGANISM: Mus musculus

<400> SEQUENCE: 20
cctggggcat cacttctacc                                                20
```